(12) United States Patent
Bobo et al.

(10) Patent No.: US 7,255,874 B1
(45) Date of Patent: Aug. 14, 2007

(54) BIOCOMPATIBLE POLYMERS AND ADHESIVES: COMPOSITIONS, METHODS OF MAKING AND USES RELATED THERETO

(75) Inventors: John S. Bobo, Raleigh, NC (US); Julian A. Quintero, Raleigh, NC (US); Jerry Y. Jonn, Raleigh, NC (US); Joe B. Barefoot, Raleigh, NC (US); Jeffrey G. Clark, Raleigh, NC (US); Upvan Narang, Raleigh, NC (US); Scott Marc Cannizaro, Philadelphia, PA (US); J. Christopher Marmo, Danville, CA (US)

(73) Assignee: Closure Medical Corporation, Raleigh, NC (US)

( * ) Notice: Subject to any disclaimer, the term of this patent is extended or adjusted under 35 U.S.C. 154(b) by 626 days.

(21) Appl. No.: 10/024,143

(22) Filed: Dec. 21, 2001
(Under 37 CFR 1.47)

(51) Int. Cl.
*A61K 9/127* (2006.01)
(52) U.S. Cl. ...................................................... 424/450
(58) Field of Classification Search ..................... None
See application file for complete search history.

(56) References Cited

U.S. PATENT DOCUMENTS

| | | | |
|---|---|---|---|
| 2,776,232 A | | 1/1957 | Shearer, Jr. et al. |
| 2,784,127 A | * | 3/1957 | Joyner et al. ............... 428/442 |
| 3,527,841 A | * | 9/1970 | Wicker et al. ............... 528/354 |
| 3,559,652 A | | 2/1971 | Bannitt et al. |
| 3,654,239 A | | 4/1972 | McIntire et al. |
| 3,667,472 A | | 6/1972 | Halpern |
| 3,722,599 A | | 3/1973 | Robertson et al. |
| 3,759,264 A | | 9/1973 | Coover, Jr. et al. |
| 3,940,362 A | | 2/1976 | Overhults |
| 3,975,422 A | | 8/1976 | Buck |
| 3,995,641 A | | 12/1976 | Kronenthal et al. |
| 4,003,942 A | | 1/1977 | Buck |
| 4,012,402 A | | 3/1977 | Buck |
| 4,038,345 A | | 7/1977 | O'Sullivan et al. |
| 4,041,061 A | | 8/1977 | Buck |
| 4,127,382 A | | 11/1978 | Perry |
| 4,134,929 A | | 1/1979 | Stoakley et al. |
| 4,415,732 A | | 11/1983 | Caruthers et al. |
| 4,425,471 A | | 1/1984 | Millet |
| 4,444,933 A | | 4/1984 | Columbus et al. |
| 4,458,066 A | | 7/1984 | Caruthers et al. |
| 4,469,863 A | | 9/1984 | Ts'o et al. |
| 4,507,433 A | | 3/1985 | Miller et al. |
| 4,582,648 A | | 4/1986 | Hirakawa |
| 4,683,195 A | | 7/1987 | Mullis et al. |
| 4,711,955 A | | 12/1987 | Ward et al. |
| 4,725,677 A | | 2/1988 | Koster et al. |
| 4,741,337 A | | 5/1988 | Smith et al. |
| 4,757,055 A | | 7/1988 | Miller et al. |
| 4,828,979 A | | 5/1989 | Klevan et al. |
| 4,868,116 A | | 9/1989 | Morgan et al. |
| 4,948,882 A | | 8/1990 | Ruth |
| 4,973,679 A | | 11/1990 | Caruthers et al. |
| 4,980,286 A | | 12/1990 | Morgan et al. |
| 4,980,460 A | | 12/1990 | Molko et al. |
| 5,013,831 A | | 5/1991 | Stavrianopoulos |
| 5,041,602 A | * | 8/1991 | Nagai et al. ................ 558/401 |
| 5,091,557 A | | 2/1992 | Nagai et al. |
| 5,130,302 A | | 7/1992 | Spielvogel et al. |
| 5,151,510 A | | 9/1992 | Stec et al. |
| 5,166,320 A | | 11/1992 | Wu et al. |
| 5,166,387 A | | 11/1992 | Hirschbein |
| 5,175,337 A | | 12/1992 | Mikuni et al. |
| 5,183,885 A | | 2/1993 | Bergot |
| 5,190,922 A | | 3/1993 | Luly et al. |
| 5,241,060 A | | 8/1993 | Engelhardt et al. |
| 5,254,132 A | | 10/1993 | Barley et al. |
| 5,256,765 A | | 10/1993 | Leong |
| 5,264,618 A | | 11/1993 | Felgner et al. |
| 5,283,185 A | | 2/1994 | Epand et al. |
| 5,306,490 A | | 4/1994 | Barley, Jr. |
| 5,321,131 A | | 6/1994 | Agrawal et al. |
| 5,328,687 A | | 7/1994 | Leung et al. |
| 5,334,761 A | | 8/1994 | Gebeyehu et al. |
| 5,405,950 A | | 4/1995 | Mock et al. |
| 5,407,801 A | | 4/1995 | Miller |
| 5,414,077 A | | 5/1995 | Lin et al. |
| 5,504,252 A | | 4/1996 | Klemarczyk |

(Continued)

FOREIGN PATENT DOCUMENTS

EP          0 220 030 A2    4/1987

(Continued)

OTHER PUBLICATIONS

Chabaka et al., Amino Acid Derivatives in Organic Synthesis, Part 4[1]: Facile Synthesis of Heterocycles Containing a Glycine Residue, 2000, Verlag der Zeitschrift fur Naturforschung, 55b, pp. 104-108.*
STN, Search Results, (40 pages) 2000.
J-Surg-Res. Dec. 1989; 47(6); 48-92.
Klin-Khir. 1989 (10): 1-3.
Sov-Med. 1990 (1): 23-4.
Ghosh et al., J. Med. Chem., 1992, 35, 4175-4179.
Klemarczyk, P., Polymer, 1997, 39, 173-181.
Vauthier et al., Proceed. Intern. Symp. Control. Rel. Bioact. Mater. 1995, 22, 592-593.
Tuncel et al., J. Biomed. Mater. Research 1995, 29, 721-728.
Peracchia et al., J. Biomed. Mater. Research 1997, 34, 317-326.
Hillery et al., J. Controlled Release 1996, 42, 65-73.
Brady et al., 1998, J. Med. Chem., 41:401-406.

(Continued)

*Primary Examiner*—Michael Woodward
*Assistant Examiner*—Bethany P Barham

(57) ABSTRACT

Biocompatible polymers and adhesives have a cyanoacrylic core and other substituents such as therapeutic agents, targeting moieties, imaging agents, amino acid residues or other organic moieties. Exemplary uses of inventive compositions include use as sealants and adhesives for medical uses, and as polymeric formulations for biocompatible implants and matrices and drug delivery.

4 Claims, No Drawings

U.S. PATENT DOCUMENTS

| | | | |
|---|---|---|---|
| 5,514,378 A | 5/1996 | Mikos et al. |
| 5,518,730 A | 5/1996 | Fuisz |
| 5,550,172 A | 8/1996 | Regula et al. |
| 5,580,565 A | 12/1996 | Tighe et al. |
| 5,589,554 A | 12/1996 | Hiraoka |
| 5,624,669 A | 4/1997 | Leung et al. |
| 5,653,789 A | 8/1997 | Henise et al. |
| 5,654,010 A | 8/1997 | Johnson et al. |
| 5,674,534 A | 10/1997 | Zale et al. |
| 5,684,042 A | 11/1997 | Greff et al. |
| 5,688,488 A | 11/1997 | Low et al. |
| 5,711,968 A | 1/1998 | Tracy et al. |
| 5,716,594 A | 2/1998 | Elmaleh et al. |
| 5,721,277 A | 2/1998 | Tang |
| 5,725,568 A | 3/1998 | Hastings |
| 5,736,372 A | 4/1998 | Vacanti et al. |
| 5,759,830 A | 6/1998 | Vacanti et al. |
| 5,762,955 A | 6/1998 | Smith |
| 5,770,193 A | 6/1998 | Vacanti et al. |
| 5,783,171 A | 7/1998 | Gustavson et al. |
| 5,783,567 A | 7/1998 | Hedley et al. |
| 5,820,847 A | 10/1998 | Low et al. |
| 5,900,245 A | 5/1999 | Sawhney et al. |
| 5,925,628 A | 7/1999 | Lee et al. |
| 5,928,611 A | 7/1999 | Leung |
| 5,962,010 A | 10/1999 | Greff et al. |
| 5,981,621 A | 11/1999 | Clark et al. |
| 5,989,580 A | 11/1999 | Wallace et al. |
| 6,010,714 A | 1/2000 | Leung et al. |
| 6,099,807 A | 8/2000 | Leung et al. |
| 6,143,805 A | 11/2000 | Hickey et al. |
| 6,183,593 B1 | 2/2001 | Narang et al. |
| 6,217,603 B1 | 4/2001 | Clark et al. |
| 6,283,933 B1 | 9/2001 | D'Alessio et al. |
| 6,352,704 B1 | 3/2002 | Nicholson et al. |

FOREIGN PATENT DOCUMENTS

| | | |
|---|---|---|
| EP | 0 273 085 A1 | 7/1988 |
| EP | 0 411 893 A3 | 2/1991 |
| EP | 0 506 242 A1 | 9/1992 |
| WO | WO 89/02468 | 3/1989 |
| WO | WO 89/05345 | 6/1989 |
| WO | WO 89/07136 | 8/1989 |
| WO | WO 89/11486 | 11/1989 |
| WO | WO 90/15065 | 12/1990 |
| WO | WO 92/05186 | 4/1992 |
| WO | WO 92/06180 | 4/1992 |
| WO | WO 92/07573 | 5/1992 |
| WO | WO 92/19749 | 11/1992 |
| WO | WO 92/20316 | 11/1992 |
| WO | WO 92/20703 | 11/1992 |
| WO | WO 92/22635 | 12/1992 |
| WO | WO 93/01286 | 1/1993 |
| WO | WO 93/04701 | 3/1993 |
| WO | WO 93/09222 | 5/1993 |
| WO | WO 93/25196 | 12/1993 |
| WO | WO 93/25234 | 12/1993 |
| WO | WO 94/04171 | 3/1994 |
| WO | WO 94/06920 | 3/1994 |
| WO | WO 94/11524 | 5/1994 |
| WO | WO 94/12650 | 6/1994 |
| WO | WO 94/24095 | 10/1994 |
| WO | WO 95/31560 | 11/1995 |
| WO | WO 96/29411 | 9/1996 |
| WO | WO 01/12243 A1 | 2/2001 |
| WO | WO 01/30408 A2 | 5/2001 |
| WO | WO 01/32319 A2 | 5/2001 |
| WO | WO 01/32795 A1 | 5/2001 |

OTHER PUBLICATIONS

Carre et al., 1998 Journal of Fluorescence, 8(1):53-57.
Domb et al., 1989 Macromolecules, 22:3200.
Holland et al., 1986, Controlled Release, 4:155-180.
U.S. Appl. No. 09/176,889, filed Oct. 1998, K. R. D'Alessio et al.
U.S. Appl. No. 09/385,030, filed Aug. 1999, K. R. D'Alessio et al.
U.S. Appl. No. 09/430,176, filed Oct. 1999, U. Narang et al.
U.S. Appl. No. 09/430,177, filed Oct. 1999, U. Narang et al.
U.S. Appl. No. 09/430,180, filed Oct. 1999, W. S.C. Nicholson et al.
U.S. Appl. No. 09/430,289, filed Oct. 1999, K. R. D'Alessio et al.
U.S. Appl. No. 09/430,290, filed Oct. 1999, K. R. D'Alessio et al.
Heller et al., 1990 Biodegradable Polymers as Drug Delivery Systems, Chasin, M. and Langer, R., Eds., Dekker, New York, 121-161.
Spilizewski et al., 1985, "The Effect of Hydrocortisone Loaded Poly(dl-lactide) Films on the Inflammatory Response", J. Control. Rel. 2: 197-203.
Vacanti et al., "Selective Cell Transplantation Using Bioabsorbable Artificial Polymers as Matrices", J. Pediat. Surg. 23, 3-9 (1988).
Vacanti, "Beyond Transplantation", Arch. Surg. 123, 545-549 (1988).

* cited by examiner

BIOCOMPATIBLE POLYMERS AND ADHESIVES: COMPOSITIONS, METHODS OF MAKING AND USES RELATED THERETO

INTRODUCTION

The field of biodegradable polymers has developed rapidly since the synthesis and biodegradability of polylactic acid was first reported by Kulkarni et al., 1966 "Polylactic acid for surgical implants," Arch. Surg., 93:839. Several other polymers are known to biodegrade, including polyanhydrides and polyorthoesters, because of labile backbone linkages. Because it is desirable to have polymers that degrade into naturally occurring materials, polyaminoacids have been synthesized for in vivo use. This concept was the basis for using polyesters of alphahydroxy acids (e.g., lactic acid, glycolic acid), which remain the most widely used biodegradable materials for applications ranging from closure devices (sutures and staples) to drug delivery systems.

Biodegradable polymers have found a number of uses in medicine, such as drug delivery. However, many rapidly-degrading polymers currently suggested for short-term drug release often produce local concentrations of potentially hazardous acidic degradation byproducts. Further, many biodegradable synthetic polymers may be processed only in organic solvents, which may denature proteins or otherwise damage the agent to be delivered. Additionally, many biodegradable polymers are synthesized under conditions which are not amenable to polymerization in vivo. Thus, it may be difficult to make implantable materials as precisely conformed barriers, shaped articles, or membranes capable of delivering bioactive materials to the local tissue in a controlled fashion.

Wound closure is one potential use for biocompatible polymers and adhesives. Examples of products used for wound closure are surgical sutures and staples. Sutures are used to provide adequate wound support. However, use of sutures has a variety of potentially adverse consequences, including the following: they may cause additional trauma to the wound site (by reason of the need for the needle and suture to pass through tissue and the need to anesthetize the wound area before use of the needle); they may be time-consuming to place; and, at skin level, they may cause unattractive wound closure marks. Surgical staples have been developed in part to speed wound apposition and provide improved cosmetic results. However, surgical staples may also impose additional wound trauma and require the use of ancillary and often expensive devices for positioning and applying the staples. Both sutures and staples are especially problematic in cases presenting particular types of patients, including pediatric cases in which the patient may have a strong fear response and refuse to cooperate with their placement, and in geriatric cases in which the skin tissue is weaker and prone to tearing.

Surgical adhesives have been gaining in popularity in part because of their ability to address certain of these concerns. For example, alpha-cyanoacrylates have been used as surgical adhesives. Such polymers have the particular advantage of setting quickly, which setting may be initiated by simple application of the monomers to biological tissue. However, use of certain cyanoacrylates may produce significant levels of histotoxicity due to the surgical adhesive being trapped within the wound site. In addition, such adhesives posses a number of other problems relating to physical characteristics, such as tackiness, strength, ease of application and the like.

Thus some current biodegradable polymers and medical adhesives are susceptible to causing undesirable consequences, such as the release of toxic substances into the body and initiation of histological reactions. The current invention provides, in certain embodiments, novel compositions of biocompatible adhesives and polymers, and methods of using the same, that may address one or more of the foregoing concerns.

SUMMARY OF THE INVENTION

The present invention contemplates, in part, monomers and polymers derived therefrom, methods for preparing such monomers and polymers, and methods of treatment and otherwise using the subject monomers and polymers. In many of these embodiments, the subject compositions are biocompatible. In embodiments, the polymeric formulations of the present invention exhibit a variety of physical properties that make then suitable for treatment and other uses, including wound closure, sealing and other treatments of abrasions, burns, incisions, and the like. In embodiments, the compositions of the present invention, and methods of using the same, are capable of delivering a payload, such as a therapeutic agent or imaging agent. In embodiments, materials may be incorporated into polymeric formulations of the present invention, including biologically active substances.

In certain embodiments, the present invention relates to novel compositions of cyanoacrylic polymers and monomers, and uses thereof. In certain embodiments, a cyanoacrylic monomer of the present invention may include a cyanoacrylic core bound to a biocompatible substituted organic residue that, upon formation of a polymer and subsequent biodegradation of such polymer, results in biocompatible degradation products.

In embodiments, a monomer of the present invention may include a cyanoacrylic core bound to a payload, such as a therapeutic agent or imaging agent that, upon formation of a polymer and subsequent biodegradation of such polymer, results in release of such payload. Release of such payload may occur in a controlled release fashion, for example by hydrolysis. In addition, release of such payload may deliver the payload to a desired site.

In embodiments, different substances may be incorporated into the polymeric formulations of the present invention. In certain embodiments, the substances may be controllably released from the polymeric formulation. In certain embodiments, the polymeric formulations are prepared as particles, including microparticles and nanoparticles for particular applications.

Compositions of the present invention, and methods of using the same, have a variety of potentially desirable features, some of which may be present in certain embodiments of the invention. A non-limiting list of some of such features include: (i) the subject compositions may possess sufficient biocompatibility for particular treatments or uses; (ii) a single dose may be sufficient to achieve the desired therapeutically beneficial response through sustained release of the payload or materials incorporated into the composition; (iii) targeting moieties may be included in the payload or other materials incorporated into the subject compositions for potential targeting; (iv) polymeric formulations having certain dimensions may allow for receptor-mediated endocytosis of the polymer and, in certain instances, improved delivery of the payload or incorporated materials; (v) bioavailability of payloads and incorporated materials, including targeting agents and imaging agents, may be improved because of protection attributable to subject compositions from serum nuclease degradation and other undesirable reactions that may occur in any particular application; and (vi) therapeutic agents and other materials, including for example delivery agents, may be co-encapsulated in the polymeric formulations.

In another aspect, compositions of the present invention, and methods of using the same, may be used to deliver a transgene to a target site in a controlled release manner for gene transfer applications. In certain embodiments, the compositions of the present invention may be used to effect genetic immunization, whereby the payload is a nucleic acid that expresses an antigen to provoke an immunogenic response in the host. In still other embodiments, a delivery agent may be encapsulated in the compositions to facilitate the intracellular delivery of a nucleic acid.

In still another aspect, polymeric formulations of the present invention, and methods of using the same, may be used as matrices on which uniform cell growth and proliferation may occur under appropriate conditions. In certain embodiments, the subject matrix may be implanted in vivo and vascularization may occur.

In still another aspect, compositions of the present invention, and methods of using the same, may be used in diagnostic applications, such as in certain embodiments in which the payload is an imaging agent.

In another aspect, compositions of the present invention may be used in the manufacture of a medicament for any number of uses, including for example treating any disease or other treatable condition of a patient. In aspects, the present invention is directed to a method for formulating monomers and polymers of the present invention in a pharmaceutically acceptable carrier.

In embodiments, this invention contemplates a kit including compositions of the present invention, and optionally instructions for their use in methods described herein. For example, in embodiments, such kits include monomers incorporating a payload that upon use will form a polymeric formulation. Such kits may have a variety of uses, including, for example, imaging, diagnosis, therapy, vaccination, and other applications.

DETAILED DESCRIPTION

I. General

The present invention relates generally to monomer compositions, and polymer compositions derived therefrom. In certain embodiments, such compositions are derivatives of 2-cyanoacrylic acid. In embodiments, the carboxyl functionality is coupled to a biocompatible, functionalized residue, such as a therapeutic agent or imaging agent, including an amino acid, protein, bioactive or prodrug small organic molecule, ion chelating groups, antigen or antibody. Such compositions may be used in any of a variety of medical, pharmaceutical, or biological applications, such as medical adhesives, drug delivery, biocompatible coatings and tissue supports. Such compositions and uses are described in greater detail below. In addition, the subject invention provides processes of preparing such adhesives and polymers.

II. Definitions

For convenience, before further description of the present invention, certain terms employed in the specification, examples, and appended claims are collected here. These definitions should be read in light of the rest of the disclosure and understood as by a person of skill in the art.

The phrases "parenteral administration" and "administered parenterally" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, infra-articulare, subcapsular, subarachnoid, intraspinal and intrasternal injection and infusion.

The term "modulation" refers to both up-regulation (i.e., activation or stimulation) and down-regulation (i.e., inhibition or suppression) of a response, or the two in combination or apart.

The term "treating" is intended to encompass curing as well as ameliorating at least one symptom of any condition or disease.

The phrase "pharmaceutically acceptable" refers to those compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" means a pharmaceutically-acceptable material, composition or vehicle, such as a liquid or solid filler, diluent, excipient, solvent or encapsulating material, involved in carrying or transporting any composition, monomer, polymeric formulation or other material from one organ, or portion of the body, to another organ, or portion of the body. Each carrier must be "acceptable" in the sense of being compatible with the other ingredients of the composition and not injurious to the patient. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" refers to the relatively non-toxic, inorganic and organic acid addition salts of compositions of the present invention, including without limitation, payloads, therapeutic agents, imaging agents, monomers and the like.

The phrases "systemic administration," "administered systemically," "peripheral administration" and "administered peripherally" mean the administration of a subject supplement, composition, therapeutic or other material other than directly into the central nervous system, such that it enters the patient's system and, thus, is subject to metabolism and other like processes, for example, subcutaneous administration.

A "patient," "subject" or "host" to be treated by the subject method may mean either a human or non-human animal.

The phrase "therapeutically effective amount" means that amount of a composition, payload, agent or other material which is effective for producing some desired therapeutic effect, usually at a reasonable benefit/risk ratio applicable to any medical treatment, and includes both prophylactically effective amounts and therapeutically effective amounts unless otherwise specified or clear from the context. In certain embodiments, the term refers to that amount necessary or sufficient to eliminate, reduce or maintain (e.g., prevent the spread of) an infection, tumor or other target of a particular therapeutic regimen. The effective amount may vary depending on such factors as the disease or condition being treated, the particular targeted constructs being administered, the size of the subject and/or the severity of the disease or condition. One of ordinary skill in the art may empirically determine the effective amount of a particular compound without undue experimentation.

In certain embodiments of the present invention, a therapeutically effective amount of a payload, agent, monomer, polymer or other material for in vivo use will likely depend on a number of factors, which may include: the rate of release of an agent or other material from the subject composition, which will depend in part on the chemical and physical characteristics of such composition, the identity of the agent or other material, the mode and method of administration, and any other materials incorporated in the composition in addition to an agent.

The term "prophylactic or therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "biocompatibility" or "biocompatible" when used in relation to polymeric formulations, monomers, payloads and other compositions of the present invention refers to compositions that are neither themselves unduly toxic to the host (e.g., an animal or human) nor degrade (if at all) at a rate that produces byproducts at unduly toxic concentrations in the host.

To determine whether any subject material is biocompatible, it may be necessary to conduct a toxicity analysis. Such assays are well known in the art. One non-limiting example of such an assay for analyzing a composition of the present invention could be performed with live carcinoma cells, such as GT3TKB tumor cells, in the following manner: the sample composition is degraded in 1M NaOH at 37° C. until complete degradation is observed. The solution is then neutralized with 1 M HCl About 200 µL of various concentrations of the degraded composition products are placed in 96-well tissue culture plates and seeded with human gastric carcinoma cells (GT3TKB) at $10^4$/well density. The degraded products are incubated with the GT3TKB cells for 48 hours. The results of the assay may be plotted as % relative growth versus concentration of degraded composition in the tissue-culture well. In addition, polymers and compositions of the present invention may also be evaluated by well-known in vivo tests, such as subcutaneous implantations in rats to confirm that they do not cause unacceptable levels of irritation or inflammation at the subcutaneous implantation sites.

The term "biodegradable" and "bioerodible" refers to those embodiments in which compositions of the present invention dissolve or degrade (or are intended to dissolve or degrade) during use. In general, degradation attributable to biodegradability involves the degradation of a subject composition, for example, a polymeric formulation resulting from polymerization of a subject monomer (having a payload for example) into its constituents (including, without limitation, such payload and resulting degradation products). The degradation rate of a subject composition often depends in part on a variety of factors, including the identity of any constituents that form the subject composition (such as the identity of the monomer and the payload), the ratio of any substituents (such as one or more monomers comprising the resulting polymer formulation), how any subject composition is formed or treated (such as polymerization conditions). For example, a subject polymer formulation that experiences greater cross-linking will, in all likelihood, degrade more slowly than one that is not cross-linked.

In certain embodiments, polymeric formulations of the present invention biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between 25 and 37° C. In embodiments, the polymer degrades in a period of between about one hour and several weeks, depending on the desired application.

When used with respect to a payload of the present invention, such as a therapeutic agent or imaging agent, the term "controlled release" (and variants of that term) is intended to mean that the present composition releases the payload over time in contrast to a bolus type administration in which the entire amount of the therapeutic agent is presented to the target at one time. The release will vary in different embodiments of the present invention, and may affect a therapeutic amount, biocompatibility and the like.

The term "$ED_{50}$" means the dose of a therapeutic agent or other material which produces 50% of its maximum response or effect. Alternatively, "$ED_{50}$" means the dose which produces a pre-determined response in 50% of test subjects or preparations. The term "$LD_{50}$" means the dose of a therapeutic agent or other material which is lethal in 50% of test subjects. The term "therapeutic index" refers to the therapeutic index of a therapeutic agent or other material defined as "$ED_{50}/LD_{50}$."

The term "incorporated" or "encapsulated" when used in reference to a payload, therapeutic agent, imaging agent or other material and a composition of the present invention, such as a subject polymeric formulation, denotes incorporating, formulating or otherwise including such agent into a composition which allows for controlled release of such agent in the desired application. The term contemplates any manner by which a payload, agent or other material is incorporated into a subject polymer, including for example: attached to a monomer (by covalent or other binding interaction) and having such monomer be part of the polymerization to give a polymeric formulation, distributed throughout the polymeric formulation, appended to the surface of the polymeric formulation (by covalent or other binding interactions), encapsulated inside the polymeric formulation, etc. The term "co-incorporation" or "co-encapsulation" refers to the incorporation of an agent or other material in a subject composition and at least one or more different agent or other material.

The term "microspheres" refers to substantially spherical colloidal structures having a size ranging from about one or greater up to about 1000 microns. In general, "microcapsules" may be distinguished from microspheres, because microcapsules are generically described as structures in which a substance, such as a polymeric formulation, is covered by a coating of some type. The term "microparticle" may be used to describe structures that may not be readily placed into either of the above two categories or as a generic term for both. If the structures are less than about one micron in diameter, then the corresponding terms "nanosphere," "nanocapsule," and "nanoparticle" may be utilized, but unless otherwise clear from the context will be included within the terms "microsphere," microcapsule "and "microparticle," respectively. In certain embodiments, the nanospheres, nancapsules and nanoparticles have a size of about 500, 200, 100, 50 or 10 nm.

When a large number of microparticles are collected in a subject composition, they may have a variable particle size. In certain embodiments, the particle size distribution may be uniform, e.g., within less than about a 20% standard deviation of the median volume diameter, and in other embodiments, still more uniform or within about 10% of the median volume diameter.

The term "biocompatible plasticizer" refers to any material which is soluble or dispersible in the monomer compositions of the present invention, which increases the flexibility of the resulting polymer film coating on the tissue surface, and which, in the amounts employed, is compatible with the tissue as measured by the lack of moderate to severe tissue irritation. Suitable plasticizers are known in the art and include those disclosed in U.S. Pat. Nos. 6,183,593, 2,784,127 and 4,444,933. Specific plasticizers include, by way of example, acetyl tri-n-butyl citrate, acetyl trihexyl citrate, butyl benzyl phthalate, dibutyl phthalate, dioctylphthalate, n-butyryl tri-n-hexyl citrate, diethylene glycol dibenzoate, and the like. In embodiments, the particular biocompatible plasticizer employed is not critical.

The term "polymerization inhibitor" refers to any material which is soluble or dispersible in the monomer compositions of the present invention and which, in the amounts employed, inhibits the premature polymerization of the composition. In certain embodiments, a polymerization inhibitor is compatible with biological tissue.

The term "cyanoacrylic" as used herein includes cyanoacrylate, cyanoacrylamide, and related compounds, e.g., comprising the structure:

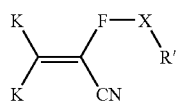

wherein:

K, independently for each occurrence, is a substituted organic residue; X is a heteroatom; R' is a substituted organic residue; and F is a carbon-containing electrophile. In certain embodiments, F is C=O, C=S, or C=NR (with R defined as set forth immediately below). In certain embodiments, K, independently for each occurrence, is H, lower alkyl, lower alkenyl, lower alkynyl, heterocyclyl, or aryl. In certain embodiments, X is O, NR, S, or Se; R is —H, —(CH$_2$)$_n$alkyl, —(CH$_2$)$_n$alkenyl, —(CH$_2$)$_n$alkynyl, —(CH$_2$)$_n$cycloalkyl, —(CH$_2$)$_n$heterocyclyl, —(CH$_2$)$_n$aryl or —(CH$_2$)$_n$heteroaryl; and n is an integer from 0 to 10. In embodiments, X is O, NR or S. In certain embodiments, K, independently for each occurrence, is H, vinyl or aryl. In embodiments, both occurrences of K represent —H. In certain embodiments, R' is one of the following: carbonyl, amino, hydroxyl, sulfhydryl, ether, or thioether functional group bound to a hydrocarbon backbone, such as a chain or ring. In embodiments, R' includes a functional group —XH. In any of the foregoing embodiments, R or K may be substituted or unsubstituted.

The term "delivery agent" refers to a molecule that facilitates the intracellular delivery of a therapeutic agent or imaging agent. Examples of delivery agents include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). In certain embodiments, when the therapeutic agent is a nucleic acid, such as a transgene, the delivery agent may be a viral vector. In such embodiments, the delivery agent comprises a virus or virus particle that has been engineered to contain the nucleic acid. Other delivery agents contemplated by the present invention are discussed in greater detail below.

The term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and doublestranded polynucleotides. Exemplary nucleic acids for use in the subject invention include antisense, decoy molecules, recombinant genes (including transgenes) and the like.

The term "gene" or "recombinant gene" refers to a nucleic acid comprising an open reading frame encoding a polypeptide, including both exonic and (optionally) intronic sequences.

The term "gene construct" refers to a vector, plasmid, viral genome or the like which includes a "coding sequence" for a polypeptide or which is otherwise transcribable to a biologically active RNA (e.g., antisense, decoy, ribozyme, etc), can transfect cells, in certain embodiments mammalian cells, and may cause expression of the coding sequence in cells transfected with the construct. The gene construct may include one or more regulatory elements operably linked to the coding sequence, as well as intronic sequences, poly adenylation sites, origins of replication, marker genes, etc.

The term "genetic immunization" generally refers to the delivery of nucleic acid, including DNA or RNA sequences, to tissues in vivo in order provoke the production of proteins which, if seen by the host as foreign, may induce an immune response.

"Homology" refers to sequence similarity between two peptides or between two nucleic acid molecules. Homology may be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" when describing the relationship between two nucleic acid regions means that they are functionally related to each other. For example, a promoter or other regulatory element is operably linked to a coding sequence of DNA if it controls the transcription of the coding sequence.

The terms "protein," "polypeptide" and "peptide" are used interchangeably when referring to a gene product.

The term "antisense" nucleic acid refers to oligonucleotides which specifically hybridize (e.g., bind) under cellular conditions with a gene sequence, such as at the cellular mRNA and/or genomic DNA level, so as to inhibit expression of that gene, e.g., by inhibiting transcription and/or translation. The binding may be by conventional base pair complementarity, or, for example, in the case of binding to DNA duplexes, through specific interactions in the major groove of the double helix.

The term "host cell" or "target cell" refers to a cell transduced with a specified transfer vector. The cell is optionally selected from in vitro cells such as those derived from cell culture, ex vivo cells, such as those derived from an organism, and in vivo cells, such as those in an organism. "Recombinant host cells" refers to cells which have been transformed or transfected with vectors constructed using recombinant DNA techniques.

The terms "recombinant protein," "heterologous protein" and "exogenous protein" are used interchangeably to refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

"Regulatory element" is a generic term used to refer to nucleotide sequences (such as DNA sequences) that induce or control transcription of protein coding sequences with which they are operably linked. Examples of regulatory elements categorized by function include initiation signals, enhancers, promoters and the like. Exemplary regulatory elements are described in Goeddel, *Methods in Enzymology* 185 (1990). In certain embodiments, transcription of a gene or other DNA is under the control of a promoter sequence (or other regulatory element) which controls the expression of a coding sequence in a cell-type in which expression is intended. A variety of promoters categorized by function are known. The term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a urogenital origin, e.g., renal cells, or cells of a neural origin, e.g., neuronal cells. The term also covers so-called "leaky" promoters, which regulate expression of a selected DNA primarily in one tissue, but cause expression in other tissues as well. The term "inducible" promoter refers to a promoter which is under environmental or developmental regulation. The term "constitutive" promoter refers to a promoter which is active under most environmental and developmental conditions.

Other examples of regulatory elements include the following: the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof.

A "ribozyme sequence" is a catalytic RNA sequence capable of cleaving a target RNA, such as a hairpin or hammerhead ribozyme. The term also encompasses a nucleic acid sequence in an expression cassette from which the RNA is transcribed.

The term "transfection" means the introduction of a nucleic acid, e.g., an expression vector, into a recipient cell, which in certain embodiments may be by nucleic acid-mediated gene transfer. "Transformation," as used with respect to transfected nucleic acid, refers to a process in which a cell's genotype is changed as a result of the cellular uptake of exogenous nucleic acid.

The term "transfer vector" refers to a first nucleic acid molecule to which a second nucleic acid has been linked, and includes for example plasmids, cosmids or phages (as discussed in grater detail below). In certain embodiments of the present invention, the therapeutic agent is the second nucleic acid. One type of transfer vector is an episome, i.e., a nucleic acid capable of extra-chromosomal replication.

In certain embodiments, a transfer vector may be an "expression vector," which refers to a replicable DNA construct used to express DNA which encodes the desired protein and which includes a transcriptional unit comprising an assembly of (i) genetic element(s) having a regulatory role in gene expression, for example, promoters, operators, or enhancers, operatively linked to (ii) a DNA sequence encoding a desired protein which is transcribed into mRNA and translated into protein, and (iii) appropriate transcription and translation initiation and termination sequences. In certain embodiments, the therapeutic agent is the DNA sequence. The choice of promoter and other regulatory elements generally varies according to the intended host cell. In general, expression vectors of utility in recombinant DNA techniques are often in the form of "plasmids," which refer to circular double stranded DNA loops which, in their vector form are not bound to the chromosome. The invention is intended to include such other forms of expression vectors which serve equivalent functions and which become known in the art subsequently hereto.

Certain transfer vectors may contain regulatory elements for controlling transcription or translation, which may be generally derived from mammalian, microbial, viral or insect genes. The ability to replicate in a host, usually conferred by an origin of replication, and a selection gene to facilitate recognition of transformants, may additionally be incorporated.

Transfer vectors derived from viruses, which may be referred to as "viral vectors," may be employed in certain embodiments of the present invention. Some examples include retroviruses, adenoviruses and the like. Viral vectors and their uses in the present invention are discussed in more detail below. As for expression vectors, viral vectors may include regulatory elements.

The design of any transfer vector may depend on such factors as the choice of the host cell to be transformed and/or the type of protein desired to be expressed. Moreover, the vector's copy number, the ability to control that copy number and the expression of any other proteins encoded by the vector, such as antibiotic markers (e.g., ampicillin), may also be considered.

Some examples of expression vectors that may be used in certain embodiments of the present invention include the following. Suitable vectors for expression of polypeptides include plasmids of the types: pBR322-derived plasmids, pEMBL-derived plasmids, pEX-derived plasmids, pBTac-derived plasmids and pUC-derived plasmids for expression in prokaryotic cells, such as *E. coli*. In some instances, it may be desirable to express a protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

"Transgenic animal" is any animal, often a non-human mammal, a bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA.

The term "antimicrobial agent" refers to an agent which inhibits the growth or proliferation of microbes (e.g., bacteria, fungi, yeasts and viruses) thereby inhibiting their development and their pathogenic action. Exemplary such agents are disclosed in PCT Publication No. WO 01/32795. In certain embodiments, the antimicrobial agent may be a small organic molecule, e.g., having a molecular weight less than 2000 amu, or even less than 1000 amu, such as penicillin, tetracycline, erythromycin, etc. In still other embodiments, the antimicrobial agent may be a peptide or protein.

The term "antibody" is intended to include whole antibodies, e.g., of any isotype (IgG, IgA, IgM, IgE, etc.), and to include fragments thereof which are also specifically reactive with a vertebrate, e.g., mammalian, protein. Antibodies may be fragmented using conventional techniques and the fragments screened for utility in the same manner as for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal or other purified preparations of antibodies and recombinant antibodies.

"Humanized" murine antibodies, as the terms are used herein, refer to murine monoclonal antibodies "humanized" by genetically recombining the nucleotide sequence encoding the murine Fv region (i.e., containing the antigen binding site) or the complementarily-determining regions thereof with the nucleotide sequence encoding at least a human constant domain region and an Fc region, e.g., in a manner similar to that disclosed in European Patent Application Publication No. 0,411,893 A3. Some additional murine residues may also be retained within the human variable region framework domains to ensure proper target site binding characteristics. In certain embodiments, humanized antibodies may decrease the immunoreactivity of the antibody or polypeptide in the host recipient, permitting an increase in the half-life and a reduction in the possibility of adverse immune reactions.

An "imaging agent" refers to a composition capable of being used to generate a detectable image, preferably upon binding with a target, and includes without limitation radionuclides (e.g., In-111, Tc-99m, I-123, I-125, F-18, Ga-67, Ga-68) for Positron Emission Tomography (PET) and Single Photon Emission Computer Tomography (SPECT), unpaired spin atoms and free radicals (e.g., Fe, lanthanides, and Gd); and contrast agents (e.g., chelated (DTPA) manganese) for Magnetic Resonance Imaging (MRI). Imaging agents are discussed in greater detail below.

The term "payload" refers to therapeutic agents, imaging agents and/or targeting moieties. In certain embodiments, the payload is preferentially desired to be delivered to a particular site by methods and compositions of the present invention. Where the payload is part of a larger molecule from which it may be releasable, the term payload is to be understood to include the attached form and the free form in accordance with the context, and thus to include, for example, either a bond or an atom(s) (e.g., hydrogen) at one or both ends, depending upon whether it is attached or detached.

"Small molecule" refers to a molecule that has a molecular weight of less than about 2000 amu, or less than about 1000 amu, and even less than about 500 amu.

A "target" shall mean an in vivo site to which a targeted construct binds. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis) and pathogenic fungi (e.g., *Candida* sp.). Certain target infectious organisms include those that are drug resistant (e.g., *Enterobacteriaceae, Enterococcus, Haemophilus influenza, Mycobacterium tuberculosis, Neisseria gonorrhoeae, Plasmodium falciparum, Pseudomonas aeruginosa, Shigella dysenteriae, Staphylococcus aureus, Streptococcus pneumoniae*). In embodiments, a target may refer to a molecular structure to which a targeting moiety binds, such as a hapten, epitope, receptor, dsDNA fragment, carbohydrate or enzyme. Additionally, a target may be a type of tissue, e.g., neuronal tissue, intestinal tissue, pancreatic tissue, etc. Exemplary but non-limiting specific targets are provided below in Tables 1 and 2.

"Target cells" which may serve as targets for methods of this invention include prokaryotes and eukaryotes, including yeasts, plant cells and animal cells. The present method may be used to modify cellular function of living cells in vitro, e.g., in cell culture, or in vivo, in which the cells form part of or otherwise exist in Plant tissue or animal tissue. Thus the cells may form, for example, roots, stalks or leaves of growing plants and the present method may be performed on such plant cells in any manner which promotes contact of the targeted construct with the targeted cells. Alternatively, the target cells may form part of the tissue in an animal. Thus the target cells may include, for example, cells lining the alimentary canal, such as oral and pharyngeal mucosa, cells forming the villi of the small intestine, cells lining the large intestine, cells lining the respiratory system (nasal passages/lungs) of an animal (which may be contacted by inhalation of the subject invention), dermal/epidermal cells, cells of the vagina and rectum, cells of internal organs including cells of the placenta and the so-called blood/brain barrier, etc.

The term "targeting moiety" refers to any molecular structure that assists the construct in localizing to a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, and proteins may serve as targeting moieties.

A "therapeutic agent" shall mean an agent capable of having a desired biological effect on a host, including a therapeutic or prophylactic jointly "therapeutic") effect as discussed above. Certain therapeutic agents are capable of preventing or inhibiting establishment or growth (systemic or local) of a tumor or infection. Examples include boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cis-platin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, photodynamic agents (e.g., rhodamine 123), radionuclides (e.g., I-131, I-125, I-123, Re-186, Re-188, Y-90, Bi-212, At-211, Sr-89, Ho-166, Sm-153, Cu-67 and Cu-64), toxins (e.g., ricin), and transcription-based pharmaceuticals. In certain embodiments for treating or preventing the establishment or growth of a tumor, for example, the therapeutic agent may be a radionuclide, toxin, hormone antagonist, heavy metal complex, oligonucleotide, chemotherapeutic nucleotide, peptide, nonspecific (non-antibody) protein, a boron compound or an enediyne. In certain embodiments for treating or preventing the establishment or growth of a bacterial infection, for example, the therapeutic agent may be an antibiotic, radionuclide or oligonucleotide. In embodiments for treating or preventing the establishment or growth of a viral infection, for example, the therapeutic agent may be an antiviral compound, radionuclide or oligonucleotide. In embodiments for treating or preventing the establishment or growth of a fungal infection, for example, the therapeutic agent may be an antifungal compound, radionuclide or oligonucleotide.

One type of therapeutic agent contemplated by the present invention is a "transgene." A transgene may be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location that differs from that of the natural gene or its insertion results in a knockout). A transgene may also be present in a cell in the form of an episome. A transgene may include one or more regulatory elements and any other nucleic acid, such as introns, that may be necessary for optimal expression of a selected nucleic acid. In certain embodiments, a transgene comprises a nucleic acid sequence of interest and one or more regulatory elements for controlling transcription of the nucleotide sequence encoded by such nucleic acid sequence, e.g., the regulatory element is operably linked to a nucleic acid.

In certain embodiments, the transgene or other therapeutic agent may be a "gene therapy construct," which is an expression vector which may alter the phenotype of a cell when taken up by the cell, or a gene construct. In certain embodiments, the gene therapy construct may be a "recombinant coding sequence" which encodes a polypeptide, or is transcribable to an antisense nucleic acid, a ribozyme, or any other RNA product that alters the phenotype of the cell in which it is produced. "Recombinant gene" refers to a genetic construct including a "recombinant coding sequence."

The term "aliphatic" refers to a linear, branched, and/or cyclic alkane, alkene, or alkyne. In certain embodiments, aliphatic groups in the present invention are linear or branched and have from 1 to about 20 carbon atoms.

The term "alkyl" refers to the radical of saturated aliphatic groups, including straightchain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise in certain embodiments, cycloalkyls may have from about 3 to about 10 carbon atoms in their ring structure, and alternatively about 5, 6 or 7 carbons in the ring structure.

Moreover, the term "alkyl" (or "lower alkyl") includes both "unsubstituted alkyls" and "substituted alkyls", the latter of which refers to alkyl moieties having substituents replacing a hydrogen on one or more carbons. Such substituents may include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the substituents may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls may be further substituted, for example, with alkyls, alkenyls, alkoxys, alkylthios, aminoalkyls, carbonyl-substituted alkyls, —$CF_3$, —CN, and the like.

The term "aralkyl" refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond, respectively.

Unless the number of carbons is otherwise specified, "lower alkyl" refers to an alkyl group, as defined above, but having from one to ten carbons, such as from one to six carbon atoms in its backbone structure. Likewise, "lower alkenyl" and "lower alkynyl" have similar chain lengths.

The term "heteroatom" refers to an atom of any element other than carbon or hydrogen. Illustrative heteroatoms include boron, nitrogen, oxygen, phosphorus, sulfur and selenium.

The term "aryl" includes, for example, 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$—CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, such as 3- to 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" refers to an aromatic or non-aromatic ring in which each atom of the ring is carbon.

The term "nitro" means —NO$_2$; the term "halogen" designates —F, —Cl, —Br or —I; the term "sulfhydryl" means —SH; the term "hydroxyl" means —OH; and the term "sulfonyl" means —SO$_2$.

The terms "amine", "amino" and "ammonium" are art-recognized and refer to both unsubstituted and substituted amines and amine salts, e.g., a moiety that may be represented by the formulae:

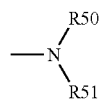 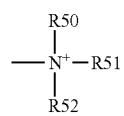

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the formula:

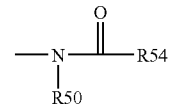

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the formula:

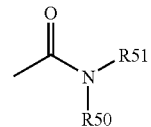

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art recognized and includes such moieties as may be represented by the formulae:

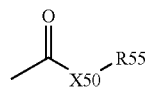 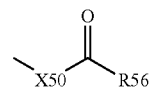

wherein X50 is a bond or represents an oxygen or a sulfur, and R55 and R56 represent hydrogen, alkyl, alkenyl, —(CH$_2$)$_m$—R61 or pharmaceutically acceptable salt, where m and R61 are defined above. Where X50 is an oxygen and R55 or R56 is not hydrogen, the formula represents an "ester." Where X50 is an oxygen, and R55 is as defined above, the moiety is referred to herein as a carboxyl group, and particularly when R55 is a hydrogen, the formula represents a "carboxylic acid." Where X50 is an oxygen, and R56 is hydrogen, the formula represents a "formate." In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" refer to an alkyl group, as defined above, having an oxygen radical attached thereto. Representative alkoxy groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—R61, where m and R61 are described above.

The term "sulfonate" is art recognized and includes a moiety that may be represented by the formula:

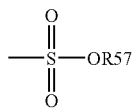

in which R57 is an electron pair, hydrogen, alkyl, cycloalkyl, or aryl.

The term "sulfate" is art recognized and includes a moiety that may be represented by the formula:

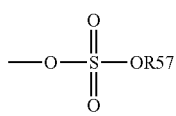

in which R57 is as defined above.

The term "sulfonamido" is art recognized and includes a moiety that may be represented by the formula:

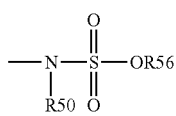

in which R50 and R56 are as defined above.

The term "sulfamoyl" is art-recognized and includes a moiety that may be represented by the formula:

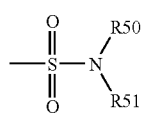

in which R50 and R51 are as defined above.

The term "sulfonyl" refers to a moiety that may be represented by the formula:

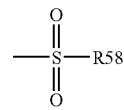

in which R58 is one of the following: hydrogen, alkyl, alkenyl, alkynyl, cycloalkyl, heterocyclyl, aryl or heteroaryl.

The term "sulfoxido" refers to a moiety that may be represented by the formula:

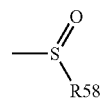

in which R58 is defined above.

A "phosphoryl" may in general be represented by the formula:

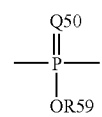

wherein Q50 represents S or O, and R59 represents hydrogen, a lower alkyl or an aryl. When used to substitute, e.g., an alkyl, the phosphoryl group of the phosphorylalkyl may be represented by the formulae:

wherein Q50 and R59, each independently, are defined above, and Q51 represents O, S or N. When Q50 is S, the phosphoryl moiety is a "phosphorothioate".

A "phosphoramidite" may be represented by the formulae:

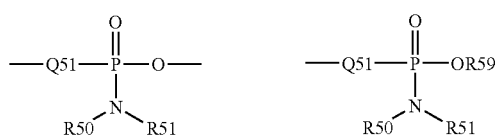

wherein Q51, R50, R51 and R59 are as defined above.

A "phosphonamidite" may be represented by the formulae:

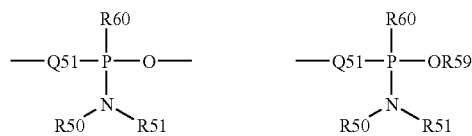

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The selection of each expression, e.g. alkyl, m, n, etc., when it occurs more than once in any structure, is intended to be independent of the selection of an embodiment of that expression elsewhere in the same structure.

A "selenoalkyl" refers to an alkyl group having a substituted seleno group attached thereto. Exemplary "selenoethers" that may be substituted on the alkyl are selected from —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methane sulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain monomeric subunits of the present invention may exist in particular geometric or stereoisomeric forms. In addition, polymers of the present invention may also be optically active. The present invention contemplates all such compounds, including cis- and transisomers, R- and S-enantiomers, diastereomers, (D)-isomers, (L)-isomers, racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds that may be substituted or unsubstituted.

By the terms "amino acid residue" and "peptide residue" are meant an amino acid or peptide molecule by which either the carboxy or amino terminus, or both, form a bond to another organic residue, such as, for example, an amide bond formed with another amino acid residue. In general the abbreviations used herein for designating the amino acids and the protective groups are based on recommendations of the IUPAC-IUB Commission on Biochemical Nomenclature (see Biochemistry (1972) 11:1726-1732). For instance Met, Ile, Leu, Ala and Gly represent "residues" of methionine, isoleucine, leucine, alanine and glycine, respectively. In that example, residue is meant a radical derived from the corresponding α-amino acid by eliminating the OH portion of the carboxyl group and the H portion of the α-amino group. The term "amino acid side chain" is that part of an amino acid exclusive of the —CH(NH$_2$)COOH portion, as defined by K. D. Kopple, "Peptides and Amino Acids", W. A. Benjamin Inc., New York and Amsterdam, 1966, pages 2 and 33; examples of such side chains of the common amino acids are —CH$_2$CH$_2$SCH$_3$ (the side chain of methionine), —CH$_2$(CH$_3$)—CH$_2$CH$_3$ (the side chain of isoleucine), —CH$_2$CH(CH$_3$)$_2$ (the side chain of leucine) or H-(the side chain of glycine).

In certain embodiments, the amino acids used in the application of this invention are naturally occurring amino acids found in proteins, or naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan, and those amino acids and amino acid analogs that have been identified as constituents of peptidylglycan bacterial cell walls.

The term "amino acid residue" further includes analogs, derivatives and congeners of amino acids, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups. For instance, the subject compound may include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein may be designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers may be obtained in substantially pure form by classical separation techniques and by sterically controlled synthesis. For the purposes of this application, unless expressly noted to the contrary, a named amino acid shall be construed to include both the (D) or (L) stereoisomers. In the majority of cases, D- and L-amino acids have R- and S-absolute configurations, respectively. The names of the natural amino acids are abbreviated herein in accordance with the recommendations of IUPAC-IUB.

Also included are "reversed" or "retro" peptide sequences, which refer to that part of an overall sequence of covalently-bonded amino acid residues (or analogs or mimetics thereof) wherein the normal carboxyl-to-amino direction of peptide bond formation in the amino acid backbone has been reversed such that, reading in the conventional left-to-right direction, the amino portion of the peptide bond precedes (rather than follows) the carbonyl portion. See, generally, Goodman, M. and Chorev, M., Accounts of Chem. Res. 1979, 12, 423.

The reversed orientation peptides described herein include (a) those wherein one or more amino-terminal residues are converted to a reversed ("rev") orientation (thus yielding a second "carboxyl terminus" at the left-most portion of the moiety), and (b) those wherein one or more carboxyl-terminal residues are converted to a reversed ("rev") orientation (yielding a second "amino terminus" at the right-most portion of the moiety). A peptide (amide) bond cannot be formed at the interface between a normal orientation residue and a reverse orientation residue.

Therefore, certain reversed peptide compounds of the invention can be formed by utilizing an appropriate amino acid mimetic moiety to link the two adjacent portions of the sequences depicted above utilizing a reversed peptide (reversed amide) bond. In case (a) above, a central residue of a diketo compound may conveniently be utilized to link structures with two amide bonds to achieve a peptidomimetic structure. In case (b) above, a central residue of a diamino compound will likewise be useful to link structures with two amide bonds to form a peptidomimetic structure.

The phrase "protecting group" includes temporary substituents that protect a potentially reactive functional group from undesired chemical transformations. Examples of such protecting groups include without limitation esters of carboxylic acids, silyl ethers of alcohols, and acetals and ketals of aldehydes and ketones, respectively. The field of protecting group chemistry has been reviewed. Greene and Wuts *Protective Groups in Organic Synthesis* ($2^{nd}$ ed., Wiley: New York, 1991).

The phrase "hydroxyl-protecting group" refers to those groups intended to protect a hydroxyl group against undesirable reactions during synthetic procedures and includes, for example, benzyl or other suitable ester or ether groups known in the art.

The term "electron-withdrawing group" is recognized in the art, and denotes the tendency of a substituent to attract valence electrons from neighboring atoms, i.e., the substituent is electronegative with respect to neighboring atoms. A quantification of the level of electronwithdrawing capability is given by the Hammett sigma ($\sigma$) constant. This well known constant is described in many references, for instance, March, *Advanced Organic Chemistry* 251-59 (McGraw Hill Book Company: New York, 1977). Hammett constant values are generally negative for electron donating groups ($\sigma(P)=-0.66$ for $NH_2$) and positive for electron withdrawing groups ($\sigma(P)=0.78$ for a nitro group), (&&&(P)

indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein. For example, the term "substituted organic residue" is intended to refer any organic moiety that has substitutions like those described above. Permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

III. Exemplary Compositions of the Present Invention and Methods of Preparation Thereof A. Compositions 1. Monomers In certain embodiments, a chemical moiety of the present invention has the structure of Formula I:

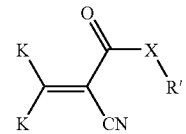

wherein:

K, independently for each occurrence, is H, lower alkyl, lower alkenyl, lower alkynyl, heterocyclyl, or aryl;

X is O, NR, S or Se;

R is absent —H, —$(CH_2)_n$alkyl, —$(CH_2)_n$alkenyl, —$(CH_2)_n$alkynyl, —$(CH_2)_n$cycloalkyl, $(CH_2)_n$heterocyclyl, —$(CH_2)_n$aryl or —$(CH_2)_n$heteroaryl;

n is an integer from 0 to 10; and

R' is a substituted organic residue.

In certain embodiments, X is an O, NR or S. In certain embodiments, K, independently for each occurrence, is H, vinyl or aryl. In embodiments, both occurrences of K are H. In certain embodiments, R' is one of the following: carbonyl, amino, hydroxyl, sulfhydryl, ether, or thioether functional group bound to a hydrocarbon backbone, such as a chain or ring. In embodiments, R' includes a functional group —XH. In any of the foregoing embodiments, R or K may be substituted or unsubstituted. In still other embodiments, [R'—X] includes, for example, one or more of the following: an amino acid residue, a payload, or a branched polyfunctional group.

In certain embodiments, a monomer of the present invention has the structure of Formula II:

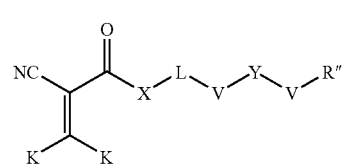

wherein:

K, X, R, and n are as defined above, each independently for each occurrence;

L is absent or is —(CH$_2$)$_n$alkyl-, —(CH$_2$)$_n$alkenyl-, —(CH$_2$)$_n$alkynyl-, —(CH$_2$)$_n$O(CH$_2$)p-, —(CH$_2$)$_n$NR(CH2)p-, —(CH$_2$)$_n$S(CH2)$_p$—, —(CH$_2$)$_n$alkyl(CH$_2$)$_p$—, —(CH$_2$)$_n$alkenyl(CH$_2$)$_p$—, (CH$_2$)$_n$alkynyl(CH$_2$)$_p$—, —O(CH$_2$)$_n$—, —NR(CH$_2$)$_n$—, or —S(CH$_2$)$_n$—;

p is an integer from 0 to 10;

Y is absent or is C=O, SO$_2$, SO or C=S;

V, independently for each occurrence, is absent or is NR, O, S or Se; and

R'' is a substituted organic residue.

In certain embodiments wherein Y is absent, at least one occurrence of V may be absent. In other embodiments wherein L is absent, the adjacent occurrence of V may be absent.

In certain embodiments, the moiety [R'—X] includes, for example, one or more of the following: an amino acid residue, a payload or a branched polyfunctional group. For example, the [R'—X] residue may include an amino acid residue, e.g., —NR—CH(Z)—CO—, wherein Z represents —H or a substituted or unsubstituted alkyl, alkenyl, alkynyl, aryl, or heterocyclyl moiety, and R and —CH(Z), taken together, optionally form a ring, e.g., having from 5 to 7 members, including N, R, C and Z. In various embodiments, X may represent the amine of the amino acid, a heteroatom bound to the carbonyl of the amino acid (e.g., to form an imide or anhydride), or may represent a heteroatom in the Z substituent. For example, the amino acids serine, tyrosine, and threonine each includes hydroxyl groups on the Z substituent, and these hydroxyl groups may be coupled to the carbonyl of the cyanoacrylic core. The amino acid cysteine has a sulfhydryl group on the Z substituent which may be coupled to the cyanoacrylic core to form a thioester. Lysine, tryptophan and histidine each has an amino group on the Z substituent which may be used to form an amide with the cyanoacrylic core. Glutamic acid and aspartic acid each has a carboxyl group on the Z side chains which may be used to form an anhydride with the cyanoacrylic core. Glutamine has an amide group on its side chain, which may form an imide with the cyanoacrylic core. Other amino acids with heteroatomic substituents on the Z side chain may be coupled to the cyanoacrylic core. In certain embodiments, Z represents the side chain of a naturally occurring amino acid.

The choice of X and R' will generally determine the relative strength of the bond between the R' group and the cyanoacrylic core. For example, bond strength will generally vary in the order amide>ester=imide>thioester>anhydride. Thus, by selecting the nature of the linkage, the relative physiological stability of the polymer may be modified, the rate of release of a biologically active R' may be varied, etc. One of ordinary skill in the art will recognize, however, that the above hierarchy is only approximate, and may be altered by the particular steric and electronic characteristics of a particular linkage. For example, a bond between the core and the nitrogen of the imidazole ring of histidine may be as weak or weaker than an anhydride, and may vary with the pH of the surrounding medium. Similarly, an ester linkage to tyrosine is likely to be weaker than an ester linkage to serine or threonine, because a phenol has lower electron density than an ordinary hydroxyl, and an ester linkage to threonine may be more stable than an ester linkage to serine because of steric hindrance. Using these well-known principles, a linkage may be selected to provide a suitably stable bond to the polymer backbone, or to modulate the rate of release or breakdown of the [R'—X]-core linkage.

Thus, in certain embodiments, a cyanoacrylic monomer of the present invention has a structure of Formulae III-VIII:

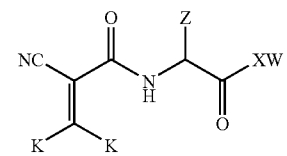

III

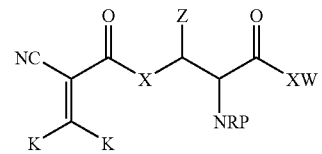

IV

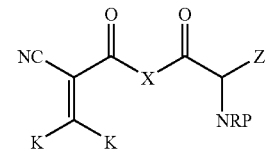

V

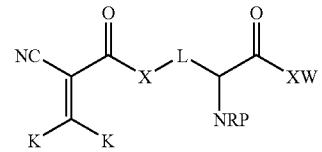

VI

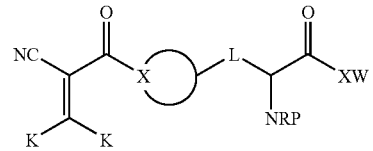

VII

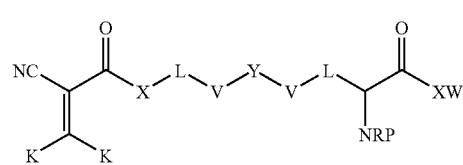

VIII wherein:

K, Y, L, R', n, p, V, and X are as defined above, each independently for each occurrence;

P, independently for each occurrence, is H, lower alkyl or a nitrogen-protecting group;

W, independently for each occurrence, is —(CH$_2$)$_n$alkyl, —(CH$_2$)$_n$alkenyl, —(CH$_2$)$_n$alkynyl, —(CH$_2$)$_n$cycloalkyl, —(CH$_2$)$_n$heterocyclyl, —(CH$_2$)$_n$aryl or —(CH$_2$)$_n$heteroaryl, one or more amino acid residues, or a payload; and Z, independently for each occurrence, is H or a substituted or unsubstituted alkyl, alkenyl, alkynyl, cycloalkyl, aralkyl, aryl, or heterocyclyl.

In certain embodiments, W maybe substituted or unsubstituted. In certain embodiments, in which P is a nitrogen protecting group, such group is alkenyl, aralkyl, acyl, alkyloxycarbonyl, aralkyloxycarbonyl, alkenyloxycarbonyl, silyl, arylsulfonyl, alkylsulfonyl or the like.

Generally, and especially for compositions wherein the cyanoacrylic core is conjugated to a small number of amino acids, e.g., 1-3 amino acids, the choice of amino acids may profoundly affect the properties of the monomer and any polymer that results therefrom. For example, use of hydrophilic amino acids such as serine and histidine may give rise to a polymer which is substantially hydrophilic, e.g., may absorb water or dissolve in water. Alternatively, use of amino acids with large hydrophobic groups, such as phenylalanine and leucine, may provide a polymer which is substantially hydrophobic, e.g., is substantially water-proof or is immiscible with aqueous solvents. Amino acids with small hydrophobic groups, such as glycine and alanine, may result in a polymer with intermediate characteristics. Thus, the range of natural amino acids permits access to polymers with a range of properties. Further modification and gradation may be obtainable by using a mixture of monomers bearing different amino acids, conjugating two or more different amino acids to each monomer subunit, or by other techniques which will be apparent to those of skill in the art.

In certain embodiments, W or R' may represent a branched, polyfunctionalized alkyl group (e.g., having at least two branches, each of which bears a functional group), such as

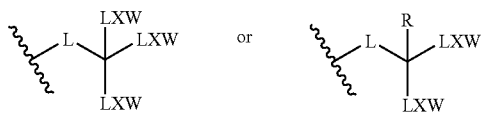

wherein L, X, W, and R are as defined above, each independently for each occurrence. In certain embodiments, L is a C1-C3 alkylene. In certain embodiments, R is H or lower alkyl, such as methyl. In certain embodiments, X is selected from NR and O. In certain embodiments, W may be H, lower alkyl or a polyether, such as poly(ethylene glycol).

In certain embodiments, R' or W comprises a payload, e.g., a therapeutic agent, an imaging agent and/or a targeting moiety, or the polymer may include more than one payload, e.g., a therapeutic agent and an imaging agent, two or more different therapeutic agents, etc. In certain embodiments, R' or W comprises a targeting moiety. In certain embodiments, a subject polymer may be a copolymer derived from monomers which include targeting moieties and monomers which include another payload. In embodiments, a subject polymer may include a polymer derived from monomers which include targeting moieties and a polymer derived from monomers which include another payload. In certain embodiments, R' and W are selected to be compatible with formation of the cyanoacrylic core present in the polymer including such monomer, e.g., R' does not substantially promote or hinder polymerization of the monomer, or R' does not substantially inhibit or reduce desirable properties of the polymer, etc. The nature of payloads is described in greater detail elsewhere herein.

2. Polymers

A polymer formed from cyanoacrylic monomers will generally result from the following generic transformation:

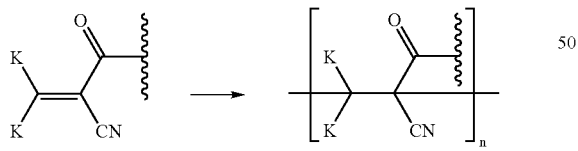

Thus, a polymer prepared from a monomer of Formula I would include at least two or more subunits covalently bonded together in a series having the following structure:

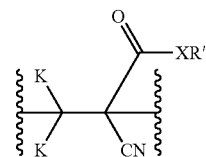

A polymer prepared from a monomer of Formula II would include at least two or more subunits having the following structure:

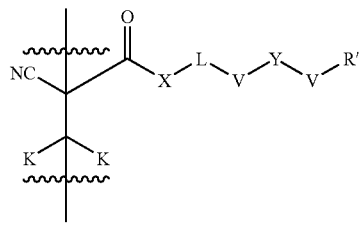

Polymers prepared from monomers of Formulae III-VIII would include at least two or more subunits having the structures of Formulae IIIp-VIIIp, respectively:

IIIp

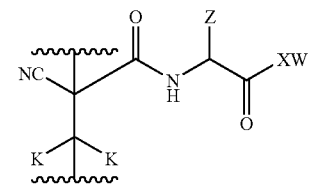

IVp

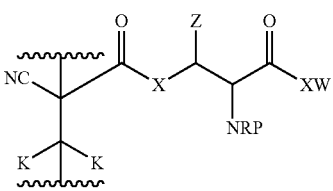

Vp

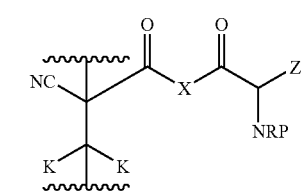

VIp

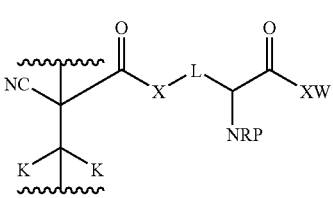

VIIp

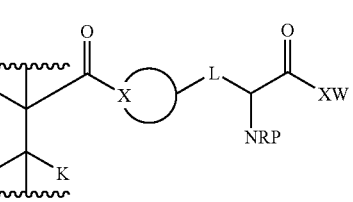

VIIIp

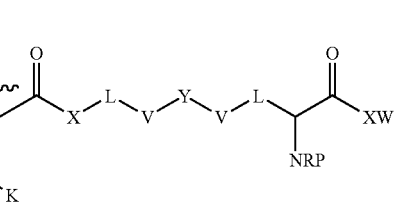

For any of the polymers prepared from the monomers as described above, it is not necessary that all of any such monomers in a sample polymerize to form the subject polymers. Indeed, in certain embodiments, the monomer may polymerize with other monomers and polymers to form the subject polymers, as indicated in the above diagrams, or in the alternative, monomers and polymers may undergo so-called side reactions that, for example, either terminate a polymer chain or preclude a monomer from reacting with a polymer chain to extend that chain. For many of the subject polymers, and their uses described herein, the degree of polymerization of the monomer required is only that necessary to provide a polymer with the properties, both chemical and physical, to satisfy the use to which the polymer is put. For example, as discussed in greater detail below, when a polymer is used as a biocompatible adhesive, the degree of polymerization of the monomers into the biocompatible polymer need only be that amount of polymerization necessary to give a suitable adhesive for the particular application. In certain embodiments, the monomers need only be substantially polymerized.

Any polymer prepared from such monomers may include from about 4, 7, 10, 15, 25, 50 100 or greater such subunits covalently bonded together in a series.

The present compositions may include mixtures of monomers disclosed herein. For example, a monomer having one therapeutic agent as a payload and a second monomer with a different payload that is not a therapeutic agent could be formulated together and copolymerized to give a polymer with a mixture of such monomers. In this fashion, for example, it would be possible to adjust the controlled release rate of the therapeutic agent and thereby the dosing of such polymeric formulation.

In certain embodiments, at least about 10 percent to 100 percent of any subject polymer may be composed of monomeric elements having the structures depicted by the formulae herein. In exemplary embodiments of the present invention, at least about 25, 50, 75, 85, 90 or 95 percent of the polymer may be composed of such repetitive elements. For example, for a polymer having units depicted in Formula I, at least about 10 percent to 100 percent of the polymer may be composed of monomeric elements having the structures depicted by such formula, or at least about 25, 50, 75, 85, 90 or 95 percent of the polymer may be composed of such repetitive subunits. Other monomeric units that do not have the formulae set forth herein would need to be compatible with the polymerization chemistry if such other units were to be incorporated into the polymer in which the monomers of the present invention are included. As a general matter, such other monomeric units would have the cyanoacrylic core.

In embodiments, polymers of the present invention may be mixed or blended with other polymers. In certain embodiments, the other polymers are biocompatible and/or biodegradable themselves. Some non-limiting examples of such polymers include poly(alkylene glycol), e.g., having a molecular weight between 500 and 20,000 amu, a polysaccharide, poly(lactic-co-glycolic acid), poly(lactic acid), poly(glycolic acid) polyanhydride, polyphosphazene, polycaprolactone or other biodegradable and/or biocompatible polymers.

In certain embodiments, substituents of the polymeric chain, such as R' or K, may be selected to permit additional inter-chain cross-linking by covalent or electrostatic (including hydrogen-binding or the formation of salt bridges), e.g., by the use of an organic residue appropriately substituted. A variety of means of achieving cross-linking of the subject polymers are discussed in detail below.

In any of the subject polymers, a variety of materials may be incorporated. Examples of such materials, which are discussed in greater detail below, include therapeutic and imaging agents, additives, inhibitors, stabilizers, formaldehyde concentration reducing agents, fillers, thickening agents, cross-linking agents, initiators, and the like. These other materials are in addition to any payload that is covalently attached or otherwise bound to the monomers that are included in the subject polymers. In certain aspects, the present invention contemplates loading more than two different substances into any polymer matrix. In certain embodiments, three, four, five or more such materials may be incorporated or associated with any polymer matrix.

Such materials may be incorporated by polymerizing subject monomers (and like compounds) with the material to be incorporated being present in the mixture. Alternatively, depending on the nature of the ensuing polymeric formulation, materials may be blended or integrated into the polymer during, substantially after or upon completion of polymerization.

For example, therapeutic agents may be formulated in the subject polymer compositions. In certain embodiments, the therapeutic agent is mixed with the monomer(s) from which the subject polymer is formed. For example, the co-encapsulation of one or more cytokines, such as IFN-γ and IL-4, may affect the immunogenic response afforded any nucleic acid that is incorporated into the polymer matrix as a payload. The amount of any such therapeutic agent to be loaded into any polymer matrix will depend on a variety of factors, including the nature of the therapeutic agent, the polymer matrix, whether there are any other materials incorporated, and the like. For any therapeutic agent, the present invention contemplates incorporating a therapeutically effective amount of such agent. In embodiments, for example, the amount of such therapeutic agent may range from below or about 0.005% up to about 40% or higher, for example, 0.01, 0.05, 0.1, 0.25, 0.5, 1.0, 2.5, 5.0, 10, 15, 20, 25, 30, or 35%. For example, a therapeutic agent loaded at a 2% level means that there is 2 mg of such agent per 100 mg of polymer matrix. Subject polymers with more hydrophobic character may be selected to encapsulate hydrophobic agents, and hydrophilic polymers may be used with hydrophilic agents, thereby improving the solubility of the compound in the polymer.

In embodiments, the monomer may be combined with a plasticizer, e.g., which would be present in the resulting polymer and modify the properties thereof. Suitable plasticizers and amounts thereof are disclosed in U.S. Pat. No. 6,183,593 to Narang et al. Plasticizers have also been added to cyanoacrylic surgical adhesive compositions, e.g., at from about 10 to 30 weight percent and in other embodiments at from about 18 to 25 weight percent based on the total weight of the composition. See, for example, U.S. Pat. No. 3,759,264 to Coover, Jr. et al., U.S. Pat. No. 3,667,472 to Halpern, U.S. Pat. No. 3,559,652 to Banitt.

Additives may optionally be used to modify the cure rate and/or shelf life of the subject polymers. For example, cyanoacrylic polymerization inhibitors or stabilizers including Lewis acids, such as sulfur dioxide, nitric oxide, boron trifluoride and other acidic substances or free-radical inhibitors, including hydroquinone monomethyl ether, hydroquinone, nitrohydroquinone, catechol and hydroquinone monoethyl ether. See, for example, U.S. Pat. No. 3,559,652. Preferred polymerization inhibitors and stabilizers are disclosed in U.S. Pat. No. 6,183,593 to Narang et al. Other preferred polymerization inhibitors include glacial acetic acid, free radical inhibitors (e.g., hydroquinones) and the like which may be used alone or in combination with 4-methoxyphenol and/or $SO_2$.

In one embodiment the inhibitor is sulfur dioxide which may, for example, be employed at from about 50 to 1000 ppm, in embodiments from 100 to 500 ppm, based on the total weight of the composition. In another embodiment, the inhibitor is 4-methoxyphenol which is employed at from about 50 to 1000 ppm, in other embodiments from 100 to 500 ppm, based on the weight of the composition. In certain embodiments, substantial amounts of stabilizer may be useful to inhibit premature polymerization of the monomer, e.g., if the cyanoacrylic monomer is impure or includes a mildly nucleophilic moiety which promotes polymerization.

Compositions of this invention may include a biocompatible agent effective to reduce active formaldehyde concentration levels, or "formaldehyde concentration reducing agents". Formaldehyde, as indicated below, is a potential byproduct of the any subject polymers of the present invention during their degradation, including their biodegradation in vivo. In certain examples, such an agent is a formaldehyde scavenger, which generally operates by reacting with formaldehyde to form an organic product that is more desirable than formaldehyde itself because, for example, it is less reactive or more biocompatible. Examples of formaldehyde scavengers useful in this invention include those disclosed in U.S. Pat. Nos. 5,328,687 and 5,624,669, such as sulfites; bisulfites; mixtures of sulfites and bisulfites; ammonium sulfite salts; amines; amides; imides; nitriles; carbamates; alcohols; mercaptans; proteins; mixtures of amines, amides, and proteins; active methylene compounds such as cyclic ketones and compounds having a beta-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom.

Bisulfites and sulfites useful as the formaldehyde scavenger compound in this invention include alkali metal salts such as lithium, sodium and potassium salts, and ammonium salts, for example, sodium bisulfite, potassium bisulfite, lithium bisulfite, ammonium bisulfite, sodium sulfite, potassium sulfite, lithium sulfite, ammonium sulfite, and the like.

Examples of amines useful in this invention include the aliphatic and aromatic amines such as, for example, aniline, benzidine, aminopyrimidine, toluene-diamine, triethylenediamine, diphenylamine, diaminodiphenylamine, hydrazines and hydrazide. Suitable proteins include collagen, gelatin, casein, soyabean protein, vegetable protein, keratin and glue.

Suitable amides for use in this invention include urea, cyanamide, acrylamide, benzamide, and acetamide. Suitable alcohols include phenols, 1,4-butanediol, d-sorbitol, and polyvinyl alcohol. Examples of suitable compounds having a beta-dicarbonyl group include malonic acid, acetylacetone, ethylacetone, acetate, malonamide, diethylmalonate or another malonic ester. In particular embodiments, cyclic ketones that may be used in this invention include cyclohexanone and cyclopentanone.

Examples of suitable heterocyclic compounds for use as formaldehyde scavenger in this invention are disclosed, for example, in U.S. Pat. No. 4,127,382 to Perry. Such heterocyclic compounds include, for example, benzimidazole, S-methyl benzimidazole, 2-methylbenzimidazole, indole, pyrrole, 1,2,4-triazole, indoline, benzotriazole, indoline, and the like.

In practicing certain embodiments of this invention, the formaldehyde concentration reducing agent, often a formaldehyde scavenger, is added in an sufficient amount to the cyanoacrylate polymer, whereby an sufficient amount is that amount sufficient to reduce the amount of formaldehyde generated during subsequent in vivo biodegradation of the polymerized cyanoacrylate. In certain embodiments, the sufficient amount is that amount which reduces the formaldehyde concentration to a level so that the polymer remains biocompatible while in use in vivo. This amount will depend on the type of active formaldehyde concentration reducing agent, and can be readily determined without undue experimentation by those skilled in the art.

The formaldehyde concentration reducing agent may be used in this invention in either free form or in microencapsulated form. When microencapsulated, the formaldehyde concentration reducing agent is released from the microcapsule continuously over a period of time during the in vivo biodegradation of the cyanoacrylate polymer. In certain embodiments, the microencapsulated form of the formaldehyde concentration reducing agent is preferred to prevent or reduce polymerization of the cyanoacrylate monomer by the formaldehyde concentration reducing agent, thereby increasing shelf-life and facilitating handling of the monomer composition during use.

Microencapsulation of the formaldehyde scavenger may be achieved by many known microencapsulation techniques. For example, microencapsulation may be carried out by dissolving a coating polymer in a volatile solvent, e.g., methylene chloride, to a polymer concentration of about 6% by weight; adding a formaldehyde concentration reducing agent in particulate form to the coating polymer/solvent solution under agitation to yield a formaldehyde concentration reducing agent concentration of about 18% by weight; slowly adding a surfactant-containing mineral oil solution to the polymer solution under rapid agitation; allowing the volatile solvent to evaporate under agitation; removing the agitator; separating the solids from the mineral oil; and washing and drying the microparticles. The size of the microparticles will range from about 0.001 to about 1000 microns.

In certain embodiments, the coating polymer for microencapsulating the formaldehyde concentration reducing agent is chosen so that the polymer undergoes in vivo bioerosion, and in certain embodiments such bioerosion occurs at rates similar to or greater than the cyanoacrylate polymer formed by the monomer. Such bioerosion may occur as a result of the physical or chemical breakdown of the encapsulating material, for example, by the encapsulating material passing from solid to solute in the presence of body fluids, or by biodegradation of the encapsulating material by agents present in the body.

Examples of coating materials which may be used to microencapsulate the formaldehyde concentration reducing agent include polyesters, such as polyglycolic acid, polylactic acid, copolymers of polyglycolic acid and polylactic acid, polycaprolactone, poly-$\beta$-hydroxybutyrate, copolymers of epsilon-caprolactone and delta-valerolactone, copolymers of epsilon-caprolactone and DL-dilactide, and polyester hydrogels; polyvinylpyrrolidone; polyamides; gelatin; albumin; proteins; collagen; poly(orthoesters); poly (anhydrides); poly(alkyl-2-cyanoacrylates); poly(dihydropyrans); poly(acetals); poly(phosphazenes); poly(urethanes); poly(dioxinones); cellulose; and starches.

A composition of this invention may contain one or more adjuvant substances, such as fillers, thickening agents or the like. In embodiments, materials that serve as adjuvants may be associated with the polymer matrix. Such materials may affect the characteristics of the polymer matrix that results. For example, fillers, such as bovine serum albumin (BSA) or mouse serum albumin (MSA), may be associated with the polymer matrix. In certain embodiments, the amount of filler may range from about 0.1 to about 50% or more by weight of the polymer matrix, or about 2.5, 5, 10, 25, 40 percent. Incorporation of such fillers may affect the biodegradation of the polymeric material and the controlled release rate of any payload. Other fillers known to those of skill in the art, such as carbohydrates, sugars, saccharides, and polysaccharides, including mannitose and sucrose, may be used in certain embodiments in the present invention.

Suitable thickeners include, for example, fumed silica, polycyanoacrylics, polylactic acid, polyglycolic acid, lactic-glycolic acid copolymers, polycaprolactone, lactic acid-caprolactone copolymers, poly-3-hydroxybutyric acid, poly-orthoesters, polyalkyl acrylates, copolymers of alkylacrylate and vinyl acetate, polyalkyl methacrylates (e.g., polymethylmethacrylate (PMMA)), and copolymers of alkyl methacrylates and butadiene. Fumed silica is particularly useful in producing a gel for topical application having a viscosity of from about 1500 to 50,000 centipoise at 20° C. Suitable thickening agents for the compositions described herein also include a partial polymer of the cyanoacrylic as analogously disclosed in U.S. Pat. No. 5,981,621 to Clark et al., U.S. Pat. No. 6,010,714 to Leung et al., U.S. Pat. No. 6,143,805 to Hickey et al., U.S. Pat. Nos. 3,654,239 and 4,038,345 and PCT Publication WO 01/12243. Thickening agents for topical application are deemed to be biocompatible if they are soluble or dispersible in the composition and are compatible with the skin as measured by the lack of moderate to severe skin irritation.

The specific viscosity of these compositions depends, in part, on the intended application of the composition. For example, relatively low viscosities are often preferred where application is to be made to a large surface area. This preference results from the fact that those forms are less viscous and, accordingly, may permit more facile large surface area application of a thin layer. Contrarily, when application is to be made to a specific position on the skin (e.g., elbow surfaces), higher viscosity compositions, including those containing thixotropic materials, are preferred to prevent "running" of the material to unintended locations.

In embodiments, the adhesive composition has a viscosity of about 1-5000 centipoise, preferably 1-600 centipoise, more preferably 1-100 or 2-50 centipoise such as 2-18, 2-10 or 5-7 centipoise, or 30-500 such as 50-100 or 100-200 centipoise at 25° C. The viscosity can be selected according to the proposed use—e.g., 1-100 centipoise for certain uses and 100-200 centipoise for other uses. Additionally, the composition may be a gel, e.g., 50,000-500,000 centipoise at 25° C. The viscosity of the adhesive composition can be measured with a Brookfield Viscometer. Additionally, in embodiments where a sterilization treatment is applied, the viscosity of the composition should preferably be maintained or increased by a controlled and acceptable amount after sterilization.

To improve the cohesive strength of adhesives formed from the compositions of this invention, difunctional monomeric cross-linking agents may be added to the monomer compositions of this invention. Such cross-linking agents are known. Reference is made, for example, to U.S. Pat. No. 3,940,362 to Overhults. Examples of suitable cross-linking agents include triallyl isocyanurates, alkylene diacrylates, alkylene dimethacrylates, trimethylol propane triacrylate, alkyl bis(2-cyanoacrylates) (e.g., as described in U.S. Pat. No. 4,041,061), allyl 2-cyanoacrylates (U.S. Pat. No. 4,134,929), subunits which bear at least two cyanoacryloyl moieties, etc. A catalytic amount of an amine-activated free radical initiator may be added to initiate polymerization of the cyanoacrylic monomer/cross-linking agent blend.

The present compositions may additionally contain one or more optional additives such as fibrous reinforcement, colorants, perfumes, rubber modifiers, modifying agents, etc. In practice, each of these optional additives should be both miscible and compatible with the cyanoacrylic monomer composition and the resulting polymer. Compatible additives are those that do not prevent the use of the cyanoacrylics in the manner described herein. Examples of suitable fibrous reinforcement include PGA microfibrils, collagen microfibrils, cellulosic microfibrils, and olefinic microfibrils. In general, colorants are added so that the polymer layer formed on the skin will contain a discrete and discernable color. In some cases, the colorant may be used to mask the polymer layer over the skin thereby minimizing the patient's sensitivity to the placement of such films on the skin. Examples of suitable colorants include 1-hydroxy-4-[4 methylphenyl-amino]-9,10-anthracenedione (FD+C violet No. 2); disodium salt of 6-hydroxy-5-[(4-sulfophenyl)azo]-2-naphthalene-sulfonic acid (FD+C Yellow No. 6); 9-(o-carboxyphenyl)-6-hydroxy-2,4,5,7-tetraiodo-3H-xanthen-3-one, disodium salt, monohydrate (FD+C Red No. 3); 2-(1, 3-dihydro-3-oxo-5-sulfo-2H-indol-2-ylidene)-2,3-dihydro-3-oxo-1H-indole-5-sulfonic acid disodium salt (FD+C Blue No. 2); and [phthalocyaninato($2^-$)] copper. Perfumes may be added to mask an unpleasant smell and/or provide a pleasant smell to the formulation. Rubber modifiers may be added to further enhance the flexibility of the resulting polymer layer. The amount of each of these optional additives employed in the composition is an amount necessary to achieve the desired effect.

Polymerization of the subject monomers to form polymers may be catalyzed by a variety of means and agents. In many applications using compositions of this invention, polymerization of the monomers is catalyzed by small amounts of moisture. For example, application of the subject monomers to tissue catalyzes formation of the desired polymer.

In embodiments of the present invention, the composition and/or its applicator may contain materials such as a polymerization initiator, accelerator, rate-modifier, and/or cross-linking agent for initiating polymerization and/or cross-linking of the polymerizable monomer material. Suitable materials and applicators and packaging systems are disclosed in U.S. Pat. Nos. 5,928,611 and 6,352,704 and U.S. patent application Ser. Nos. 09/430,177, 09/430,176, 09/430,289, 09/430,290, and 09/430,180 filed Oct. 29, 1999; Ser. No. 09/385,030 filed Aug. 30, 1999; and Ser. No. 09/176,889 filed Oct. 22, 1998; the entire disclosures of which are incorporated herein by reference.

In embodiments, an initiator may be desirable to promote polymerization. An initiator may be necessary for use on dry or non-biological surfaces, when the monomer contains a stabilizer, etc. In embodiments, initiators that initiate polymerization and/or cross-linking of the material may be applied to all or part of the surface of an applicator, including the interior and the exterior of the tip. Alternatively, the initiator may be coated only on an internal surface of the applicator tip. Alternatively, only a portion of the interior of the applicator tip is coated with the initiator. See, e.g., U.S. Pat. No. 5,928,611 to Leung and PCT Publication No. WO 01/32319.

The initiator on the applicator tip may be in the form of a solid, such as a powder or a film, or in the form of a liquid, such as a viscous or paste-like material. The initiator may also include a variety of additives, such as surfactants or emulsifiers. In certain embodiments, the initiator is soluble in the polymerizable and/or cross-linkable material, and/or comprises or is accompanied by at least one surfactant which, in embodiments, helps the initiator co-elute with the polymerizable and/or cross-linkable material. In other embodiments, the surfactant may help solubilize the initiator in the polymerizable and/or cross-linkable material.

Particular initiators for particular systems may be readily selected by one of ordinary skill in the art without undue experimentation. Suitable initiators include, but are not limited to, detergent compositions; surfactants: e.g., non-ionic surfactants such as polysorbate 20 (e.g., Tween 20™), polysorbate 80 (e.g., Tween 80™) and poloxamers, cationic surfactants such as benzalkonium chloride and tetrabutylammonium bromide, anionic surfactants such as sodium tetradecyl sulfate, and amphoteric or zwitterionic surfactants such as dodecyidimethyl(3-sulfopropyl)ammonium hydroxide; amines, imines and amides, such as imidazole, tryptamine, urea, arginine and povidine; phosphines, phosphites and phosphonium salts, such as triphenylphosphine and triethyl phosphite; alcohols such as ethylene glycol, methyl gallate, ascorbic acid, tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat 336; organometallics such as cobalt naphthenate and manganese acetylacetonate; and radical initiators and radicals, such as di-t-butyl peroxide and azo-bis(isobutyronitrile).

The monomer to be polymerized (including any associated materials as discussed herein) may also contain an initiator which is inactive until activated by a catalyst or accelerator (included within the scope of the term "initiator" as used herein) which may, for example, be provided in an applicator tip. Initiators activated by stimulation such as heat and/or light (e.g., ultraviolet or visible light) may also be suitable. The initiator may be applied to the surface of an applicator tip or may be impregnated or incorporated into the matrix or internal portions of an applicator tip. For example, the initiator may be applied to the applicator tip by spraying, dipping, or brushing the applicator tip with a liquid medium containing the initiator. The liquid medium may include non-aqueous solvents, such as ether, acetone, ethanol, pentane or mixtures thereof; or may include aqueous solutions. Often, the liquid medium is a low boiling point solvent.

B. Targeting Moieties

A targeting moiety, which assists another payload, agent, construct or other material in localizing to a particular target area, entering a target cell(s), and/or binding to a target receptor, may be selected on the basis of a particular condition or site to be treated or imaged. The targeting moiety may further comprise any of a number of different chemical entities. In embodiments, the targeting moiety is a small molecule.

In certain embodiments, the payload may comprise as a targeting moiety an internalizing polypeptide sequence, such as antepennepedia protein, HIV transactivating (Tat) protein, mastoparan, melittin, bombolittin, delta hemolysin, pardaxin, *Pseudomonas* exotoxin A, clathrin, diphtheria toxin, C9 complement protein, or a fragment of one of the preceding proteins. Internalizing peptides promote cellular uptake of molecules to which they are attached. Certain internalizing polypeptides, such as Tat, are also known to localize to the nucleus or other cellular structures. Thus a payload of the present invention which includes such an internalizing peptide sequence may exhibit increased uptake by target cells relative to payloads that lack such a sequence.

Receptor-mediated endocytotic activity has been utilized for delivering exogenous molecules such as proteins and nucleic acids to cells. Generally, a specified ligand is chemically conjugated by covalent, ionic, or hydrogen bonding to an exogenous molecule of interest (i.e., the exogenous compound), forming a conjugate molecule having a moiety (the ligand portion) that is still recognized in the conjugate by a target receptor. Using this technique, the phototoxic protein psoralen has been conjugated to insulin and internalized by the insulin receptor endocytotic pathway (Gasparro, Biochem. Biophys. Res. Comm. 141(2), pp. 502-509, Dec. 15, 1986); the hepatocyte-specific receptor for galactose terminal asialoglycoproteins has been utilized for the hepatocyte-specific transmembrane delivery of asialooorosomucoid-poly-L-lysine non-covalently complexed to a DNA plasmid (Wu, G. Y., J. Biol. Chem., 262(10), pp. 4429-4432, 1987); the cell receptor for epidermal growth factor has been utilized to deliver polynucleotides covalently linked to EGF to the cell interior (Myers, European Patent Application 86810614.7, published Jun. 6, 1988); the intestinally situated cellular receptor for the organometallic vitamin $B_{12}$-intrinsic factor complex has been used to mediate delivery to the circulatory system of a vertebrate host a drug, hormone, bioactive peptide or immunogen complexed with vitamin $B_{12}$ and delivered to the intestine through oral administration (Russell Jones et al., European patent Application 86307849.9, published Apr. 29, 1987); the mannose-6-phosphate receptor has been used to deliver low density lipoproteins to cells (Murray, G. J. and Neville, D. M., Jr., J. Bio. Chem, Vol. 255 (24), pp. 1194-11948, 1980); the cholera toxin binding subunit receptor has been used to deliver insulin to cells lacking insulin receptors (Roth and Maddox, J. Cell. Phys. Vol. 115, p. 151, 1983); and the human chorionic gonadotropin receptor has been employed to deliver a ricin a-chain coupled to HCG to cells with the appropriate HCG receptor in order to kill the cells (Oeltmann and Heath, J. Biol. Chem, vol. 254, p. 1028 (1979)).

One potential targeting moiety is biotin, a naturally occurring vitamin, which has been shown to localize effectively to tumors and sites of infection. Furthermore, as described in U.S. Pat. No. 5,716,594, imaging agents and therapeutic agents have been successfully delivered to such sites when coupled to biotin.

Another small molecule targeting moiety is folate (see U.S. Pat. No. 5,820,847). Folates are particularly useful in targeting cancer cells, since a variety of carcinomas over-express folate receptors. See Ladino et al. (*Int. J. Cancer* 1997, 73(6):859-6).

Riboflavin and its derivatives are other small molecule targeting moieties for targeting delivery of constructs to cancer cells (see, for example, U.S. Pat. No. 5,688,488). Additional nutrients believed to trigger receptor-mediated endocytosis and therefore useful targeting moieties of the instant claims include carnitine, inositol, lipoic acid, niacin, pantothenic acid, thiamin, pyridoxal, ascorbic acid, and the lipid soluble vitamins A, D, E and K.

A second exemplary type of small molecule targeting moiety includes steroidal lipids, such as cholesterol, and steroidal hormones, such as estradiol, testosterone, etc.

In another embodiment, the targeting moiety may comprise a protein. Particular types of proteins may be selected based on known characteristics of the target site or target cells. For example, the protein may be an antibody either monoclonal or polyclonal, where a corresponding antigen is displayed at the target site. As a second example, certain cells, such as malignant cells and blood cells (e.g., A, AB, B, etc.) display particular carbohydrates, for which a corresponding lectin may serve as a targeting moiety. In situations wherein a certain receptor is expressed by the target cells, the targeting moiety may comprise a protein or peptidomimetic ligand capable of binding to that receptor. Proteins corresponding to known cell surface receptors (including low density lipoproteins, transferrin and insulin), fibrinolytic enzymes, anti-HER2, platelet binding proteins such as annexins, and biological response modifiers (including interleukin, interferon, erythropoietin and colony-stimulating factor) are examples of preferred targeting moieties. Also, anti-EGF receptor antibodies, which internalize following binding to the receptor and traffic to the nucleus to an extent, are preferred targeting moieties for use in the present invention to facilitate delivery of Auger emitters and nucleus binding drugs to target cell nuclei.

A number of monoclonal antibodies that bind to a specific type of cell have been developed, including monoclonal antibodies specific for tumor-associated antigens in humans. Among the many such monoclonal antibodies that may be used are anti-TAC, or other interleukin-2 receptor antibodies; 9.2.27 and NR-ML-05 to the 250 kilodalton human melanoma-associated proteoglycan; and NR-LU-10 to a pancarcinoma glycoprotein. An antibody employed in the present invention may be an intact (whole) molecule, a fragment thereof, or a functional equivalent thereof. Examples of antibody fragments are $F(ab')_2$, Fab', Fab, and $F_v$ fragments, which may be produced by conventional methods or by genetic or protein engineering.

Other preferred targeting moieties include sugars (e.g., glucose, fructose, galactose, mannose) that are recognized by target-specific receptors. For example, instant constructs can be glycosylated with mannose residues (e.g., attached as C-glycosides to a free nitrogen) to yield targeted constructs having higher affinity binding to tumors expressing mannose receptors (e.g., glioblastomas and gangliocytomas), and bacteria, which are also known to express mannose receptors (Bertozzi, C R and M D Bednarski, Carbohydrate Research 223:243 (1992); J. Am. Chem. Soc. 114:2242,5543 (1992)), as well as potentially other infectious agents.

Additional ligands which may be suitable for use as targeting moieties in the present invention include haptens, epitopes, and dsDNA fragments and analogs and derivatives thereof. Such moieties bind specifically to antibodies, fragments or analogs thereof, including mimetics (for haptens and epitopes), and zinc finger proteins (for dsDNA fragments).

TABLE I

Exemplary Targets and Targeting Moieties

| Target | Targeting Moiety |
| --- | --- |
| Cell-surface receptor | Receptor Ligand |
| Hapten, epitope | Antibody |
| DsDNA fragment | Zinc finger protein |
| Carbohydrate | Lectin |
| Enzyme | Enzyme inhibitor |

TABLE II

Exemplary Tissue-Selective Targeting Moieties

| Cell Type(s) | Targeting Moiety |
| --- | --- |
| liver cells | galactose |
| Kupffer cells; cancer cells expressing mannose receptors (e.g., glioblastomas and ganglic cytomas) | mannose |
| adipose tissue | insulin |
| Lymphocytes | Fab fragment versus CD4 or gp 120 |
| Fibroblasts | mannose-6-phosphate |
| nerve cells | Apolipoprotein E |
| Lung | Fab fragment vs. polymeric immunoglobulin receptor (Pig R) |
| Enterocyte | Vitamin $B_{12}$ |
| prostate cancer cells | antibody to prostate specific antigen |
| breast cancer cells | antibody to Her2 antigen |

Antibodies may be effective ways of targeting cells that express particular antigens on the cell surface, and thus can be used to selectively target particular cells, such as cancer cells or cells from a particular tissue. Furthermore, antibodies may be made by using standard protocols (see, for example, Antibodies: A Laboratory Manual, ed. Harlow and Lane (Cold Spring Harbor Press: 1988)). A mammal, such as a mouse, a hamster or rabbit can be immunized with an immunogenic form of the peptide (e.g., a polypeptide or an antigenic fragment which is capable of eliciting an antibody response, or a fusion protein as described above).

In one exemplary technique, following immunization of an animal with an antigenic preparation of a polypeptide, antisera may be obtained and, if desired, polyclonal antibodies isolated from the serum. To produce monoclonal antibodies, antibody-producing cells (lymphocytes) may be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., Immunology Today, 4: 72 (1983)), and the EBV-hybridoma technique to produce human monoclonal antibodies (Cole et al., Monoclonal Antibodies and Cancer Therapy, Alan R. Liss, Inc. (1985) pp. 77-96). Hybridoma cells may be screened immunochemically for production of antibodies specifically reactive with a polypeptide of the present invention and monoclonal antibodies isolated from a culture comprising such hybridoma cells.

The term antibody as used herein is intended to include fragments thereof which are also specifically reactive with one of the subject mammalian polypeptides. Antibodies may be fragmented using conventional techniques and the fragments screened for utility in the same manner as described above for whole antibodies. For example, $F(ab)_2$ fragments may be generated by treating antibody with pepsin. The resulting $F(ab)_2$ fragment may be treated to reduce disulfide bridges to produce Fab fragments. Antibodies of the present invention are further intended to include bispecific, single-chain, and chimeric and humanized molecules having affinity for a subject protein conferred by at least one CDR region of the antibody.

In certain embodiments, targeting moieties facilitate binding of the construct to their respective target molecules with an affinity of at least about $k_D \geq 10^{-9}$M. In embodiments, targeted constructs exhibit a high target to non-target ratio when administered in vivo. Such ratio may be, in certain examples, $\geq 5:1$.

A targeting moiety may include an antisense oligonucleotide designed to be complementary to a nucleic acid of interest, and which may inhibit the transcription of a related gene, serve as a probe for the expression of that gene, or any combination thereof. Antisense oligonucleotides may comprise any polymeric compound capable of specifically binding to a target polynucleotide by way of a regular pattern of monomer-to-nucleoside interactions, such as Watson-Crick type of base pairing, Hoogsteen or reverse Hoogsteen types of base pairing, or the like. The oligonucleotide portion may be modified to enhance its efficacy, pharmacokinetic properties, or physical properties. For example, it is known that enhanced lipid solubility and/or resistance to nuclease digestion results by substituting an alkyl group or alkoxy group for a phosphate oxygen in the internucleotide phosphodiester linkage to form an alkylphosphonate oligonucleoside or alkylphosphotriester oligonucleotide. Non-ionic oligonucleotides such as these are characterized by increased resistance to nuclease hydrolysis and/or increased cellular uptake, while retaining the ability to form stable complexes with complementary nucleic acid sequences. The alkylphosphonates, in particular, are stable to nuclease cleavage and soluble in lipid. The preparation of alkylphosphonate oligonucleosides is disclosed in Ts'o et al., U.S. Pat. No. 4,469,863.

Preferably, nuclease resistance is conferred on the nucleotides by providing nucleaseresistant internucleosidic linkages. Many such linkages are known in the art, e.g., phosphorothioate: Zon and Geiser, Anti-Cancer Drug Design, 6:539-568 (1991); Stec et al., U.S. Pat. No. 5,151,510; Hirschbein, U.S. Pat. No. 5,166,387; Bergot, U.S. Pat. No. 5,183,885; phosphorodithioates: Marshall et al., Science, 259:1564-1570 (1993); Caruthers and Nielsen, International application PCT/US89/02293; phosphoroamidates, e.g., —OP(=O)(NR$_1$R$_2$)—O— with R$_1$ and R$_2$hydrogen or C$_1$-C$_3$ alkyl; Jager et al., Biochemistry, 27:7237-7246 (1988); Froehler et al., International application PCT/US90/03138; peptide nucleic acids: Nielsen et al., Anti-Cancer Drug Design, 8:53-63 (1993), International application PCT/EP92/01220; methylphosphonates: Miller et al., U.S. Pat. No. 4,507,433, Ts'o et al., U.S. Pat. No. 4,469,863; Miller et al., U.S. Pat. No. 4,757,055; and P-chiral linkages of various types, especially phosphorothioates, Stec et al., European patent application 506,242 (1992) and Lesnikowski, Bioorganic Chemistry, 21:127-155 (1993). Additional nuclease-resistant linkages include phosphoroselenoate, phosphorodiselenoate, phosphoroanilothioate, phosphoroanilidate, alkylphosphotriester such as methyl- and ethylphosphotriester, carbonates such as carboxymethyl ester, carbamate, morpholino carbamate, 3'-thioformacetal, silyl such as dialkyl (C,—C6)- or diphenylsilyl, sulfamate ester, and the like. Such linkages and methods for introducing them into oligonucleotides are described in many references, e.g., reviewed generally by Peyman and Ulmann, Chemical Reviews 90:543-584 (1990); Milligan et al., J. Med. Chem., 36:1923-1937 (1993); Matteucci et al., International application PCT/US91/06855.

Resistance to nuclease digestion may also be achieved by modifying the internucleotide linkage at both the 5' and 3' termini with phosphoroamidites according to the procedure of Dagle et al., Nucl. Acids Res. 18, 4751-4757 (1990).

Preferably, phosphorus analogs of the phosphodiester linkage are employed in the nucleic acids, such as phosphorothioate, phosphorodithioate, phosphoramidate, or methylphosphonate. More preferably, phosphorothioate is employed as the nuclease resistant linkage.

Phosphorothioate oligonucleotides contain a sulfur-for-oxygen substitution in the internucleotide phosphodiester bond. Phosphorothioate oligonucleotides combine the properties of effective hybridization for duplex formation with substantial nuclease resistance, while retaining the water solubility of a charged phosphate analogue. The charge is believed to confer the property of cellular uptake via a receptor (Loke et al., Proc. Natl. Acad. Sci., 86, 3474-3478 (1989)).

It is understood that in addition to the preferred linkage groups, oligonucleotides may comprise additional modifications, e.g., boronated bases, Spielvogel et al., U.S. Pat. No. 5,130,302; cholesterol moieties, Shea et al., Nucleic Acids Research, 18:3777-3783 (1990) or Letsinger et al., Proc. Natl. Acad. Sci., 86:6553-6556 (1989); and 5-propynyl modification of pyrimidines, Froehler et al., Tetrahedron Lett., 33:5307-5310 (1992).

Preferably, oligonucleotides are synthesized by conventional means on commercially available automated DNA synthesizers, e.g., an Applied Biosystems (Foster City, Calif.) model 380B, 392 or 394 DNA/RNA synthesizer. Preferably, phosphoramidite chemistry is employed, e.g., as disclosed in the following references: Beaucage and Iyer, Tetrahedron, 48:2223-2311 (1992); Molko et al., U.S. Pat. No. 4,980,460; Koster et al., U.S. Pat. No. 4,725,677; Caruthers et al., U.S. Pat. Nos. 4,415,732, 4,458,066, and 4,973,679.

In embodiments where triplex formation is desired, there may be constraints on the selection of target sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g., whether ribose or deoxyribose nucleosides are employed), base modifications (e.g., methylated cytosine, and the like) in order to maximize, or otherwise regulate, triplex stability as desired in particular embodiments, e.g., Roberts et al., Proc. Natl. Acad. Sci., 88:9397-9401 (1991); Roberts et al., Science, 58:1463-1466 (1992); Distefano et al., Proc. Natl. Acad. Sci., 90:1179-1183 (1993); Mergny et al., Biochemistry, 30:9791-9798 (1992); Cheng et al., J. Am. Chem. Soc., 114:4465-4474 (1992); Beal and Dervan, Nucleic Acids Research, 20:2773-2776 (1992); Beal and Dervan, J. Am. Chem. Soc., 114:4976-4982; Giovannangeli et al., Proc. Natl. Acad. Sci., 89:8631-8635 (1992); Moser and Dervan, Science, 238:645-650 (1987); McShan et al., J. Biol. Chem., 267:5712-5721 (1992); Yoon et al., Proc. Natl. Acad. Sci., 89:3840-3844 (1992); and Blume et al., Nucleic Acids Research, 20:1777-1784 (1992).

The length of the oligonucleotide moieties may be sufficiently large to ensure that specific binding will take place only at the desired target polynucleotide and not at other adventitious sites, as explained in many references, e.g., Rosenberg et al., International application PCT/US92/05305; or Szostak et al., Meth. Enzymol, 68:419-429

(1979). The desired length is determined by several factors, including the inconvenience and expense of synthesizing and purifying oligomers greater than about 30-40 nucleotides in length, the greater tolerance of longer oligonucleotides for mismatches than shorter oligonucleotides, whether modifications to enhance binding or specificity are present, whether duplex or triplex binding is desired, and the like. Usually, oligonucleotides useful in the invention have lengths in the range of about 12 to 60 nucleotides. More preferably, oligonucleotides have lengths in the range of about 15 to 40 nucleotides; and most preferably, they have lengths in the range of about 18 to 30 nucleotides.

In general, oligonucleotides used in the practice of the present invention will have a sequence which is completely complementary to a selected portion of the target polynucleotide. Absolute complementarity is not however required, particularly in larger oligomers. Thus, reference herein to a "nucleotide sequence complementary to" a target polynucleotide does not necessarily mean a sequence having 100% complementarity with the target segment. In general, any oligonucleotide having sufficient complementarity to form a stable duplex with the target (e.g., an oncogene mRNA), that is, an oligonucleotide which is "hybridizable" under reasonable stringency conditions, is suitable. Stable duplex formation depends on the sequence and length of the hybridizing oligonucleotide and the degree of complementarity with the target polynucleotide. Generally, the larger the hybridizing oligomer, the more mismatches may be tolerated. More than one mismatch may not be suitable for oligomers of less than about 21 nucleotides. One skilled in the art may readily determine the degree of mismatching that may be tolerated between any given oligomer and the target sequence, based upon the melting point, and therefore the thermal stability, of the resulting duplex.

The thermal stability of hybrids formed by the oligonucleotides may be determined by way of melting, or strand dissociation, curves. The temperature of fifty percent strand dissociation is taken as the melting temperature, $T_m$, which, in turn, provides a convenient measure of stability. $T_m$ measurements are typically carried out in a saline solution at neutral pH with target and oligonucleotide concentrations at between about 1.0-2.0 µm. Typical conditions are as follows: 150 mM NaCl and 1 mM $MgCl_2$ in a 10 mM sodium phosphate buffer (pH 7.0) or in a 10 mM Tris-HCl buffer (pH 7.0). Data for melting curves are accumulated by heating a sample of the oligonucleotide/target polynucleotide complex from room temperature to about 85° C. As the temperature of the sample increases, absorbance of 260 nm light is monitored at 1° C. intervals, e.g., using a Cary (Australia) model 1E or a Hewlett-Packard (Palo Alto, Calif.) model HP 8459 UV/VIS spectrophotometer and model HP 89100A temperature controller, or like instruments. Such techniques provide a convenient means for measuring and comparing the binding strengths of oligonucleotides of different lengths and compositions.

In certain embodiments, the nucleic acid portion may additionally function to inhibit or suppress the transcription of a gene. Where the target polynucleotide comprises an mRNA transcript, oligonucleotides complementary to and hybridizable with any portion of the transcript are, in principle, effective for inhibiting translation. This occurs because each protein synthesized by a cell is encoded by a specific messenger mRNA (mRNA). If translation of a specific RNA is inhibited, the protein product derived from this translation will likewise be reduced. Oligonucleotide sequences designed to be complementary (antisense) to a specific target mRNA sequence will bind to the target sequence thereby inhibiting translation of that specific mRNA. It is believed that an antisense oligonucleotide; by hybridizing to the RNA and forming a complex, blocks target mRNA ribosomal binding, causing translational inhibition. Alternatively, the duplex that is formed by the sense and antisense molecules may be easier to degrade. Other theories describe complexes that antisense RNA could form with complementary DNA to inhibit mRNA transcription. Thus, an antisense oligonucleotide might inhibit the translation of a given gene product by either directly inhibiting translation or through inhibition of transcription.

It is believed that translation is most effectively inhibited by blocking the mRNA at a site at or near the initiation codon. Thus, oligonucleotides complementary to the 5'-region of mRNA transcript are preferred. Oligonucleotides complementary to the target mRNA, including the initiation codon (the first codon at the 5' end of the translated portion of the transcript), or codons adjacent the initiation codon, are preferred.

While antisense oligomers complementary to the 5'-region of the target mRNA transcripts are preferred, particularly the region including the initiation codon, it should be appreciated that useful antisense oligomers are not limited to those oligomers complementary to the sequences found in the translated portion of the mRNA transcript, but also includes oligomers complementary to nucleotide sequences contained in, or extending into, the 5'- and 3'-untranslated regions.

C. Therapeutic Agents.

Therapeutic agents are biologically active, often by countering the abnormal condition of the targeted site (e.g., tumor or infection).

A therapeutic agent useful in connection with a cyanoacrylic monomer or polymer may be any of a number of chemical entities, e.g., an enzyme, drug, radionuclide, enzyme inhibitor, etc. For example, moieties useful as therapeutic agents include amino acids and their derivatives; analgesics such as acetaminophen, aspirin, and ibuprofen; antiasthmatics; anticonvulsants; antidepressants such as amitriptyline, fluoxetine, nortriptyline, and imipramine; antiemetics; antifungal agents including: allyamines, imidazoles, polyenes, and triazoles; antigens and antibodies thereto; antihistamines such as chlorpheniramine and brompheniramine; antihypertensive agents such as clonidine, methyldopa, prazosin, verapamil, nifedipine, captopril, and enalapril; anti-inflammatory agents including non-steroidal agents, such as aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, COX-2 inhibitors and others, as well as steroidal agents, such as glucocorticoids; antimicrobials such as aminoglycosides, amphenicols, cinoxacin, ciprofloxacin, 2,4-diaminopyrimidines, β-lactams (e.g. carbapenems, cephalosporins, cephamycins, monobactams, oxacephems and penicillins), lincosamides, macrolides, nitrofurans, norfloxacin, peptides, polypeptides, and proteins (e.g. defensins), bacitracin, polymyxin, cecropins, magainin II, indolicidin, ranalexin, protegrins, gallinacins, tritrpticin, lactoferricin, drosomycin, holotricin, thanatin, dermaseptin, iturins, syringomycins, nikkomycins, polyoxins, FR-900403, echinocandins, pneumocandins, aculeacins, mulundocandins, WF 11899, aureobasidins, schizotrin A, cepacidines, zeamatin, cyclopeptides and D4e1), quinolones and analogs, sulfonamides, sulfones, tetracyclines; antinauseants; anti-Parkinson agents; antispasmodics; apoproteins, bronchodilators such as albuterol and theophylline; antivirals including: purines/pyrimidinones (e.g. acyclovir, dideoxy-cytidine, -adenosine, or -inosine, interferons, amantadine, ribavirin); beta-blockers such as propranolol, metoprolol, atenolol, labetolol, timolol, penbutolol, and pindolol; cancer drugs including chemotherapeutic agents; cardiovascular agents including antiarrhythmics; cardiac glycosides, antianginals and vasodilators; central nervous system agents including stimulants, psychotropics, antimanics, and depressants; coenzymes; decongestants; diuretics; enzymes; enzyme inhibitors; expectorants; glycoproteins; H-2 antagonists such as nizatidine, cimetidine, famotidine, and ranitidine; haptens and antibodies thereto; hormones, lipids, liposomes; mucolytics; muscle relaxants; protein analogs in which at least one non-peptide linkage replaces a peptide linkage; phospholipids; prostaglandins; receptors and other membrane proteins; retro-inverso oligopeptides; stimulants; toxins such as aflatoxin, digoxin, rubratoxin, and xanthotoxin; tranquilizers such as diazepam, chordiazepoxide, oxazepam, alprazolam, and triazolam; and vitamins and mineral and nutritional additives. Other therapeutic agents are set forth in the Merck Index, and U.S. Pat. No. 5,256,765 and PCT Publications Nos. WO 01/32319, WO 01/30408 and WO 01/32795 disclose a variety of payloads, including therapeutic agents. In addition to therapeutic agents that are currently in use, the instant invention contemplates agents that are in development or will be developed and that are useful for treating or preventing the progression of an infection, inflammatory response, tumor, or other abnormal condition.

In embodiments, the therapeutic agents may include, but are not limited to, medicaments such as antibiotics, antimicrobials, antiseptics, bacteriocins, bacteriostats, disinfectants, steroids, anesthetics, antifungal agents, anti-inflammatory agents, antibacterial agents, antiviral agents, antitumor agents, growth promoting substances, antioxidants, or mixtures thereof. Such compounds include, but are not limited to, acetic acid, aluminum acetate, bacitracin, bacitracin zinc, benzalkonium chloride, benzethonium chloride, betadine, calcium chloroplatinate, certrimide, cloramine T, chlorhexidine phosphanilate, chlorhexidine, chlorhexidine sulfate, chloropenidine, chloroplatinatic acid, ciprofloxacin, clindamycin, clioquinol, cysostaphin, gentamicin sulfate, hydrogen peroxide, iodinated polyvinylidone, iodine, iodophor, minocycline, mupirocin, neomycin, neomycin sulfate, nitrofurazone, non-onynol 9, potassium permanganate, penicillin, polymycin, polymycin B, polymyxin, polymyxin B sulfate, polyvinylpyrrolidone iodine, povidone iodine, 8-hydroxyquinoline, quinolone thioureas, rifampin, rifamycin, copper chloride, copper sulfate, copper peptides, silver acetate, silver benzoate, silver carbonate, silver chloride, silver citrate, silver iodide, silver nitrate, silver oxide, silver sulfate, sodium chloroplatinate, sodium hypochlorite, sphingolipids, tetracycline, zinc oxide, salts of sulfadiazine (such as silver, sodium, and zinc), antioxidants such as vitamins such as vitamin E, other agents mentioned above, and mixtures thereof. Preferable therapeutic agents are USP approved, more preferably USP monographed.

In embodiments, the therapeutic agents may be selected from among known anti-microbial agents, including, but not limited to, parabens and cresols. For example, suitable parabens include, but are not limited to, alkyl parabens and salts thereof, such as methylparaben, methylparaben sodium, ethylparaben, propylparaben, propylparaben sodium, butylparaben, and the like. Suitable cresols include, but are not limited to, cresol, chlorocresol, and the like. The agents can also be selected from other known agents including, but not limited to, hydroquinone, pyrocatechol, resor-cinol, 4-n-hexyl resorcinol, captan (i.e., 3a,4,7,7a-tetrahydro-2-((trichloromethyl)thio)-1H-isoindole-1,3(2H)-dione), benzalkonium chloride, benzalkonium chloride solution, benzethonium chloride, benzoic acid, benzyl alcohol, cetylpyridinium chloride, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, phenylmercuric compounds such as phenylmercuric borate, phenylmercuric nitrate and phenylmercuric acetate, formaldehyde, and formaldehyde generators such as Germall II® and Germall 115® (imidazolidinyl urea, available from Sutton Laboratories, Charthan, N.J.).

Furthermore, various other compounds can be screened for their therapeutic effects, and then selected based on the results of this screening. For example, compounds can be tested for their antimicrobial effectiveness by one or more of a USP microbial limits test, a USP bacteriostasis and fungistasis test, and a USP antibiotics-microbial assay. See, for example, USP 23 <51>, Supplement 8, "Antimicrobial Effectiveness Testing," the entire disclosure of which is incorporated herein by reference.

According to the present invention, a selection process may be used to select appropriate agents for use in specific polymerizable alkyl cyanoacrylate monomer compositions in accordance with the invention. Such a screening process can be used to select from among the various known agents, or from those agents determined by the above USP testing regimens. The agent should not significantly adversely affect the stability of the monomer or polymer composition. In addition, in embodiments, the agent in combination with the monomer composition should also be compatible with one or more sterilization procedures. Thus, a suitable procedure for selecting an agent generally involves selecting a group of potential agents, assessing their stability in the monomer or polymer composition, and testing for their compatibility with one or more sterilization procedures.

Potential agents for testing can readily be selected by one of ordinary skill in the art from known sources. For example, such sources can include the USP list of approved agents, or other such lists maintained by various governmental or non-governmental agencies, such as the U.S. Food and Drug Administration (US FDA).

Once a potential agent is selected, it can be tested for stability in the monomer or polymer composition, such as by mixing an appropriate amount of the agent with a desired amount of the monomer or polymer composition and any other desired additives.

Stability is preferred because it is important to maintain the stability of the monomer, for example, composition within acceptable levels, such as commercially acceptable levels whereby the composition is not prematurely polymerized prior to application of the monomer composition to a desired substrate. One possible measure of the stability of the composition, other than a visual examination of the properties of the composition, is a measure of any changes in viscosity of the composition from a time prior to adding the agent to a time after adding the agent. For example, dramatic increases or decreases in the viscosity can indicate instability of the composition, such as premature polymerization or other chemical degradation of the monomer composition or components thereof.

In embodiments of the present invention, it is preferred that the agent exhibit stability in the monomer composition for at least five minutes after mixing or dissolving the agent in the polymerizable monomer compound. More preferably, stability of the monomer composition is maintained for at least one hour, preferably ten hours, and more preferably twenty-four hours after mixing the agent with the polymerizable monomer compound. Even more preferably, stability of the monomer composition is maintained for a time period sufficient to provide a commercially significant shelf-life to the monomer composition, such as one year, eighteen months, two years or more, or even an extended shelf-life as compared to similar monomer compositions not including such an agent. As used herein, "stability" refers to the resultant composition maintaining a commercially acceptable form for the prescribed amount of time. That is, the composition does not prematurely polymerize or otherwise change form or degrade to the point that the composition is not useful for its intended purpose. Thus, while some polymerization or thickening of the monomer composition may occur, such as can be measured by changes in viscosity of the composition, such change is not so extensive as to destroy or significantly impair the usefulness of the composition.

Optionally, in embodiments of the present invention, the potential agent can be tested for its compatibility with one or more sterilization procedures. This optional screening procedure can also be performed, for example, by mixing an appropriate amount of the agent with a desired amount of the monomer composition and any other desired additives, and then subjecting the resultant composition to one or more sterilization procedures. Compatibility of the agent with one or more sterilization procedures is preferred in embodiments of the present invention because many uses of the polymerizable monomer compositions, such as many medical applications, require or prefer sterilized products. Following sterilization, the agent can exert antimicrobial action in killing or preventing growth of microbes.

Of course, as will be apparent to those skilled in the art, the above selection procedures need not be conducted in any particular order, and need not be conducted sequentially. That is, the procedures can be conducted in any order, and can be conducted simultaneously, if desired. Likewise, not all of the procedures may be necessary, and other screening procedures may be used as necessary depending on particular applications.

D. Imaging Agents

Cyanoacrylic monomers or polymers may alternatively or additionally be labeled with or incorporate any of a variety of imaging agents, selection of which will depend to some extent on the means used to detect or monitor the compound in vivo or in vitro. Preferred imaging agents for performing positron emission tomography (PET) and single photon emission computer tomography (SPECT) include F-18, Tc-99m, and I-123. Preferred imaging agents for magnetic resonance imaging (MRI) include an appropriate atom with unpaired spin electrons or a free radical.

Imaging agents are detectable, e.g., by emitting light, radioactive emissions, or chemical signals, by absorbing or reflecting radiation (e.g., x-rays), or by otherwise changing a characteristic of treated cells relative to untreated cells.

When the payload is intended to perform in an imaging capacity, the payload may, for example, comprise a moiety such as a radionuclide or paramagnetic contrast agent, fluorescent or chemiluminescent label, or other type of detectable marker. The imaging agents described above may contain any label in accordance with the invention. Highly specific and sensitive labels are provided by radionuclides, which can then be detected using positron emission tomography (PET) or Single Photon Emission Computed Tomography. (SPECT) imaging. More preferably, the imaging agent of the invention contains a radionuclide selected from the group consisting of $^{131}I$, $^{125}I$, $^{123}I$, $^{99m}Tc$, $^{18}F$, $^{68}Ga$, $^{67}Ga$, $^{72}As$, $^{89}Zr$, $^{64}CU$, $^{62}Cu$, $^{111}In$, $^{203}Pb$, $^{198}Hg$, $^{11}C$, $^{97}Ru$, and $^{201}Tl$ or a paramagnetic contrast agent, such as gadolinium, cobalt, nickel, manganese, and iron. As will be discussed below, these atoms may be directly incorporated into a targeting moiety or oligonucleotide, or may be attached through a separate chemical structure. Additional information relating to the use of chelated radionuclides may be found in U.S. Pat. Nos. 5,783,171 and 5,688,488.

E. Methods for Preparing Cyanoacrylic Monomers

Although a variety of methods may be employed for preparing the subject monomers, in certain embodiments, a cyanoalkanoic acid is coupled with a suitable R' subunit before installation of the polymerizable double bond. This ordering tends to reduce difficulties associated with the nucleophile-sensitive cyanoacrylic core during carboxylic acid coupling. A general method for coupling a 2-cyanoalkanoic acid with an amino acid is disclosed in Ghosh et al., *J. Med. Chem.*, 1992, 35, 4175-4179, and such methods may be employed for preparing monomers of the present invention. In certain embodiments, some of the functional groups on R' may need to be protected for this step or for installation of the polymerizable double bond, as will be recognized by one of skill in the art.

A Knoevenagel condensation with formaldehyde is often used in the art to convert a cyanoacetate ester to a cyanoacrylate, and may be used in embodiments of the present invention. However, such a reaction may not be compatible with certain functional groups that may be present on R'. Thus, in certain embodiments, the polymerizable double bond may be installed by the method taught in U.S. Pat. No. 5,504,252 and in Klemarczyk, P. *Polymer*, 1997, 39, 173-181. In such embodiments, a 2-cyanopropionic acid or higher congener is coupled to R'. A selenoether (or other appropriate substituent) may then be installed at the 2-position of the cyanoalkanoic derivative. The selenoether may then be treated with hydrogen peroxide or another oxidizing agent to promote elimination of the intermediate selenoxide to the 2-cyanoalkenoic acid, thereby installing the polymerizable double bond of the monomer. In certain embodiments, protecting groups may be removed from R' prior to oxidizing the selenoether. Applications of this scheme to the synthesis of the subject monomers are discussed in detail in the Exemplifications below.

The attachment of a payload to the cyanoacrylic core may be effected by any means that produces a linkage that is sufficiently stable to withstand the conditions used and that does not materially impair the function or reactivity of either constituent. In many embodiments, it may be desirable to link the cyanoacrylic core directly to a functional group of the payload or targeting moiety, while in other embodiments, a tether or linker molecule may be used to separate the payload or targeting moiety from the cyanoacrylic core, or to facilitate or improve the attachment between them. One of ordinary skill in, the art will readily be able to attach suitable molecules to the cyanoacrylic core, e.g., by using synthesis methods known in the art and/or one of the methods discussed below.

Numerous chemical linking methods are known and potentially applicable for conjugating a payload or targeting moiety to the cyanoacrylic core. Many known chemical linking methods are non-specific, i.e., they do not direct the point of coupling to any particular site on a polypeptide, polynucleotide, or other molecule. Thus while such methods are useful in many embodiments of the invention, use of non-specific linking agents may affect functional sites or sterically block active sites of certain embodiments, rendering the conjugated materials biologically inactive.

In certain embodiments, one approach to increasing coupling specificity is direct chemical coupling to a functional group found only once or a few times in one or both of the molecules to be linked. For example, in many proteins, cysteine, which is the only protein amino acid containing a thiol group, occurs only a few times. Also, for example, if a polypeptide contains no lysine residues, a cross-linking reagent specific for primary amines will be selective for the amino terminus of that polypeptide. Thus in utilization of this approach to increase coupling specificity, it is preferred that the molecule have the suitable reactive residues in areas of the molecule that may be altered without loss of the molecule's biological activity.

Cysteine residues may be replaced when they occur in parts of a polypeptide sequence where their participation in a cross-linking reaction would likely interfere with biological activity. When a cysteine residue is replaced, it is often desirable to minimize resulting changes in polypeptide folding. Changes in polypeptide folding are minimized when the replacement is chemically and sterically similar to cysteine. For these reasons, serine is preferred as a replacement for cysteine. When a cysteine residue is introduced, introduction at or near the amino or carboxy terminus is preferred. Conventional methods are available for such amino acid sequence modifications, whether the polypeptide of interest is produced by chemical synthesis or expression of recombinant DNA.

Coupling of two constituents may be accomplished via a coupling or conjugating agent. Several intermolecular cross-linking reagents are preferred (see, for example, Means, G. E. and Feeney, R. E., Chemical Modification of Proteins, Holden-Day, 1974, pp. 39-43). Among these reagents are, for example, 1-succinimidyl 3-(2-pyridyldithio) propionate (SPDP) or N,N'-(1,3-phenylene) bismaleimide (both of which are highly specific for sulfhydryl groups and form irreversible linkages); N,N'-ethylene-bis-(iodoacetamide) or other such reagent having 6 to 11 carbon methylene bridges (which are relatively specific for sulfhydryl groups); and 1,5-difluoro-2,4-dinitrobenzene (which forms irreversible linkages with amino and tyrosine groups). Other cross-linking reagents useful for this purpose include but are not limited to: p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylene-diisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Linking reagents may be homobifunctional, i.e., having two functional groups that undergo the same reaction. A preferred homobifunctional cross-linking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of polypeptides that contain cysteine residues.

Linking reagents may also be heterobifunctional. Heterobifunctional cross-linking agents have two different functional groups, for example an amine-reactive group and a thiolreactive group, that will cross-link two proteins having free amines and thiols, respectively.

Heterobifunctional cross-linkers provide the ability to design more specific coupling methods for conjugating two chemical entities, thereby reducing the occurrences of unwanted side reactions such as homo-protein polymers. A wide variety of heterobifunctional cross-linkers are known in the art. Examples of heterobifunctional cross-linking agents include succinimidyl 4-(N-maleimidomethyl)-cyclohexane-1-carboxylate (SMCC), N-succinimidyl (4-iodoacetyl) aminobenzoate (SIAB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl-3-(2-pyridyldithio) propionate (SPDP), succinimidyl 6-[3-(2-pyridyldithio) propionate] hexanoate (LC-SPDP), m-maleimidobenzoyl-N-hydroxysuccinimide ester (MBS), and succinimide 4-(p-maleimidophenyl)butyrate (SMPB), an extended chain analog of MBS. The succinimidyl group of these cross-linkers reacts with a primary amine, and the thiol-reactive maleimide forms a covalent bond with the thiol of a cysteine residue.

Linking reagents often have low solubility in water. A hydrophilic moiety, such as a sulfonate group, may be added to the linking reagent to improve its water solubility.

Sulfo-MBS and sulfo-SMCC are examples of cross-linking reagents modified for water solubility.

Another reactive group useful as part of a heterobifunctional linker is a thiol reactive group. Common thiol-reactive groups include maleimides, halogens, and pyridyl disulfides. Maleimides react specifically with free sulfhydryls (cysteine residues) in minutes, under slightly acidic to neutral (pH 6.5-7.5) conditions. Haloalkyl groups (e.g., iodoacetyl functions) react with thiol groups at physiological pH's. Both of these reactive groups result in the formation of stable thioether bonds.

In addition to the heterobifunctional cross-linkers, there exist a number of other linking agents including homobifunctional and photoreactive linkers. Disuccinimidyl suberate (DSS), bismaleimidohexane (BMH) and dimethylpimelimidate-2 HCl (DMP) are examples of useful homobifunctional cross-linking agents, and bis-[β-(4-azidosalicylamido)ethyl]disulfide (BASED) and N-succinimidyl-6(4'-azido-2'-nitrophenylamino)hexanoate (SANPAH) are examples of useful photoreactive cross-linkers for use in this invention. For a recent review of protein coupling techniques, see Means et al. (1990) Bioconjugate Chemistry 1:2-12.

Many linking reagents yield a conjugate that is essentially non-cleavable under cellular conditions. However, some linking reagents contain a covalent bond, such as a disulfide, that is clearable under cellular conditions. For example, dithiobis(succinimidylpropionate) (DSP), Traut's reagent and N-succinimidyl 3-(2-pyridyldithio) propionate (SPDP) are well-known cleavable cross-linkers. The use of a cleavable crosslinking reagent may permit the payload to separate from the construct after delivery to the target. Direct disulfide linkage may also be useful. Additional cleavable linkages are known in the art and may be employed to advantage in certain embodiments of the present invention.

Many methods for linking compounds, such as proteins, labels, and other chemical entities, to nucleotides are known in the art. Some new cross-linking reagents such as n-γ-maleimidobutyryloxy-succinimide ester (GMBS) and sulfo-GMBS, have reduced immunogenicity. Substituents have been attached to the 5' end of preconstructed oligonucleotides using amidite or H-phosphonate chemistry, as described by Ogilvie, K. K., et al., Pure and Appl. Chem. (1987) 59:325, and by Froehler, B. C., Nucleic Acids Res.

(1986) 14:5399. Substituents have also been attached to the 3' end of oligomers, as described by Asseline, U., et al., Tet. Lett. (1989) 30:2521. This last method utilizes 2,2'-dithioethanol attached to a solid support to displace diisopropylamine from a 3' phosphonate bearing the acridine moiety and is subsequently deleted after oxidation of the phosphorus. Other substituents have been bound to the 3' end of oligomers by alternate methods, including polylysine (Bayard, B., et al., Biochemistry (1986) 25:3730; Lemaitre, M., et al., Nucleosides and Nucleotides (1987) 6:311) and, in addition, disulfides have been used to attach various groups to the 3' terminus, as described by Zuckerman, R., et al., Nucleic Acids Res (1987) 15:5305. It is known that oligonucleotides which are substituted at the 3' end show increased stability and increased resistance to degradation by exonucleases (Lancelot, G., et al., Biochemistry (1985) 24:2521; Asseline, U., et al., Proc Natl Acad Sci USA (1984) 81:3297). Additional methods of attaching non-nucleotide entities to oligonucleotides are discussed in U.S. Pat. Nos. 5,321,131 and 5,414,077.

Alternatively, an oligonucleotide may include one or more modified nucleotides having a group attached via a linker arm to the base. For example, Langer et al (Proc. Natl. Acad. Sci. U.S.A., 78(11):6633-6637, 1981) describes the attachment of biotin to the C-5 position of dUTP by an allylamine linker arm. The attachment of biotin and other groups to the 5-position of pyrimidines via a linker arm is also discussed in U.S. Pat. No. 4,711,955. Nucleotides labeled via a linker arm attached to the 5- or other positions of pyrimidines are also suggested in U.S. Pat. No. 4,948,882. Bisulfate-catalyzed transamination of the $N^4$-position of cytosine with bifunctional amines is described by Schulman et al. (Nucleic Acids Research, 9(5): 1203-1217, 1981) and Draper et al (Biochemistry, 19: 1774-1781, 1980). By this method, chemical entities are attached via linker arms to cytidine or cytidine-containing polynucleotides. The attachment of biotin to the $N^4$-position of cytidine is disclosed in U.S. Pat. No. 4,828,979, and the linking of moieties to cytidine at the N4-position is also set forth in U.S. Pat. Nos. 5,013,831 and 5,241,060. U.S. Pat. No. 5,407,801 describes the preparation of an oligonucleotide triplex wherein a linker arm is conjugated to deoxycytidine via bisulfate-catalyzed transamination. The linker arms include an aminoalkyl or carboxyalkyl linker arm. U.S. Pat. No. 5,405,950 describes cytidine analogs in which a linker arm is attached to the $N^4$-position of the cytosine base.

Numerous cross-linking reagents, including the ones discussed above, are commercially available. Detailed instructions for their use are readily available from the commercial suppliers. A general reference on protein cross-linking and conjugate preparation is: S. S. Wong, Chemistry of Protein Conjugation and Cross-Linking, CRC Press (1991).

Chemical linking may include the use of spacer arms. Spacer arms provide intramolecular flexibility or adjust intramolecular distances between conjugated moieties and thereby may help preserve biological activity. A spacer arm may be in the form of a polypeptide moiety comprising spacer amino acids. Alternatively, a spacer arm may be part of the cross-linking reagent, such as in "long-chain SPDP" (Pierce Chem. Co., Rockford, Ill., Cat. No. 21651H).

For linking two polypeptides, additional linking techniques are available. For example, recombinant techniques can be used to covalently attach an internalizing polypeptide sequence to a polypeptide payload, such as by joining the gene coding for the payload with the gene coding for an internalizing polypeptide sequence and introducing the resulting gene construct into a cell capable of expressing the conjugate. Alternatively, the two separate nucleotide sequences can be expressed in a cell or can be synthesized chemically and subsequently joined, using known techniques, or the combined sequence maybe synthesized chemically as a single amino acid sequence (i.e., one in which both constituents are present) thus obviating any subsequent joining.

Imaging agents may be incorporated by covalent bonding directly to an atom of R', or the label may be non-covalently or covalently associated with a targeting or therapeutic moiety through a chelating structure or through an auxiliary molecule such as mannitol, gluconate, glucoheptonate, tartrate, and the like. When a chelating structure is used to provide spatial proximity between a label and a targeting or therapeutic moiety, the chelating structure may be directly associated with the construct or it may be associated with the construct through an auxiliary molecule such as mannitol, gluconate, glucoheptonate, tartrate, and the like.

Any suitable chelating structure may be used to provide spatial proximity between the radionuclide and the cyanoacrylic core through covalent or non-covalent association. Many such chelating structures are known in the art. Preferably, the chelating structure is an $N_2S_2$ structure, an $NS_3$ structure, an $N_4$ structure, an isonitrile-containing structure, a hydrazine containing structure, a HYNIC (hydrazinonicotinic acid)-containing structure, a 2-methylthiolnicotinic acid-containing structure, a carboxylate-containing structure, or the like. In some cases, chelation may be achieved without including a separate chelating structure, because the radionuclide chelates directly to atom(s) in a targeting or therapeutic moiety, for example to oxygen atoms in various moieties.

Radionuclides may be placed in spatial proximity to the cyanoacrylic core using known procedures which effect or optimize chelation, association, or attachment of the specific radionuclide to ligands. For example, when $^{123}I$ is the radionuclide, the imaging agent may be labeled in accordance with known radioiodination procedures such as direct radioiodination with chloramine T, radioiodination exchange for a halogen or an organometallic group, and the like. When the radionuclide is $^{99m}Tc$, the imaging agent may be labeled using any method suitable for attaching $^{99m}Tc$ to a ligand molecule. In certain embodiments, when the radionuclide is $^{99m}Tc$, an auxiliary molecule such as mannitol, gluconate, glucoheptonate, or tartrate is included in the labeling reaction mixture, with or without a chelating structure. In other embodiments, '"Tc is placed in spatial proximity to the cyanoacrylic core by reducing $^{99m}TcO_4$, with tin in the presence of mannitol and the cyanoacrylic core. Other reducing agents, including tin tartrate or non-tin reductants such as sodium dithionite, may also be used to make an imaging agent of the invention such as a cardiovascular imaging agent.

In general, labeling methodologies vary with the choice of radionuclide, the moiety to be labeled and the clinical condition under investigation. Labeling methods using $^{99m}Tc$ and $^{111}In$ are described for example in Peters, A. M. et al., Lancet 2: 946-949 (1986); Srivastava, S. C. et al., Semin. Nucl. Med. 14(2):68-82 (1984); Sinn, H. et al., Nucl. Med. (Stuttgart) 13:180, 1984); McAfee, J. G. et al., J. Nucl. Med. 17:480-487, 1976; McAfee, J. G. et al., J. Nucl. Med. 17:480487, 1976; Welch, M. J. et al., J. Nucl. Med. 18:558-562, 1977; McAfee, J. G., et al., Semin. Nucl. Med. 14(2): 83, 1984; Thakur, M. L., et al., Semin. Nucl. Med. 14(2): 107, 1984; Danpure, H. J. et al., Br. J. Radiol., 54:597-601, 1981; Danpure, H. J. et al., Br. J. Radiol. 55:247-249, 1982; Peters, A. M. et al., J. Nucl. Med. 24:39-44, 1982; Gunter, K. P. et al., Radiology 149:563-566, 1983; and Thakur, M. L. et al., J. Nucl. Med. 26:518-523, 1985.

Synthesized monomers and/or polymers may be characterized using standard methods of high field NMR spectra as well as IR, MS, and optical rotation. Elemental analysis, TLC, and/or HPLC can be used as a measure of purity. TLC and/or HPLC can also be used to characterize such compounds.

IV. Monomeric Compositions and Uses Therefor

The following discussion of potential uses of the subject invention are organized for convenience by the particular use being discussed, but any of the teachings for any particular use may apply as well to other uses described hereunder or otherwise known or apparent herefrom to one of skill in the art.

A. Adhesives

In certain embodiments, the present invention employs compositions which may be suitable as adhesives. In certain embodiments, the monomer composition is applied and subsequent polymerization results in formation of a polymeric formulation with sufficient tackiness and tensile strength to form an adhesive adequate for the particular application.

In certain embodiments using compositions of this invention, polymerization of the monomers is catalyzed by small amounts of moisture. This desired bonding of tissues or hemostasis proceeds well in the presence of blood and other body fluids. The bonds formed are of adequate flexibility and strength to withstand normal movement of tissue. In addition, bond strength is maintained as natural wound healing proceeds. Because adhesive may degrade and/or be sloughed off over time, a patient need not revisit a physician to remove the bond, as is often necessary with other closure methods, such as staples or sutures.

As above-mentioned, conventional surgical adhesive compositions have been applied in small quantities to tissue surfaces, e.g., of wounds, incisions, or other surfaces, before and/or after they are abutted, with care taken to remove excess adhesive. In certain instances, thick films formed on wound surfaces have, in the past, resulted in increased histotoxicity of the wound tissues and increased film brittleness with no increased film strength. In some embodiments, the present compositions may incite fewer reactions and side effects, and thus may be used more liberally.

One method of the present invention is directed to a method of joining together in vivo two tissue surfaces by applying the composition to wound surfaces and pressing the surfaces together, and/or by applying to an already abutted tissue surface of a wound or incision a composition of this invention, optionally in more than one application or coating on the abutted tissue surfaces to provide an excess of the adhesive composition on the abutted tissue surfaces. Excess adhesive applied directly on the abutted tissue surface or on the immediate vicinity of the wound or incision may be removed or not, as desired. See, e.g., U.S. Pat. Nos. 5,981,621 and 6,217,603.

Exemplary methods which may use an adhesive composition of the present invention include methods for repairing damaged living tissue to prevent the escape of fluids therethrough by (i) methods for holding damaged tissue edges together in an abutting relationship, applying to the abutting tissue the monomer composition of the present invention, and allowing the composition to polymerize as a bridge; (ii) methods for applying the adhesive composition to one or both faces of the damaged tissue, pressing the damaged tissue faces together, and allowing the monomer composition to polymerize; (iii) methods for stemming the flow of blood from vessels by holding damaged regions of the blood vessels together, applying the present monomer composition to the damaged regions and allowing the composition to polymerize; and (iv) methods of bonding bone tissue to promote healing of weak or fractured bones by holding damaged bone tissue together, applying to the damaged tissue the present monomer composition, and allowing the composition to polymerize. Other methods for employing the subject compositions will be apparent to one of skill in the art and are intended to fall within the scope of the present disclosure.

Repairing injured tissues may include sponging or cleaning to remove superficial body fluids, holding injured tissue surfaces together in an abutting relationship and subsequent application to the exposed abutted tissue of the present adhesive composition. The composition may polymerize to a film or coating of polymer while in contact with the abutted tissue surface. Tissues may optionally be sponged or cleaned first. More than one coating or application of monomer composition may be applied to the abutted tissue surface as necessary.

In addition to utility in dermal lesions, the present compositions can be used for uniting a wide variety of tissue types. For example, the present invention provides a technique for repairing torn or detached retinal tissue. Ophthalmic compositions comprising biocompatible, in vivo polymerizable, bioadhesive monomers as described above may be used as a patch for repairing tears in the retina or reattaching detached retinal tissue. The compositions may be relatively non-viscous on administration yet sufficiently thixotopic to prevent spontaneous dislocation. Certain compositions which result in a relatively rigid polymer may be useful for retinopexy techniques, while more flexible compositions, such as those which include plasticizers, may be useful for establishing a bond with physical characteristics more similar to the retinal tissue itself. Criteria for selecting a suitable monomer for this and other applications will be readily apparent to one of skill in the art.

Depending on the particular requirements of the user or circumstance, adhesive compositions of this invention may be applied by known means such as with a glass stirring rod, sterile brush, medicine dropper, or other applicator. However, in certain situations, a pressurized aerosol dispensing package may be employed in which the adhesive composition is in solution with a compatible anhydrous propellant. Additional techniques and applications may be found in U.S. Pat. Nos. 5,928,611, 6,099,807, 6,283,933, 5,254,132, 3,654,239 and PCT No. WO 93/25196. Suitable film thickness for adhesive applications range from about 0.1 mm or less to about 2.0 mm or about 3.0 mm or higher, or from about 0.2 mm to about 1.5 mm, or from about 0.4 mm to about 0.8 mm. See also U.S. Pat. No. 5,981,621.

More than one coating of a monomer may be used as necessary. A subsequent coating may be applied immediately after application of a previous coating or after a previous coating has been completely polymerized. In certain circumstances, the monomer composition applied to the abutted tissue surface is allowed to at least partially polymerize prior to subsequent coatings or applications of additional monomer composition. A coating of an adhesive composition of the present invention having a monomer different from the monomer of the first or previous coating may be applied as the second or subsequent coating. The addition of a plasticizing agent and/or stabilizing agent to the monomer composition may alter the properties of the monomer, the resulting polymer, or the polymerization process. For example, a plasticizer may imbue the polymer formed on the abutted tissue surface with sufficient bond strength and flexibility even with significant film or coating thicknesses.

As is evident from the discussion above, the subject adhesive compositions may include one or more therapeutic agents. Additionally or alternatively, biologically active compounds may be included in the monomers themselves, e.g., in the R' portion bound to the cyanoacrylic core. In this way, infection or inflammation of a wound or other defect may be inhibited as the wound is closed.

As may be necessary or preferred to treat any wound, other materials discussed above may be included in the subject adhesives.

B. Therapeutic Films

In certain embodiments, it may be desirable to treat skin or other tissue with a monomer composition, optionally comprising one or more materials discussed above. Such a composition may be applied to wounds, incisions, abrasions, sores or other openings in tissue, or to tissue which is unbroken, e.g., which is not the site of a wound, incision or other type of cleavage. For example, such films have been used to treat dermatoses, as described in U.S. Pat. No. 5,962,010. Such a coating may also be used internally, e.g., in the treatment or prevention of restenosis, abrupt reclosure, or vasospasm after vascular intervention. In certain embodiments, the use of a plasticizer in the composition may facilitate the maintenance of the polymeric film in an unbroken manner and may inhibit cracking of the film.

The application protocol may involve tissue preparation prior to formation of the polymer film over the tissue surfaces which typically comprises washing the tissue, preferably with a soap solution. The tissue may be dried and then an adherent polymeric film formed over the tissue by applying a subject monomer composition to the tissue surface.

Polymerization may occur at ambient tissue temperature while maintaining the tissue surface under suitable conditions to allow polymerization to proceed. In general, the particular length of time required for polymerization will vary depending on factors such as the amount of composition applied, the temperature of the tissue, the moisture content of the tissue, the surface area of tissue to which the composition is applied, and the like. In a preferred embodiment, polymerization is generally complete within about 10 to about 60 seconds while the tissue is maintained at ambient conditions. During this period, the patient may be maintained in a position which permits the subject monomer to polymerize and form a polymeric film while minimizing any patient movement that might dislodge the monomer or create undesirable bonding.

After polymerization, the resulting polymeric film in certain embodiments strongly adheres to the tissue, and is flexible and waterproof, thereby forming an occlusive layer over the tissue. Strong adherence reduces the possibility that the film will separate from the patient's tissue. However, notwithstanding such adherence, the polymeric film may only adhere to the tissue for a period of about 1-4 days after which time it sloughs off. This occurs because the cyanoacrylic polymer adheres only to the uppermost portion of the epidermal layer which is continuously in the process of being sloughed off and replaced by the underlying cells. Accordingly, additional cyanoacrylic monomer composition may be applied to the tissue if it is desired to maintain the polymeric film over the tissue and continue treatment with the active agent. Alternatively, because in part of this sloughing, a patient treated with such a film need not visit a physician to cease treatment or have the film removed.

In one embodiment, after an initial polymeric film is formed, a second, optionally thinner, coating of a subject monomer composition is applied thereto. Additional amounts of monomer composition may be applied as needed to maintain an unbroken coating over the tissue.

A suitable polymeric film may have a thickness of less than about 1 millimeter, and alternatively from about 2 to about 500 microns, and alternatively from about 20 to about 100 microns. If thinner polymeric films are desired, then the polymeric film may have a thickness of from about 2 to about 50 microns or from about 10 to 40 microns. Thicker films may be applied in one or more layers, and films of 0.2 mm and higher are preferred for some applications. Useful thicknesses are disclosed in U.S. Pat. No. 5,981,621 to Clark et al. Determination of the amount of subject monomer composition applied to a unit area of tissue to obtain such thicknesses is well within the skill of the art.

The cyanoacrylic monomer composition may be provided as a sterile solution or may be sterilized as needed. Preferred sterilization techniques are disclosed, for example, in U.S. Pat. No. 6,143,805 to Hickey et al. and PCT Publication No. WO 01/12243.

A variety of materials discussed above may be incorporated into the polymeric film to achieve certain desirable characteristics. For example, in embodiments, the cyanoacrylic monomer composition comprises a compatible antimicrobial agent to provide antimicrobial properties to the composition.

In embodiments, the cyanoacrylic monomer composition comprises a therapeutically effective amount of an antimicrobial agent which serves to inhibit microbial infection of the treated tissue during the healing process. Preferably, the cyanoacrylic monomer compositions comprise from about 1 to about 40 and more preferably 5 to 30 weight percent of the compatible antimicrobial agent either as a solution or as a suspension based on the total weight of the composition. In certain embodiments, compatible antimicrobial agents are those which are either soluble or suspendable in the monomer composition, which do not cause premature polymerization or prevent polymerization of the monomer composition when applied to tissue, and which are compatible with the intended use including biocompatibility with the tissue. Suitable antimicrobial agents are further discussed above.

In embodiments, the cyanoacrylic monomer composition comprises a therapeutically effective amount of a corticosteroid. The corticosteroid is released from the resulting polymeric film formed in situ on the tissue and serves to medicate the surrounding area and decrease discomfort such as itching, while facilitating healing. In preferred embodiments, the subject monomer compositions comprise from about 0.1 to about 25 weight percent of the corticosteroid as a solution, emulsion, or suspension based on the total weight of the composition.

The use of a corticosteroid in the composition permits the steroid to be gradually released from the polymeric film thereby reducing inflammation under the film as well as to facilitate healing of the tissue. Because the film is maintained over the tissue after formation, controlled release of the steroid is achieved without the need to reapply the steroid at more frequent intervals.

C. Preparative Films

Compositions of the invention may also be useful in preparation for a wound or incision. Reducing morbidity and/or infection associated with surgical procedures necessitates the thorough preparation of the patient's skin prior to initiating any incision into the skin as part of the surgical procedure. The primary reason for patient skin preparation is to reduce the risk of wound infection by introduction of microbes into the incision site (Masterson, M. D., "Skin Preparation," Chapter 9, in Surgical Infections, Diagnosis and Treatment, Meakins, Ed., Scientific American, Inc., New York, USA, pp. 119-125 (1994)) from either the skin or from the air (Duhaime, et al., "Distribution of Bacteria in the Operating Room Environment and its Relation to Ventricular Shunt Infections: a Prospective Study," Child's Verv. Syst., 7:211-214 (1991)). In turn, reduction in such risk correlates, obviously, with reductions in the population of microbes on the skin surface and especially at the skin surfaces adjacent to the incision site.

Suitable skin preparation involves, for example, application of a therapeutic agent such as an antimicrobial agent onto and around the skin surfaces adjacent to the incision site, which reduces the population of microbes on these surfaces and, hence, the relative risk of infection. However, the skin is never completely sterilized during these procedures and microbes from hair follicles and sweat/sebaceous glands may migrate to the surface of the skin thereby raising microbial populations and accordingly relative infection risks. (Osuna, et al., "Comparison of an Antimicrobial Adhesive Drape and Povidone-Iodine Preoperative Skin Preparation in Dogs," Veterinary Surgery, 21(6):458-462 (1992)) To counter possible microbial migration into the incision, it has become common practice to employ a surgical drape, where practicable, over the patient's incision site.

Conventional surgical drapes include those which comprise preformed, sized polymeric films coated with a pressure-sensitive adhesive. In some cases, an antimicrobial agent is incorporated directly into the adhesive in order to permit a continuous release of the antimicrobial agent onto the skin. (Hagen, et al., "A Comparison of Two Skin Preps Used in Cardiac Surgical Procedures," AORN Journal, 62(3):393-402 (1995); O'Sullivan, et al., U.S. Pat. No. 4,038,345). After application of an antimicrobial agent onto the skin surface of the patient, the surgical drape is applied, adhesive side down, with pressure to effect adherence of the drape to the skin. A surgical incision is then made through the drape and the requisite surgery is conducted through this incision. After completion of the surgery, the drape is conventionally removed from the skin surface prior to final incision closure.

Compositions described herein are useful in forming a polymeric surgical drape peripheral to or surrounding the surgical site of a patient. The polymeric drape finds particular utility in inhibiting microbial contamination of the incision during surgeries conducted on such patients. Such patients include, for example, humans as well as animals such as horses, cows, dogs, sheep, cats, etc. The maintenance of the polymeric film peripheral to the surgical incision after completion of the surgery is expected to reduce the incidence of infection by inhibiting microbial contamination of the incision.

The use of a compatible antimicrobial agent in the composition permits the agent to be gradually released from the polymeric drape thereby reducing microbial growth under the drape during surgery. Additionally, the compatible antimicrobial agent in the composition may migrate from the drape to the incision site and reduce microbial contamination at the incision site. Because the drape remains for some time after surgery, the continued release of antimicrobial agent may further provide post-surgical anti-infection benefits.

In certain embodiments, it may be desirable to dispose such a film adjacent to the site of incision, rather than at the site of incision, to take advantage of the continuous release into the vicinity of the incision while reducing the opportunity for portions of the film to migrate under the skin, particularly where the film contains a biologically active agent suitable for the surface of the skin, but which may promote an undesirable reaction internally.

Other known uses of cyanoacrylic polymer films include their use to prevent friction blister formation (Barley, U.S. Pat. No. 5,306,490) and to inhibit surface skin irritation arising from friction between the skin surface and artificial devices such as tapes, prosthetic devices, casts, and the like. (Barley, et al., U.S. Pat. No. 5,653,789).

D. Sealants

In numerous embodiments, the subject compositions may be used for blocking off a biological pore, channel, artery, or vessel, to inhibit leakage, unwanted discharge, or other undesirable transport of fluids.

1. Blocking the Canaliculus

Mammalian eyes include a complex composition in the form of a tear film. Tears include three basic component layers comprising (1) lipids, (2) an aqueous layer, and (3) mucin. The absence of any one of the layer components causes discomfort and can lead to temporary or permanent dry eye syndromes (SICCA). Each of the component layers has a particular function. The lipid layer prevents evaporation of the tears from the surface of the eye. The aqueous layer is the major component of the tears, and is responsible for providing oxygen to the cornea and contains a number of additional chemical components which are important to a healthy eye. The mucin material provides for interaction between the lipid layer and the aqueous layer and keeps the tears from beading up on the cornea, which will occur in the absence of mucin.

The importance of a tear layer on a healthy mammalian eye may be generally understood based on the above explanation. However, from time to time the eye suffers from a lack of tears (dry eye), which can have a variety of causes but is generally attributed to one or two basic malfunctions. First, the tear ducts leading from the lacrimal glands can be clogged or malfunctioning so that insufficient amounts of tears reach the eye. This was generally thought to be the main reason for dry eye for a considerable period of time. In response, artificial tears were developed and administered to eyes. The relief enjoyed by these tears are short-lived and they must be re-administered several times each hour. More recently, it has been noted that most tear producing glands can deliver sufficient amounts of tears to the eye, but that the tears are drained away from the eye too quickly, thereby creating a dry eye situation. Accordingly, recent therapies have proceeded on the basis that tear production is adequate in most individuals, and that a significant percentage of dry eye syndrome is caused by excessive tear removal.

Tears are removed from the eye by draining first through upper and lower punctal openings which lead into the canalicular canals. Initial attempts at sealing the puncta and/or the canalicular canals involved stitching the puncta shut or using electrical or laser cauterization to seal the puncta and or canalicular canals. Although such methodology may provide desirable results, the procedure is not reversible without reconstructive surgery. Because it is sometimes difficult to determine whether the drainage is too great or the tear production is too small, irreversible blockage is a condition which is not without risk. If tear production is completely eliminated, it will not solve the problem and the patient would have been exposed to unnecessary expense and trauma. Alternatively, it may result in a situation where normal tear flow is restored and tears continually form on the eye, build up and pour onto the face of the patient (epiphera).

Compositions of the present invention may be used for temporary blockage of a canalicular canal to alleviate this condition in a reversible manner. Subsequent applications may be employed to renew or continue a blockage for extended treatment.

2. Closing Off a Blood Supply

In the case in which a patient has developed a tumor in an organ that is inaccessible or the organ is of a nature or in a position that prevents a surgical approach, a method to rid the host of the problem may be to cut off the blood supply and starve the unwanted growth. Rapidly polymerizing monomers such as certain cyanoacrylics of the present invention may be deposited in the appropriate vessel by means of an appropriately guided cannula or catheter. When the end of the catheter is in the proper position, the subject monomer is released. Once exposed to the multitudinous supply of nucleophilic natural agents, the monomer polymerizes and effects blockage.

When a patient has developed an uncontrolled hemorrhage in, perhaps, the brain, there is often too much risk associated with surgical intervention. The safest way to arrive at the site of hemorrhage is again by a fine guided catheter. A rapidly polymerizing monomer such as made available by embodiments of the present invention, may be deposited in the appropriate vessel at the site of hemorrhage to stem the blood flow and prevent stroke or ischemia.

Furthermore, the compositions may be employed for external injuries, such as scrapes or severe burns, to reduce blood loss and risk of infection by topical application of the monomer composition to the affected area.

3. Correction of Vascular Abnormalities

A condition known as arteriovenous anastomosis (the joining of an artery and a vein) is a serious problem because anastomosis bypasses the intended capillary bed, thus starving the cells fed by that system. Once recognized, a surgeon may attempt appropriate measures to correct the condition. Closing off the abnormality by surgery is possible if the area can be accessed, but guided catheterization is used when the identified anastomosis is remote or inaccessible. Gelling agents are used but they are normally difficult to repair because of the high flow rate through the abnormality. A monomer which polymerizes with a quick set time, such as certain embodiments of the compositions described herein, may be used to create a plug for the anastomosis which encourages growth of new tissue over the unwanted opening.

4. Sterilization

As described in U.S. Pat. No. 5,989,580, biocompatible polymeric blockages may be formed in the fallopian tubes to block the passage of eggs into the uterus. Compositions of the invention may be used for this purpose. The process may be reversed by the application of a suitable solvent or digestive agent, or the blockage may simply be permitted to degrade over time, thereby providing a temporary, reversible means of sterilization that does not depend on invasive procedures or regular administration of hormonal supplements.

5. Sealing a Channel Created By a Medical Procedure

In certain embodiments, the present compositions may be used to block channels created during an invasive medical procedure. For example, a temporary cranial tap creates an opening to permit the release of pooled blood between the brain and the skull after a concussion. After the pressure is reduced, the hole must be sealed to prevent the passage of other fluids or introduction of bacteria. A quantity of subject cyanoacrylic monomer may be disposed in the channel, e.g., to block bloodflow, passage of infectious agents, etc., while the channel heals shut. Similarly, openings created from catheters, laparoscopic surgery, biopsies, or other puncture wounds may be treated with cyanoacrylic monomers of the present invention. As for all of these applications discussed herein, the particular monomer necessary for this use can have properties customized to the particular use.

6. Securing Medical Devices

Compositions of the invention may also be used to secure medical devices to a patient. For example, a breathing tube, feeding tube, catheter, or catheter guide may be secured to an opening in a patient's skin to inhibit accidental dislodging. Similarly, electrode patches or transdermal drug delivery patches can be temporarily affixed to a patient's body, or other devices can be secured to a location in or on a patient.

Broken bones are frequently supported by steel pins, e.g., placed within the natural lumen of a finger or limb bone. Hip joint replacements often require that a new ball fitting be placed at the end of the femur by means of a pin or spike. This spike enters the lumen of the femur. In either case, if the fit is not tight, a cyanoacrylic monomer of the present invention may be used to fill in the space between the pin and the bone and to keep the pin in position and prohibit it from moving within the lumen.

Various modifications and supplements useful for the applications described above may be useful in applications other than those specifically mentioned. The present invention specifically contemplates such combinations and modifications and their use in any of the applications discussed above or which may be apparent to those of skill in the art.

V. Polymeric Compositions and Uses Therefor

A. Controlled-Release Delivery

In addition to the drug-delivery applications discussed above, polymers formed from the subject monomers may be used to administer a payload to a patient by incorporating the material within the polymer and disposing the polymer within the patient. Alternatively or additionally, as described above, a payload may be covalently bound to the cyanoacrylic core, e.g., as the R' group. As the polymer biodegrades within the body, the compound will gradually be released into the patient.

In general, there are often a number of advantages observed for the controlled release of a therapeutic agent as compared to other modes of administration, and some of these advantages may be realized in embodiments of the present invention. For example, controlled release generally decreases the toxic side effects associated with systemic administration of a nonencapsulated agent. Also, a polymeric matrix may provide protection of the agent against degradation in the plasma for drugs with short half-lives under physiological conditions.

Exemplary strategies for preparing and using polymeric materials, including particles, of the present invention are discussed below.

B. Particles of the Subject Polymers, and Methods of Using the Same

For controlled drug delivery, small particles, such as nanoparticles and/or microparticles, or any other polymer formation may be used. The preparation and use of particles, especially cyanoacrylic-based particles, is discussed in detail in Vauthier et al., *Proceed. Intern. Symp. Control. Rel. Bioact. Mater.* 1995, 22, 592-593; Tuncel et al. *J. Biomed. Mater. Research* 1995, 29, 721-728; Peracchia et al. *J.*

*Biomed. Mater. Research* 1997, 34, 317-326; and Hillery et al. *J Controlled Release* 1996, 42, 65-73. Features of particles of the present invention are presented below. Persons of ordinary skill of the art will be able to apply these teachings as appropriate to other physical configurations of the subject polymers.

1. Composition of Particles

As described above, particles are formed from polymers of the subject monomers. In certain embodiments, the particles may comprise a mixture of polymers, or a copolymer of the subject monomers with other suitable monomers. The period of time of release, and kinetics of release of the incorporated material from a particle may vary based on a variety of factors, including the copolymer or copolymer mixture or blend selected to fabricate the particle. Given the disclosure herein, those of ordinary skill in this art will be able to select the appropriate polymer or combination of polymers to achieve a desired effect.

Generally, a mixture of the monomer and the compound, optionally including plasticizers, stabilizers or other materials discussed above, may be polymerized to yield a polymer having the compound incorporated in the matrix.

2. Structure of Particles

The shape of particles prepared according to the procedures herein or otherwise known is easily determined by scanning electron microscopy. Spherically shaped nanoparticles are preferred for circulation through the bloodstream. If desired, the particles may be fabricated using known techniques into other shapes that are more useful for a specific application.

In addition to intracellular delivery of a delivery agent that may be mediated by a delivery agent after release from the subject particles, it also possible that particles of the present invention may undergo endocytosis, thereby obtaining access to the cell. The frequency of such an endocytosis process will depend on the size of any particle.

3. Substances to be Incorporated into Particles

A wide range of biologically active materials or drugs can be incorporated onto or into particles, including therapeutic agents, imaging agents, targeting agents and the like. The materials to be incorporated may be selected not to interact chemically with the polymer during fabrication, or during the release process. Other materials, such as additives, inorganic salts and inert organic compounds like those discussed above may be used to alter the profile of substance release, as known to those skilled in the art. In addition, biologically labile materials, for example, prokaryotic or eukaryotic cells, such as bacteria, yeast, or mammalian cells, including human cells, or components thereof, such as cell walls, or conjugates of cellular material may also be included in a particle (or any subject polymeric formulation).

By way of example, a number of embodiments in which different agents are incorporated into polymer formulations and particles of the present invention are set forth below. For example, in one embodiment, an antigen is incorporated into a nanoparticle. The term antigen includes any chemical structure that stimulates the formation of antibody or elicits a cell-mediated humoral response, including but not limited to protein, a protein produced by a nucleic acid, polysaccharide, nucleoprotein, lipoprotein, synthetic polypeptide, or a small molecule (hapten) linked to a protein carrier. The antigen may be administered together with an adjuvant as desired. Examples of suitable adjuvants include synthetic glycopeptide, muramyl dipeptide. Other adjuvants include killed *Bordetella pertussis*, the liposaccharide of Gram-negative bacteria, and large polymeric anions such as dextran sulfate. A polymer, such as a polyelectrolyte, may also be selected for fabrication of the particle that provides adjuvant activity.

Specific antigens that may be loaded into particles described herein include, but are not limited to, attenuated or killed viruses, toxoids, polysaccharides, cell wall and surface or coat proteins of viruses and bacteria. These antigens may also be used in combination with conjugates, adjuvants or other antigens. For example, *Haemophilus influenzae* in the form of purified capsular polysaccharide (Hib) may be used alone or as a conjugate with diphtheria toxoid. Examples of organisms from which these antigens are derived include poliovirus, rotavirus, hepatitis A, B, and C, influenza, rabies, HIV, measles, mumps, rubella, *Bordetella pertussus, Streptococcus pneumoniae, C. diphtheria, C. tetani, Cholera, Salmonella, Neisseria*, and *Shigella*. Such particles may be used to provoke an immune response, e.g., for immunization. Use of nucleic acid-containing particles is discussed in greater detail below.

Non-pharmaceutical uses for injectable particles include delivery of food additives, including stabilizers and dispersants or other viscosity modifying agents, controlled and selective delivery of pesticides, herbicides, insecticides, fertilizer, and pheromones, and in color and ink formulations in the printing and ink industry.

In another embodiment, a gamma-labeled injectable particle is provided that may be used to monitor the biodistribution of the injectable particle in vivo. Any pharmaceutically acceptable gamma-emitting moiety may be used, including but not limited to indium and technetium. Magnetic particles may also be prepared as described herein, or alternatively, magnetic particles, including surface-modified magnetic particles, may be purchased commercially, and coated with a cyanoacrylic polymeric coating as described herein.

Other materials may also be incorporated into the injectable particles for diagnostic purposes, including radiopaque materials such as air or barium and fluorescent compounds. Fluorescent compounds such as rhodamine may be incorporated into the core of the particles.

In embodiments, the particles include a substance to be delivered and a polymer coating that is covalently bound to a targeting molecule that targets a certain type of tissue or pathological site, for example, an antibody or antibody fragment, such as Fab or $Fab_2$ antibody fragments, wherein the particle is prepared in such a manner that the biologically active molecule is on the outside surface of the particle.

The particles prepared as described herein may be used for cell separation, or may be targeted to specific tissues, by attaching to the surface of the particle specific ligands for given cells in a mixture of cells. In this manner, the compound in the particle may be delivered preferentially to particular sites in the body, even when a non-specific mode of delivery is employed. When magnetic particles are also incorporated, the particles may be targeted using ligands, such as tissue specific receptors or antibodies to tissue specific surface proteins, then maintained at the targeted cells using a magnetic field while the particles are imaged or a compound to be delivered is released. For example, in one embodiment, carmustine (BCNU) or other anti-cancer drug or agent, such as cis-platin, is incorporated into the injectable particles and antibodies to target cancerous cells are covalently bound to the surface of the injectable particle.

4. Release Rate from Particles

The release rate from particles will vary with different embodiments of the present invention. For example, one subject formulation may require at least an hour to release a major portion of the active substance into the surrounding medium, whereas another formulation may require about 1-24 hours, or even much longer. In certain embodiments, such release may result in release (over, say 1 to about 2,000 hours, or alternatively about 2 to about 800 hours) of the therapeutic agent or other material encapsulated in subject particles. In certain embodiments, such substance or other material may be released in an amount sufficient to produce a therapeutically beneficial response.

The release profile of any therapeutic agent or other material from a polymer particle of the present invention may vary in different embodiments. In one embodiment of the present invention, the therapeutic agent or other material is released from the particle in a pulsatile manner. For example, such a pulsatile manner may involve release of the therapeutic agent or other material in three phases: an initial burst, a slow release, and a second burst. In another embodiment of the present invention, the therapeutic agent or other material is released in a sustained manner. In still other embodiments, a significant portion of the therapeutic agent or other material is released in an initial phase. In still other embodiments, the release profile is bi-phasic.

Other materials may be used to advantage to control the desired release rate of an agent for a particular treatment protocol. For example, if the resulting polymer is too impervious to water, a pore-forming agent may be added to generate additional pores in the matrix. Any biocompatible water-soluble material may be used as the pore-forming agent. These agents can be either soluble in the liquid composition or simply dispersed within it. They are capable of dissolving, diffusing or dispersing out of both the coagulating polymer matrix and the formed polymer system whereupon pores and microporous channels are generated in the matrix and system. The amount of pore-forming agent (and size of dispersed particles of such pore-forming agent, if appropriate) within the composition should affect the size and number of the pores in the polymer system.

Pore-forming agents include any pharmaceutically acceptable organic or inorganic substance that is substantially miscible in water and body fluids and will dissipate from the forming and formed matrix into aqueous medium or body fluids or water-immiscible substances that rapidly degrade to water-soluble substances. Suitable pore-forming agents include, for example, sugars such as sucrose and dextrose, salts such as sodium chloride and sodium carbonate, and polymers such as hydroxylpropylcellulose, carboxymethylcellulose, polyethylene glycol, and polyvinylpyrrolidone. The size and extent of the pores may be varied over a wide range by changing the molecular weight and percentage of pore-forming agent incorporated into the polymer system.

The release of any therapeutic agent or other material herein may be determined using in vitro assays. One such assay that is known in the art involves degradation of any subject polymer in a 0.1 M PBS solution (pH 7.4) at 37° C. For purposes of the present invention, the term "PBS protocol" is used herein to refer to such protocol.

In certain instances, the release rates of different embodiments of the present invention may be compared by subjecting them to the same assay. In certain instances, it may be necessary to process the particles in the same fashion to allow direct and relatively accurate comparisons of different embodiments to be made. Such comparisons may indicate that any one embodiment releases incorporated therapeutic agents or other material at a rate from about 2 or less to about 1000 or more times faster than another embodiment. Alternatively, a comparison may reveal a rate difference of about 3, 5, 7, 10, 25, 50, 100, 250, 500 or 750. Even higher rate differences are contemplated by the present invention.

The release rate of any therapeutic agent or other material may also be characterized by the amount of such substance or other material released per day per mg of polymer particle. For example, in certain embodiments, the release rate may vary from about 1 ng or less of any such substance or other material per day per mg of polymer to about 5000 or more ng/day/mg. Alternatively, the release rate may be about 10, 25, 50, 75, 100, 125, 150, 175, 200, 250, 300, 350, 400, 450, 500, 600, 700, 800 or 900 ng/day/mg. In still other embodiments, the release rate of any incorporated material may be 10,000 ng/day/mg or even higher.

In those embodiments of the present invention in which a virus is encapsulated in the subject particles, so that the therapeutic agent is a nucleic acid of interest contained in a viral vector and a delivery agent is the virus particle, the release rate may also be quantified by "PFU," or plaque forming units. In such embodiments, PFUs designate the number of infectious virions. This unit only quantifies those viruses or virus particles that are bioactive, whereas the mass measurement described above counts both bioactive and non-bioactive viruses or viral particles. In certain embodiments, the range of PFUs that any subject polymer may release over any particular time period may range from less than about 100 PFUs to more than about $10^9$ PFUs.

In another aspect, the rate of release of any therapeutic agent or other material from any particle of the present invention may be presented as the half-life of such substance or other material in such polymeric particle.

In addition to the embodiment involving protocols for in vitro determination of release rates, in vivo protocols, whereby release rates for different polymer particles may be determined in vivo, are also contemplated by the present invention. Comparisons of release rates for different embodiments of the subject particles and polymers may be made for in vivo assays in a similar manner as for in vitro assays. Other assays useful for determining the release rate of any polymer of the present invention are known in the art.

5. Modification of Surface Properties of Particles

The charge, lipophilicity or hydrophilicity of the particle may be modified by attaching an appropriate compound to the hydrophilic polymer on the surface of the particle. The particle may also be coated with a dextran, which is relatively hydrophilic. Dextran-coated nanoparticles may be useful for magnetic resonance imaging (MRI).

6. Pharmaceutical Administration and Dosage of Particles

Particles described herein may be administered to a patient in a variety of routes, for example, orally, parenterally, intravenously, intradermally, subcutaneously, or topically, in liquid, cream, gel or solid form. Controlled delivery devices prepared as described herein may also be used as ocular inserts for extended release of drugs to the eye.

The particles may be lyophilized and then formulated into an aqueous suspension, for example, in a range of about 1 microgram/ml or less to 100 mg/ml or more prior to use. Alternatively, the particles may be formulated into, for example, a paste, ointment, cream, or gel or transdermal patch.

In most embodiments, the particle will contain the substance to be delivered in an amount sufficient to deliver to a patient a therapeutically effective amount of an incorporated compound or other material as desired. The desired concentration of active compound in the particle will depend on absorption, inactivation, and excretion rates of the drug as well as the delivery rate of the compound from the particle. Dosage values may also vary with the severity of the condition to be alleviated. Further, for any particular subject, specific dosage regimens should be adjusted over time according to the individual need and the professional judgment of the person administering or supervising the administration of the compositions.

The particles may be administered once, or may be divided into a number of smaller doses to be administered at varying intervals of time, depending in part on the release rate of the particle and the desired dosage.

The foregoing description of administration of particle of the subject polymers applies to administration of subject polymers in other shapes and configurations as well.

7. Methods of Making Particles

The method of preparing the particles should be selected to provide a particle having the desired size for the intended use. In certain embodiments, in which injectable particles capable of passing through the pulmonary capillary bed are prepared, the particles should have a diameter of between approximately one and about seven microns. Larger particles may clog the pulmonary bed, and smaller particles may not provide sufficient echogenicity. Larger particles may be useful for administration routes other than injection, for example oral (for evaluation of the gastrointestinal tract) or by inhalation. Particles including nanoparticles and microparticles may generally be prepared by the methods set forth below.

a. Preparation of a Polymer Solution

In certain embodiments, particles are, prepared by the following procedure: the polymer is dissolved or dispersed into a solution which is then sprayed into a solution of cross-linking counterions. This solution is typically an aqueous solution or dispersion that may include water-miscible organic solvents, including but not limited to dialkyl sulfoxides, such as dimethyl sulfoxide (DMSO); dialkyl formamides, such as dimethyl formamide (DMF); $C_{1-5}$ alcohols, such as methanol and ethanol; ketones such as acetone and methyl ethyl ketone; and ethers such as tetrahydrofuran (THF), dibutyl ether and diethyl ether. The solution may be neutral, acidic or basic, and may contain salts or buffers. If a polymer that is ionic is insoluble in water, or insufficiently dispersible, the polymer may be converted to its conjugate acid or base that is typically more water soluble, and that conjugate acid or base may then be exposed to the di- or multivalent counterion for cross-linking.

b. Gases to be Incorporated

The ratio of polymer to gas is determined based on the gas that is to be incorporated, for example, as required to produce a particle size small enough to be injected. Any desired inert gas may be incorporated into the polymeric materials at the time of hydrogel formation, including air, argon, nitrogen, carbon dioxide, nitrogen dioxide, methane, helium, neon, oxygen and perfluorocarbon. Sterilized air or oxygen is often used for an imaging contrast agent.

c. Atomization of Polymer Solution into a Cross-Linking Solution

There are a variety of methods for the preparation of injectable particles, two of which are described below. In one method, a jet head is used that allows the co-extrusion of a solution of polymer and air to produce nascent microencapsulated air bubbles which fall into a hardening solution of counterions. A second method employs ultrasound to introduce cavitation-induced bubbles into the polymer before capsule formation by spraying. To incorporate gases other than air, a solution of the desired polymer is placed in an atmosphere of the desired gas and sonicated for a sufficient amount of time before cross-linking to ensure that gas bubbles are dispersed throughout the particulates. In either case, the determining factors on size of resulting microparticles will be the selection and concentration of polymer and solvent, and size of droplets formed by the atomizer.

d. Preparation of One to Ten Micron Microparticles

An example of an air-atomizing device is a Turbotak, from Turbotak, Inc., Waterloo, Ontario. A Turbotak is a hollow stainless steel cylinder, 2.64 cm wide×4 cm long. Liquid is fed into the Turbotak from the top and pressurized air is fed from the side. The pressurized air mixes with the liquid, forcing tiny liquid droplets out through the orifice of the nozzle. The air pressure can be set to between 50 and 80 psig. The distance between the orifice of the Turbotak and the pan containing the cross-linking ions is fixed at between about one to two feet. The size of the nozzle orifice is 1 to 2 mm in diameter.

Air may be pressurized, for example, with a syringe pump such as a Razel pump, having a flow rate in the range of between 5 ml/hr and 30 ml/hr or a Sage pump, having a flow rate in the range of between 0.02 ml/min and 126 ml/min.

Mixing pressurized air with a polymer solution aerates the polymer solution and produces a high yield of air-encapsulated polymeric microparticles. Even without sonicating the polymer solution, microparticles produced using the Turbotak nozzle have been shown to have entrapped air, as seen by light microscopy.

e. Method for the Preparation of Larger Microparticles

Larger microparticles may be prepared using a droplet-forming apparatus by spraying an aqueous solution of polymer containing the agent of interest through an apparatus such as a plastic syringe, where the polymer solution is extruded through a needle located inside a tube through which air flows at a controlled rate.

The rate of polymer extrusion is controlled, for example, by a syringe pump. Droplets forming at the needle tip are forced off by the coaxial air stream and collected in the crosslinking solution, usually an aqueous solution of bi- or trivalent ions, where they cross-link and are hardened, for example, for between 15 and 30 minutes.

The shape and size of these particles depend on the polymer and cross-linker concentrations and parameters such as the polymer extrusion rate, air flow, and needle diameters used in the microencapsulation procedure, and can be controlled by those of ordinary skill in the art without undue experimentation.

f. Particles Formed by Cross-Linking

Particles of the subject polymers may be prepared by cross-linking. Cross-linking is possible by covalent bonds of the polymeric chains, or by other chemical interactions reactions of the polymer chains.

For example, in certain embodiments it is possible to cross-link subject polymers containing acidic side groups by using multivalent cations. Exemplary cations for cross-linking the polymers with acidic side groups to form a hydrogel are divalent and trivalent cations such as copper, calcium, aluminum, magnesium, strontium, barium, tin, chromium, and preferably zinc, although di-, tri- or tetrafunctional organic cations such as salts of nitrogenous bases, for example, alkylammonium salts, such as piperidine dihydrochloride, and salts of ethylene diamine tetra(acetic acid), can also be used. Aqueous solutions of the salts of these cations may be added to the polymers to form soft, highly swollen hydrogels and membranes. The higher the concentration of cation, or the higher the valence, the greater the degree of polymer crosslinking. Concentrations as low as 0.005 M have been demonstrated to cross-link polymers. Higher concentrations may be limited by the solubility of the salt.

In other embodiments, it is possible to cross-link subject polymers containing basic side groups with multivalent anions. Exemplary anions for cross-linking the polymers to form a hydrogel are divalent and trivalent anions such as low molecular weight dicarboxylic acids, for example, terephthalic acid, sulfate ions and carbonate ions. Aqueous solutions of the salts of these anions are added to the polymers to form soft, highly swollen hydrogels and membranes, as described with respect to cations.

In still other embodiments, it is possible to cross-link subject polymers with multivalent polymers to form a semipermeable membrane. In some embodiments, additional surface groups on the polymer are reacted with polyions of opposite charge to form a semi-permeable membrane on the surface of the hydrogel. The complexed polymer is stable and forms a semipermeable membrane on the microcapsules. The permeability of this membrane for a given entity may depend on the molecular weight of the polyion.

C. Genetic Immunization

In certain embodiments, the therapeutic agent is a nucleic acid, such as a transgene. The nucleic acid may be contained in a transfer vector, which may include regulatory elements.

For those embodiments for which the therapeutic effect of the therapeutic agent may be enhanced by intracellular delivery, such as a transgene, gene construct, expression vector or the like, a delivery agent to facilitate such delivery may also be included or encapsulated in the polymer. When the therapeutic agent is plasmid DNA, a possible delivery agent includes polylysine, polyarginine, bisguanidine cholesterol and other amphiphilic molecules. When the therapeutic agent is a nucleic acid sequence contained in a viral vector, the delivery agent is usually the virus particle corresponding to the virus in which the nucleic acid sequence is contained. Mechanisms by which these different delivery agents facilitate delivery of therapeutic agents vary.

The term "gene delivery system" refers to a type of payload incorporating the following: (i) a nucleic acid sequence encoding a sequence of interest, and (ii) a delivery agent for facilitating intracellular delivery of the nucleic acid. In certain embodiments, the nucleic acid may be operably linked to a regulatory element. In other embodiments, such nucleic acid sequence may be a transgene. In certain embodiments, the delivery agent may be a viral vector, such as an adenoviral vector, an adeno-associated viral vector or a retroviral vector.

1. Delivery Agents

In accordance with the subject invention, nucleic acids, transgenes, and the like, may be included in a subject monomer or polymer composition with any appropriate delivery agent. Approaches contemplated by the present invention include insertion of any gene or other nucleic acid of interest in viral vectors including recombinant retroviruses, adenovirus, adeno-associated virus, and herpes simplex virus-1, or recombinant bacterial or eukaryotic plasmids. Viral vectors may be used to transfect cells directly, with the virus or virus particle serving as a delivery agent; plasmid DNA or other nucleic acid may be delivered with the help of, for example, the following delivery agents: cationic liposomes (lipofectin), polylysine conjugates, polyarginine, bisguanidine cholesterol, artificial viral envelopes and other like intracellular carriers, etc. It will be appreciated that because transduction of appropriate target cells may, in certain embodiments, represent the first step in gene therapy, choice of the particular delivery agent may depend on such factors as the phenotype of the intended host and the route of administration, e.g. locally or systemically.

One approach for in vivo introduction of a gene construct, expression vector, or other nucleic acid of interest into a cell is by use of a viral vector containing a nucleic acid, e.g., a cDNA, encoding the gene product. Infection of cells with a viral vector has the advantage that a large proportion of the targeted cells may receive the nucleic acid. Additionally, molecules encoded within the viral vector, e.g., by a cDNA contained in the viral vector, are expressed efficiently in cells which have taken up viral vector nucleic acid.

In certain embodiments, the delivery agent for any viral vector is the virus or virus particle corresponding to the viral vector. Generally, such virus or virus particle envelops or encapsulate its corresponding viral vector, although the present invention contemplates that in any mixture of viral vectors, not all viral vectors will be so enveloped or encapsulated. In most instances, substantially all viral vectors in such a mixture would be so enveloped or encapsulated.

Retrovirus vectors and adeno-associated virus vectors constitute recombinant gene delivery systems able to transfer exogenous genes in vivo, particularly into humans. These vectors provide efficient delivery of genes into cells, and the transferred nucleic acids are stably integrated into the chromosomal DNA of the host. It is generally desirable in the use of retroviruses to ensure the safety of their use, particularly with regard to the possibility of the spread of wild-type virus in the cell population. The development of specialized cell lines (termed "packaging cells"), which produce only replication-defective retroviruses, has increased the utility of retroviruses for gene therapy. Such defective retroviruses are well characterized for use in gene transfer for gene therapy purposes (for a review see Miller, *Blood* 76:271 (1990)). Thus, recombinant retroviruses may be constructed in which part of the retroviral coding sequence (gag, pol, env) has been replaced by a gene or other nucleic acid of interest, rendering the retrovirus replication defective. The replication defective retrovirus is then packaged into virions which may be used to infect a target cell through the use of a helper virus by standard techniques. Protocols for producing recombinant retroviruses and for infecting cells in vitro or in vivo with such viruses may be found in *Current Protocols in Molecular Biology*, Ausubel et al. (eds.) Greene Publishing Associates (1989), Sections 9.10-9.14, diphtheria and other standard laboratory manuals. Examples of suitable retroviruses include pLJ, pZIP, pWE and pEM, which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. *Science* 230:1395-1398 (1985); Danos and Mulligan *Proc. Natl. Acad. Sci. USA* 85:6460-6464 (1988); Wilson et al., *Proc. Natl. Acad. Sci. USA* 85:3014-3018 (1988); Armentano et al., *Proc. Natl. Acad. Sci. USA* 87:6141-6145 (1990); Huber et al., *Proc. Natl. Acad. Sci. USA* 88:8039-8043 (1991); Ferry et al., *Proc. Natl. Acad. Sci. USA* 88:8377-8381 (1991); Chowdhury et al., *Science* 254:1802-1805 (1991); van Beusechem et al., *Proc. Natl. Acad. Sci. USA* 89:7640-7644 (19 1 92); Kay et al., *Human Gene Therapy* 3:641-647 (1992); Dai et al., *Proc. Natl. Acad. Sci. USA* 89:10892-10895 (1992); Hwu et al., *J. Immunol.* 150:4104-4115 (1993); U.S. Pat. No. 4,868,116; U.S. Pat. No. 4,980,286;

PCT Application WO 89/07136; PCT Application WO 89/02468; PCT Application WO 89/05345; and PCT Application WO 92/07573).

In choosing retroviral vectors as a gene delivery system for the subject polymers, it is important to note that a prerequisite for the successful infection of target cells by most retroviruses, and therefore for stable introduction of the recombinant gene, is that the target cells must be dividing. In general, this requirement will not be a hindrance to use of retroviral vectors to deliver a subject gene or other nucleic acid. In fact, such a limitation on infection may be beneficial in circumstances in which the tissue (e.g., nontransformed cells) surrounding the target cells does not undergo extensive cell division and is therefore refractory to infection with retroviral vectors.

Furthermore, it has been shown that it is possible to limit the infection spectrum of retroviruses, and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., *PNAS* 86:9079-9083 (1989); Julan et al., *J. Gen Virol* 73:3251-3255 (1992); and Goud et al., *Virology* 163:251-254 (1983)); or coupling cell surface ligands to the viral env proteins (Veda et al., *J Biol Chem* 266:14143-14146 (1991)). Coupling may be in the form of the chemical cross-linking with a protein or other variety (e.g., lactose to convert the env protein to an asialoglycoprotein), as well as by generating fusion proteins (e.g., single-chain antibody/env fusion proteins). This technique may be used to limit or otherwise direct the infection to certain tissue types, and may also be used to convert an ecotropic vector into an amphotropic vector. Moreover, use of retroviral gene delivery may be further enhanced by the use of tissue or cell-specific regulatory elements which control expression of the gene of the retroviral vector.

Another viral gene delivery system useful in the present invention utilizes adenovirus-derived vectors. The genome of an adenovirus may be manipulated such that it encodes a gene product of interest, but is inactivated in terms of its ability to replicate in a normal lytic viral life cycle (see, for example, Berkner et al., *BioTechniques* 6:616 (1988); Rosenfeld et al., *Science* 252:431-434 (1991); and Rosenfeld et al., *Cell* 68:143-155 (1992)). Suitable adenoviral vectors derived from the adenovirus strain Ad type 5 d1324 or other strains of adenovirus (e.g., Ad2, Ad3, Ad7) are well known to those skilled in the art. Recombinant adenoviruses may be advantageous in certain circumstances in that they are not capable of infecting nondividing cells and can be used to infect a wide variety of cell types, including endothelial cells (Lemarchand et al., *Proc. Natl. Acad. Sci. USA* 89:6482-6486 (1992)), and smooth muscle cells (Quantin et al., *Proc. Natl. Acad. Sci. USA* 89:2581-2584 (1992)). Furthermore, the virus particle is relatively stable and amenable to purification and concentration, and as above, may be modified so as to affect the spectrum of infectivity. Additionally, introduced adenoviral DNA (and foreign DNA contained therein) is not integrated into the genome of a host cell but remains episomal, thereby avoiding potential problems that may occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, *J. Virol.* 57:267 (1986)). Most replication-defective adenoviral vectors currently in use and therefore favored for the present invention delete almost all of the viral E1 and E3 genes but otherwise retain as much as 80% of the adenoviral genetic material (see, e.g., Jones et al., *Cell* 16:683 (1979); Berkner et al., supra; and Graham et al. in *Methods in Molecular Biology* 7:109-127 (1991)). Expression of the inserted gene or other nucleic acid may be under control of, for example, the E1A promoter, the major late promoter (MLP) and associated leader sequences, the E3 promoter, or exogenously added promoter sequences.

Yet another viral vector system useful for delivery of a nucleic acid of interest is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., *Curr. Topics in Micro. and Immunol.*, 158:97-129 (1992)). It is also one of the few viruses that may integrate its DNA into non-dividing cells, and exhibits a high frequency of stable integration (see for example Flotte et al., *Am. J. ReMir. Cell. Mol. Biol.* 7:349-356 (1992); Samulski et al., *J. Virol.* 63:3822-3828 (1989); and McLaughlin et al., *J. Virol.* 62:1963-1973 (1989)). Vectors containing as little as 300 base pairs of AAV may be packaged and may integrate. Space for exogenous DNA is limited to about 4.5 kb. An AAV vector such as that described in Tratschin et al., *Mol. Cell. Biol.* 5:3251-3260 (1985) may be used to introduce DNA into cells. A variety of nucleic acids have been introduced into different cell types using AAV vectors (see for example Hermonat et al., *Proc. Natl. Acad. Sci. USA* 81:6466-6470 (1984); Tratschin et al., *Mol. Cell. Biol.* 4:2072-2081 (1985); Wondisford et al., *Mol. Endocrinol.* 2:32-39 (1988); Tratschin et al., *J. Virol.* 51:611-619 (1984); and Flotte et al., *J. Biol. Chem.* 268:3781-3790 (1993)).

Other viral vector systems that may have application in the present invention have been derived from herpes virus, vaccinia virus, and several RNA viruses. In particular, herpes virus vectors may provide a unique strategy for persistent expression of a nucleic acid of interest in cells of the central nervous system and ocular tissue (Depose et al., *Invest Ophthalmol Vis Sci* 35:2662-2666 (1994)).

In addition to viral transfer methods, such as those illustrated above, other types of delivery agents, and methods for their use, are contemplated by the present invention. In certain instances, such non-viral agents and methods may be employed to cause expression of subject recombinant proteins in the tissue of a host. Most nonviral methods of gene transfer rely on normal mechanisms used by mammalian cells for the uptake and intracellular transport of macromolecules. In certain embodiments, non-viral systems of the present invention rely on endocytic pathways for the uptake of the gene by the targeted cell. Exemplary systems of this type include liposomal derived systems, poly-lysine conjugates, artificial viral envelopes, amphiphilic molecules, and other materials designed to facilitate entry of any nucleic acid into a cell.

In a representative embodiment, a gene encoding one of the subject proteins may be entrapped in liposomes bearing positive-charges on their surface (e.g., lipofectins). For example, lipofection of neuroglioma cells may be carried out using liposomes tagged with monoclonal antibodies against glioma-associated antigen (Mizuno et al., *Neurol. Med. Chir.* 32:873-876 (1992)).

A variety of amphiphilic compounds may serve as delivery agents. See generally U.S. Pat. No. 5,925,628. Compounds that have both a polar and non-polar domain may be termed amphiphiles, and many lipids and synthetic lipids that have been used as delivery agents meet this definition. One particularly important class of such amphiphiles is the cationic amphiphiles. In general, cationic amphiphiles have polar groups that are capable of being positively charged at or around physiological pH, and this property may be important in determining how amphiphiles interact with therapeutic agents. Two examples of such amphiphiles include bis-guanidiniumspermidine-cholesterol and bis-guanidinium-spermidine-trencholesterol derivatives. See, e.g., Vigneron et al., *Proc. Natl. Acad. Sci. USA* 93:9682-86 (1996). Other well-known amphiphilic compounds include: DOTMA (Felgner et al., *Proc. Natl. Acad. Sci. USA* 84:7413-17 (1987)); and DOGS (Behr et al., *Proc. Natl. Acad. Sci. USA* 86:6982-86 (1989)). See also Felgner et al., *Methods in Enzymology* 5:67-75 (1993); and U.S. Pat. Nos. 5,283,185, 5,264,618 and 5,334,761.

In yet another illustrative embodiment, the gene delivery system comprises an antibody or cell surface ligand which is cross-linked with a gene binding agent such as poly-lysine (see, for example, PCT publications WO93/04701, WO92/22635, WO92/20316, WO92/19749, and WO92/06180). For example, the subject gene construct may be used to transfect cells in vivo using a soluble polynucleotide carrier comprising an asialoglycoprotein conjugated to a polycation, e.g. poly-lysine (see U.S. Pat. No. 5,166,320). It will also be appreciated that effective delivery of the subject genes or other nucleic acids via receptor-mediated endocytosis may be improved using agents which enhance escape of the gene from the endosomal structures. For instance, whole adenovirus or fusogenic peptides of the influenza HA gene product may be used as part of the delivery system to induce efficient disruption of DNA-containing endosomes (Mulligan et al., *Science* 260-926 (1993); Wagner et al., *PNAS* 89:7934 (1992); and Christiano et al., *PNAS* 90:2122 (1993)).

2. Applications of Nucleic Acids a. Genes and Other Nucleic Acids

A variety of genes and other nucleic acids may be incorporated into the subject monomer and polymer compositions for use in in vitro and in vivo transfection systems. These recombinant sequences may be transcribable to RNA and/or expressible as protein molecules which render them useful as therapeutic agents.

Proteins of use in gene therapy include various hormones, growth factors, enzymes, lymphokines, cytokines, receptors, and the like. For example, vectors of the present invention may be used for direct gene replacement therapy, as in the case of replacing the function of a non-functional gene. Such direct replacement therapies have useful veterinary applications as well.

Among the genes that may be transferred in accordance with the invention are those encoding polypeptides that are absent, are produced in diminished quantities, or are produced in mutant form in individuals suffering from a genetic disease. Other genes of interest are those that encode proteins that have been engineered to circumvent a metabolic defect or proteins that, when expressed by a cell, may adapt the cell to grow under conditions where the unmodified cell would be unable to survive, or would become infected by a pathogen.

In addition the vectors may be used to produce anti-sense nucleic acids in target cells. Antisense therapy involves the production of nucleic acids that bind to a target nucleic acid, typically an RNA molecule, located within cells. The term antisense is so given because the oligonucleotides are typically complementary to mRNA molecules ("sense strands") which encode a cellular product targeted to selected cellular or viral gene expression products. Exemplary modes by which sequences may be targeted for therapeutic applications include: blocking the interaction of a protein with an RNA sequence (e.g., the interaction of RNA virus regulatory proteins with their RNA genomes); and targeting sequences causing inappropriate expression of cellular genes.

In addition, vectors of the present invention may be used to deliver sequences encoding catalytic RNA molecules into cells. For example, DNA sequences encoding a ribozyme of interest may be cloned into a vector of the present invention. Such a ribozyme may be a hammerhead ribozyme capable of cleaving a viral substrate, such as the Human Immunodeficiency Virus genome or an undesirable messenger RNA, such as that of an oncogene. The DNA-encoding ribozyme sequences may be expressed in tandem with tRNA sequences, with transcription directed from, for example, mammalian tRNA promoters.

In another embodiment, the subject compositions may be used to deliver a nucleic acid which is itself a "decoy," or which is transcribable by the host cell to provide a decoy nucleic acid. A decoy nucleic acid is a nucleic acid having a sequence recognized by a regulatory nucleic acid binding protein (i.e., a transcription factor). Upon expression, the transcription factor binds to the decoy nucleic acid, rather than to its natural target in the genome. Useful decoy nucleic acid sequences include any sequence to which a transcription factor binds.

In still other embodiments, the subject polymers may be used to transfect a cell with a recombinant gene encoding a "transdominant" protein. Such proteins may be dominant positive (agonists) or dominant negative (antagonists) with respect to all or a portion of the biological activities of a wild-type protein.

In general, the subject recombinant genes are provided in the form of an expression vector comprising the coding sequence operably linked to at least one regulatory element.

In certain instances, the coding sequence of the present invention may be operably linked to an inducible promoter. Several inducible promoter systems have been described, including those controlled by heavy metals (Mayo, K. E. et al., *Cell* 29:99-108 (1982)), RU-486, a progesterone antagonist (Wang, Y. et al., *Proc. Natl. Acad. Sci.* (*USA*) 91:8180-8184 (1994)), steroids (Mader & White, *Proc. Natl. Acad. Sci.* (*USA*) 90:5603-5607 (1993)) and tetracycline (Gossen & Bujard, *Proc. Natl. Acad. Sci.* (*USA*) 89:5547-5551 (1992)).

It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, may also be considered.

The recombinant gene which is employed may result in an intracellular product, i.e., retained in the cell, in the cytoplasm or organelle, e.g., the nucleus, in transport to a membrane, either an intracellular membrane or the cell membrane, or for secretion. In certain embodiments, particularly where the recombinant gene encodes a polypeptide product, it will be desirable for the gene product to be secreted or at least a portion of the protein presented on the extracellular surface of the host cell. Proteins may be directed for secretion by providing the natural secretion signal sequence, if available, or a heterologous secretion signal sequence. In some situations, where the soluble protein of interest is a fragment of a larger protein, it may be necessary to provide a signal sequence with such protein, so that upon secretion and processing at the processing site, the desired protein will have the natural sequence. Examples include growth hormone, Factor VIII, Factor IX, cytokines, angiogenic factors, transforming growth factors (TGFs), antagonists of cytokine receptors, glucose transporters, insulin receptors, contraceptives, or addressins to promote adhesion and migration to specific sites.

The expression vector may also include a marker for selection of host cells which contain the construct, particularly where the subject transfection system is to be used as part of an ex vivo gene therapy protocol. Normally, the marker will allow for positive selection, in providing protection from one or more cytotoxic agents. For example, neomycin resistance may be employed, where the cells may be selected with G418, dihydrofolate reductase may be employed for resistance to methotrexate, the cell sorter may be used to select cells expressing LacZ, and the like. The marker may be an inducible or non-inducible gene, so that selection may occur under induction or without induction.

The vector may also include a replication origin and such other genes as are necessary for replication in the host. The replication system comprising the origin and any proteins associated with replication encoded by the particular virus may be included as part of a construct. Care must be taken in selecting the replication system, so that the genes which are encoded for replication do not provide for transformation of the myoblasts. Illustrative replication systems include Epstein-Barr virus (Margolskee et al., *Mol. Cell. Biol.* 8:2837-2847 (1988)). Alternatively, replication defective vehicles may be employed, particularly replication defective retroviral vectors. Exemplary such vectors are described by Price et al., *Proc. Natl. Acad. Sci.* 84:156-160 (1987) and Sanes, et al., *EMBO J.* 5:3133-3142 (1986). The final vehicle construct may have one or more genes of interest. Either a cDNA gene or a chromosomal gene may be employed.

To further illustrate exemplary uses of the subject methods and reagents, the following list indicates various genes of interest and associated diseases, as appropriate, for which monomers or polymers of the present invention may be employed for gene therapy: (i) single gene defects: Factor IX and Factor VIII (hemophiliac: clotting disorders); alpha-1-antitrypsin (emphysema); growth hormone (inherited and acquired growth hormone deficiency); adenosine deaminase (other immunodeficiency disorders); enzyme defects (metabolic disorders); dystrophin (Duchenne and Becker muscular dystrophy); (ii) cancer: interferon (leukemia); interleukin-2 (Tcell activator: leads to tumor shrinkage); leuprolide: analog of human gonadotropin (ovarian and testicular); asparaginase (leukemia); monoclonal antibodies (specific IgG) to specific proteins; granulocyte colony stimulating factor (all cancers: allows higher doses of chemotherapy); (iii) brain: glucocerebrosidase (other lysosomal storage disorders; Tay Sachs); levodopa (Parkinson's); nerve growth factor (Alzheimer's); (iv) regulated expression systems: insulin (diabetes); glucose transporter (diabetes); growth factors: IGF-I and IGF-II; (v) infectious diseases: delivery of antisense sequences, toxin genes, or other genes into cells to interfere with expression of the pathogenic genetic functions; (vi) contraception: antibody to human chorionic gonadotropin; antibodies to zona pellucida antigens or sperm antigens; progesterone antagonist; (vii) pain: endorphins (dynorphin): endogenous-opiates; (viii) clotting disorders: Factor VIII and Factor IX (hemophilias); tissue plasminogen activator; (ix) organ and cell transplants: antibody to CD4 (HLA); (x) AIDS: growth hormone to stimulate lymphocyte proliferation; CD4 protein as a decoy to keep virus from interacting with CD4+cells; (xi) other: hormones, serum proteins, other humoral or diffusible proteins, and low molecular weight metabolic products.

In yet another embodiment, the subject invention may be used to deliver a "gene activation" construct which, by homologous recombination with a genomic DNA, alters the regulatory elements of an endogenous gene. For instance, the gene activation construct may replace the endogenous promoter of a gene with a heterologous promoter, e.g., one which causes constitutive expression of the gene or which causes inducible expression of the gene under conditions different from the normal expression pattern of the gene. A variety of different formats for the gene activation constructs are available. See, for example, PCT publications WO93/09222, WO96/29411, WO95/31560 and WO94/12650.

In certain embodiments, the nucleotide sequence used as the gene activation construct may be comprised of (i) DNA from some portion of the endogenous gene (exon sequence, intron sequence, promoter sequences, etc.) which direct recombination and (ii) heterologous regulatory element(s) which is to be operably linked to the coding sequence for the genomic gene upon recombination of the gene activation construct.

The gene activation construct is inserted into a cell, and integrates with the genomic DNA of the cell in such a position so as to provide the heterologous regulatory sequences in operative association with the native gene. Such insertion occurs by homologous recombination, i.e., recombination regions of the activation construct that are homologous to the endogenous gene sequence hybridize to the genomic DNA and recombine with the genomic sequences so that the construct is incorporated into the corresponding position of the genomic DNA.

The terms "recombination region" or "targeting sequence" refer to a segment (i.e., a portion) of a gene activation construct having a sequence that is substantially identical to or substantially complementary to a genomic gene sequence, e.g., including 5' flanking sequences of the genomic gene, and may facilitate homologous recombination between the genomic sequence and the targeting transgene construct.

As used herein, the term "replacement region" refers to a portion of an activation construct which becomes integrated into an endogenous chromosomal location following homologous recombination between a recombination region and a genomic sequence.

The heterologous regulatory sequences, e.g., which are provided in the replacement region, may include one or more regulatory elements, including: promoters (such as constitutive or inducible promoters), enhancers, negative regulatory elements, locus control regions, transcription factor binding sites, or combinations thereof. Promoters/enhancers which may be used to control the expression of the targeted gene in vivo include, but are not limited to, the cytomegalovirus (CMV) promoter/enhancer (Karasuyama et al., *J. Exp. Med.,* 169:13 (1989)), the human (β-actin promoter (Gunning et al., *PNAS* 84:4831-4835 (1987)), the glucocorticoid-inducible promoter present in the mouse mammary tumor virus long terminal repeat (MMTV LTR) (Klessig et al., *Mol. Cell. Biol.* 4:1354-1362 (1984)), the long terminal repeat sequences of Moloney murine leukemia virus (MuLV LTR) (Weiss et al., *RNA Tumor Viruses* (1985)), the SV40 early or late region promoter (Bernoist et al., *Nature* 290:304-310 (1981); Templeton et al., *Mol. Cell. Biol.,* 4:817 (1984); and Sprague et al., *J. Virol.,* 45:773 (1983)), the promoter contained in the 3' long terminal repeat of Rous sarcoma virus (RSV) (Yamamoto et al., *Cell*, 22:787-797 (1980)), the herpes simplex virus (HSV) thymidine kinase promoter/enhancer (Wagner et al., *PNAS* 82:3567-71 (1981)), and the herpes simplex virus LAT promoter (Wolfe et al., *Nature Genetics*, 1:379-384 (1992)).

In still other embodiments, the replacement region merely deletes a negative transcriptional control element of the native gene, e.g., to activate expression, or ablates a positive control element, e.g., to inhibit expression of the targeted gene.

b. Target Cells

The present invention may be used to introduce exogenous nucleic acid molecules into a variety of cells and tissues including, without limitation, muscle cells, endothelial cells, myeloid cells, bone marrow cells, stem cells (including hematopoietic and embryonic stem cells), lymphocytes, hepatocytes, fibroblasts, lung epithelial cells, embryonic cells, and nerve cells. In certain embodiments, the subject polymers may be used to transfect muscle or other cells of myocytic lineage.

A salient feature of certain embodiments of compositions of the present invention is the property of being able to transduce both proliferating and nonproliferating cells. This ability may be a significant advantage of the invention because of the proliferation characteristics of many of the target cells that one would like to transduce in various gene therapy protocols. In particular, many important target cells may alter their properties in undesirable ways when they divide, or they may divide very slowly, or they may not divide at all. Thus, the present invention may be useful in the transduction of such cells as normal muscle cells, normal hepatocytes, hematopoietic stem cells, neurons, quiescent lymphocytes, and normal epithelial cells (where "normal" refers only to the proliferative index of the cells). In terms of clinical practice, systems of the present invention may be useful in the treatment of a broad range of inherited and acquired diseases and medical conditions including, without limitation, hematologic diseases, cardiopulmonary diseases, endocrinological diseases, transplantation associated disorders, autoimmune disorders, neurodegenerative diseases, neoplasias, and the like.

(i) Muscle

The subject systems may also be used to transduce muscle cells in vitro and in vivo. Muscle is an important target for gene therapy in the treatment of several muscle and nerve diseases. Controlled gene expression in muscle may also be used to express genes that invoke an immune response, as well as to produce sustained levels of proteins that act on systemic disease.

Another reason that muscle may be used as a site for the delivery and expression of polynucleotides in a number of therapeutic applications is because animals have a proportionately large muscle mass which is conveniently accessed by direct injection through the skin; for this reason, a comparatively large dose of the subject gene therapy vectors may be deposited in muscle by single or multiple injections, and the nature of the slow-release polymers in certain embodiments may extend the gene therapy over long periods of time.

For instance, muscle disorders related to defective or absent gene products may be treated by introducing expression vectors or other constructs coding for a non-secreted gene product into the diseased muscle tissue. In another strategy, disorders of organs or tissues due to the absence of a gene product, and which results in the build-up of a circulating toxic metabolite, may be treated by introducing the specific therapeutic polypeptide into muscle tissue where the nonsecreted gene product is expressed and clears the circulating metabolite. In yet another strategy, an expression vector or other construct coding for a secretable therapeutic polypeptide may be injected into muscle tissue, from where the polypeptide is released into the circulation to seek a metabolic target. In still another embodiment, in immunization strategies, muscle cells may be injected with constructs coding for immunogenic peptides, and these peptides will be presented by muscle cells in the context of antigens of the major histocompatibility complex to provoke a selected immune response against the immunogen.

(ii) Nucleic Acid Vaccines

In embodiments, the subject systems may be used to form nucleic acid vaccines, e.g., DNA vaccines, for immunization against pathogens, cancer, and the like. DNA vaccination presents a number of features of potential value. Multiple antigens may be included simultaneously in the vaccination. Such vaccination may work even in the presence of maternal antibodies.

DNA vaccination may be applied to eliminate or ameliorate existing disease or conditions, including chronic infectious diseases. For instance, the subject DNA vaccines may be used for immunizing subjects against such infections as HSV, HIV, HCV, influenza, malaria, Ebola, hepatitis B, pappillomavirus and the like. Moreover, the DNA vaccines may also be employed as part of a protocol for induction of tolerance, such as in the treatment of allergies and other autoimmune conditions, such as multiple sclerosis, Type I diabetes, and rheumatoid arthritis.

The goal of vaccination is the induction of protective immunity. The target was once limited to infectious diseases, but has now broadened to include treatment of tumors, allergy, and even autoimmune diseases. The delivery of naked plasmid DNA results in the expression of the encoded antigen by muscle cells, and perhaps APCs, resulting in the induction of protective CTLs as well as antibody responses. This method of "genetic immunization" with polynucleic acid vaccines (PNV) may represent a significant advance in vaccination technology because it may be used repeatedly to immunize to different antigens while avoiding the risk of an infectious virus and the problem of the immune response to the vector.

DNA vaccination using systems of the present invention may produce different results from other vaccination efforts using DNA, such as naked injection of DNA. The pattern of antigen expression, both temporally and spatially, may differ from naked injection of DNA.

Formulations of the present invention may be used to deliver a coding sequence for an antigen(s) as part of a genetic immunization protocol. U.S. Pat. No. 5,783,567 and WO 94/04171 present a number of potential polypeptide sequences for inducing an immunogenic response.

The subject formulations may elicit a strong immune response even at low dose. The choice of monomer or polymer, along with selection of regulatory elements, may be used to optimize the vaccine response. For example, the polymeric formulation in which the nucleic acid or other material is incorporated, any payload of the monomeric units of the polymer, and other material encapsulated in the polymer may serve as an adjuvant, wherein an "adjuvant" is a substance that in combination with specific antigen may produce more immunity than the antigen alone. The size of any particles of the subject invention may affect immunogenicity. Additional adjuvants may be administered to enhance any inherent adjuvant effect of the subject polymer.

By controlling the rate of release from the polymers of the sequence giving rise to the antigen, it may be possible to prepare a single dose vaccine to replace a vaccination protocol requiring an initial vaccination followed by booster doses.

In another aspect of the present invention, a variety of DNA vaccination techniques may be employed with compositions of the present invention to elicit a stronger immune response. For example, in certain embodiments, a naked nucleic acid, such as DNA, may be administered along with a polymer of the present invention loaded with the same nucleic acid or, alternatively, a different nucleic acid or acids (as well as possibly other materials). In this example, the initial dose of naked nucleic acid followed by release of nucleic acid from the polymer may result in a more effective vaccination.

In embodiments, the subject method may be used as part of a vaccination against microbial pathogens. A major obstacle to the development of vaccines against viruses and bacteria, particularly those with multiple serotypes or a high rate of mutation, against which elicitation of neutralizing antibodies and/or protective cell-mediated immune responses is desirable, is the diversity of the external proteins among different isolates or strains. Since cytotoxic T-lymphocytes (CTLs) in both mice and humans are capable of recognizing epitopes derived from conserved internal viral proteins (Yewdell et al., *PNAS* 82:1785 (1985); Townsend, et al., *Cell* 44:959 (1986); McMichael et al., *J. Gen. Virol.* 67:719 (1986)); Bastin et al., *J. Exp. Med.* 165:1508 (1987); Townsend et al., *Annu. Rev. Immunol.* 7:601 (1989)), and are thought to be important in the immune response against viruses (Lin et al., *J. Exp. Med.* 154:225 (1981); Gardner et al., *Eur. J. Immunol.* 4:68 (1974); Taylor et al., *Immunol.* 58:417 (1986)), efforts have been directed towards the development of CTL vaccines capable of providing heterologous protection against different viral strains.

Those skilled in the art will recognize appropriate epitopes for use in generating an immunizing form of the subject formulations. It is known that CTLs kill virally- or bacterially-infected cells when their T cell receptors recognize foreign peptides associated with MHC class I and/or class II molecules. These peptides may be derived from endogenously synthesized foreign proteins, regardless of the protein's location or function within the pathogen. By recognition of epitopes from conserved proteins, CTLs may provide heterologous protection. In the case of intracellular bacteria, proteins secreted by or released from the bacteria are processed and presented by MHC class I and II molecules, thereby generating T-cell responses that may play a role in reducing or eliminating infection.

In an exemplary embodiment, the subject method may be used to produce a protective vaccination against infection by *Mycobacterium tuberculosis*. Genes encoding *Mycobacterium tuberculosis* proteins may be cloned into eukaryotic expression vectors, and formulated into the subject polymeric particles for expression of the encoded proteins in mammalian muscle cells in vivo.

(iii) Treatment of Dystrophic Muscle Diseases

Another application of the subject method is in the treatment of muscular dystrophy. The genetic basis of the muscular dystrophies is beginning to be unraveled. The gene related to Duchenne/Becker muscular dystrophy has recently been cloned and encodes a rather large protein, termed dystrophin. An attractive approach would be to directly express the dystrophin gene within the muscle of patients with Duchennes. Because most patients die from respiratory failure, the muscles involved with respiration would be a primary target.

The present systems may be used to express high levels of the following genes specifically in muscle tissue: the full length Duchenne's muscular dystrophy gene (dystrophin), the related sequence of the gene responsible for Becker's muscular dystrophy; myotonin protein kinase; alph alpha-subunit of Na+ channels; the 50 kd-dystrophin associated glycoprotein; myophosphorylase; phosphofructokinase; acid maltase; glycogen debrancing enzyme; phosphoglycerate kinase; phosphoglycerol mutase; lactate dehydrogenase; and carnitine palmitoyl transferase. The appropriate gene for the particular afflicted individual may be determined through genetic screening as known in the art.

(iv) Treatment of Heart Tissue

In embodiments, gene transfer into heart tissue using subject formulations may be used to treat both genetic and acquired heart disease. There are a variety of diseases and conditions affecting the heart tissue that could benefit from gene therapy.

Pathogenic changes associated with hereditary, environmental and infectious disease may selectively or generally affect the heart endocardium, myocardium, epicardium and/or pericardium.

The myocardium is an example of a target for gene therapy directed to the heart. The myocardium is the thickest layer of the heart containing the cardiac muscle cells, the impulse conducting system and connective tissue. Myocardial disease occurs in many forms of heart disease including myocardial infarction, rheumatic heart disease, and hypertensive heart disease. A number of myocardial pathologies involve inflammatory reactions that may impair heart function and persist for long periods of time. Untreated, the inflammatory reaction may produce focal necrosis and compromise cardiac function. In fact, many forms of myocarditis have unknown etiologies. Here the single most apparent symptom upon autopsy is an overwhelming immune response isolated within the cardiac muscle tissue. For these inflammatory diseases, gene therapy may be used to control the immune response. For example, antisense oligonucleotides may be used to control lymphokine release from inflammatory cells.

A construct which is transcribed to an antisense molecule may be designed once a DNA sequence for a particular gene is identified. For example, elevated IL-6 levels are observed both in cardiac inflammation associated with adventitious agents and autoimmune disease. It may therefore be beneficial to deliver IL-6 "antisense construct," e.g., which is transcribed to an antisense RNA that hybridizes to IL-6 mRNA, to control IL-6 release from immune cells within the heart. The cDNA sequence for IL-6 is provided in a publication by Hirano et al. (*Nature* 324:73-76, 1986) and Green et al. review the use and application of antisense polynucleotide to regulate protein expression (*Ann. Rev. Biochem.* 55:569-597, 1986). Tumor necrosis factor (TNF-α) is also implicated in IL-6 production and levels of TNF-α are increased at the site of inflammation. Such a mechanism to modulate TNF-α expression will prove beneficial for controlling localized immune responses in the heart. The sequence for TNF-α is provided by Pennica et al. (*Nature* 312:724, 1984). Alternatively, transforming growth factor (TGF-β) may be used to limit lymphocyte proliferation. An expression construct encoding a TGF-β protein may be introduced directly into heart cells to produce TGF-β thereby limiting lymphocyte proliferation within a localized area. The cDNA sequence for TGF-β is found in a publication by Derynck et al. (*Nature* 316:701-705, 1985). Similarly other growth factors or regulatory molecules may be used to selectively control other cells involved in the immune response.

If the causative agent for myocarditis is identifiable, then antisense polynucleotides or other regulatory proteins may be injected or introduced into the myocardium to act on that causative agent. These polynucleotide sequences may additionally be combined with sequences that encode polypeptides that control the immune response. Myocarditis is associated with rheumatic fever (Group A Streptococci), diphtheria, typhoid fever, scarlet fever and organisms causing infective endocarditis. Viral disorders causing myocarditis include influenza, poliomyelitis, mumps, measles, Epstein Barr virus, Coxsackie and ECHO viruses. In addition most rickettsial infections also induce some myocardial damage. Parasitic infections that may induce myocarditis and create cardiac abnormalities include Chagas' disease (*Trypanosoma cruzi*), toxoplasmosis and trichinosis. In addition, systemic lupus erythromatosus, scleroderma and generalized hypersensitivity reactions may also induce cardiac inflammation. More rarely, *Mycoplasma pneumoniae* and *Toxoplasma gondii* may induce myocarditis. Those conditions of unknown etiology that affect cardiac tissue include Fiedler's and giant cell myocarditis. These infectious agents induce inflammatory responses that may be controlled by the secretion of immunoregulatory polypeptides encoded by constructs delivered by the subject formulations.

Primary cardiomyopathies include arrhythmias, emboli valve insufficiency and ventricular obstruction. These pathologies may be either familial or acquired and may be amenable to gene therapy. However, for many of these myopathies, the specific causative agent has not yet been identified. Some myopathies, particularly those characterized by restricted ventricular filling, are primarily due to the overproduction of a given protein and would therefore benefit from gene therapy. For example, endocardial fibroelastosis is characterized by focal or diffuse cartilage-like fibroelastic thickening of the mural endocardium that may extend into the myocardium. The use of polynucleotide sequences, in accordance with the present invention, to control protein secretion would be of value.

Similarly, amyloidosis, the accumulation of amyloid protein, affects the heart and may be controllable by the therapy disclosed herein. Polynucleotide sequences encoding protein associated with amyloidosis are available in the literature and are readily identifiable to those with skill in the art. The introduction of antisense sequences by the subject compositions to control over-expression of a molecule or alternatively, the introduction of sequences coding for functional protein to correct the defective enzyme or regulatory protein responsible for the overproduction of a particular molecule, could prevent further deposit accumulation.

Some diseases thought to be "connective tissue" diseases also involve the heart. These include Rheumatoid arthritis, Lupus erythematosus, polyarthritis and scleroderma. Elevated levels of IL-6 are observed in systemic lupus erythematosus (SLE). As noted above, antisense sequences directed to IL-6 may be beneficial for controlling localized immune responses within cardiac tissue. In addition, Linker-Israeli et al. (*J. Immunol.* 147:117, 1991) have shown that TNF-α is useful to inhibit immune cell stimulation of SLE cells in vitro. Therefore the invention disclosed herein may additionally comprise the delivery of gene sequences encoding TNF-α (Pennica et al. supra). The immune response within the heart may be controlled using methods detailed herein.

Individuals with diabetes develop cardiomyopathies over time. Increased levels of atrial natriuretic peptide (ANP) mRNA are found in the heart tissue of some diabetics. The changes in levels of ANP synthesis occur before cardiomyopathic histological changes. ANP levels are even greater in diabetic conditions combined with hypertension (Drexler et al., *Circulation* 79:620 (1989)). Localized levels of ANP may be reduced through the delivery of polynucleotide directed at limiting ANP synthesis. The particular gene sequence chosen may correct a cellular defect associated with a particular cardiac disease or pathology. The gene sequence could encode a range of molecules as discussed and these molecules may be engineered to be expressed either intracellularly or extracellularly. Further, the polynucleotide may be a regulatory molecule of itself (e.g., anti-sense or the like) or encode regulatory or immunoregulatory molecules. The polynucleotide may additionally encode enzymes, hormones, and growth factors.

Cardiac treatment may be performed either prophylactically or on individuals with known cardiac sequelae. Characteristic symptoms of myocardial malfunction include, but are not limited to, arrhythmias, heart pain, cardiac enlargement, and congestive heart failure (predominantly of the right side).

Infusion of calcitonin gene related peptide, an alternate product in calcitonin synthesis, is beneficial for the treatment of congestive heart failure (Shekhar et al., Am. J. Cardiol. 67(8):732736 (1991)). Thus, it is additionally contemplated that the subject method may be used to deliver, to the hearts of those patients with congestive heart failure, expression vectors encoding enzymes involved in calcitonin synthesis. Inhibitors of angiotensin converting enzyme are beneficial in controlling experimental cardiac hypertrophy and congestive heart failure (Soubrier et al., *PNAS* 85:9386 (1988); and Michel, *Eur. Heart J.* 11 *Suppl.* D:17 (1990)). The subject compositions may be used to deliver a recombinant gene encoding protein, or transcribable into an antisense nucleic acid, which inhibits angiotensin converting enzyme.

In other embodiments, subject methods may be used to cause ectopic expression of adenosine receptors on the surface of the heart. Adenosine is a chemical produced by the heart that regulates heart function and protects the heart during periods of low oxygen supply.

(v) Myocytes as a Source of Secreted,
Recombinant Proteins

In embodiments, subject compositions may be used to cause ectopic expression, in myocytic cells, of a gene encoding a secreted protein. For example, the subject method may be used to deliver an expression vector cytokines, growth factors, (e.g., EGF, FGF, etc.), colony stimulating factors, interferons, surface membrane receptors, insulin or the like.

In embodiments, the subject transfection system may be used as part of a gene therapy protocol in the treatment of inflammatory disorders, lupus and colitis. To illustrate, monomers or polymers of the present invention may be used to treat certain forms of arthritis by intramuscular gene therapy including ectopic expression of a transforming growth factor (TGF). Song et al., *J Clinical Investigation* 101:12 (1998) recently reported that plasmid DNA, injected directly into muscle tissue, encoding transforming growth factor-β suppresses chronic disease in a streptococcal cell wall-induced arthritis model. This procedure was observed to reduce dramatically chronic arthritis symptoms in the joints, and now offers an innovative approach for eventually treating human disease. In this report, researchers tested the TGF plasmid in a rat model for human rheumatoid arthritis. In this model, animals that are injected in the abdomen with a preparation of bacterial cell walls soon develop swollen and inflamed joints in the feet. The acute arthritic phase lasts several days and then develops into a long-term chronic condition that is marked by the erosion of cartilage and bone within the joints. When the animals were intramuscularly injected with TGF-encoding plasmids, a dramatic reduction in disease symptoms in the joints was observed. The number of affected joints and the amount of swelling in the joints were both substantially reduced.

This study also demonstrated that the manner in which the protein was administered to the animals affected whether or not the outcome was favorable. Injecting TGF directly into joints led to a worsening of the condition. On the other hand, injection of the protein into the abdomen or under the skin, which delivers TGF into the blood stream, dramatically improved symptoms. However, this route of delivery also carries the risk of bone marrow suppression, anemia, and formation of fibrous tissues in the kidneys-undesirable side effects associated with exposing the entire body to high levels of TGF. However, using the gene therapy approach rather than administration of the protein permits the production of a low-level supply of TGF that affects the inflammatory response in the joints without disrupting the balance of other bodily functions. The TGF expression system of Song et al., supra, may be adapted for delivery by monomers or polymers of the present invention.

In another embodiment, subject compositions may be used to cause ectopic expression of an angiogenic growth factor to stimulate the development of collateral arteries, e.g., as part of a "therapeutic angiogenesis" treatment approach. In an exemplary embodiment, polymers of the present invention are used to treat ischemic ulcers by ectopic expression of vascular endothelial growth factor (VEGF) in muscle of the afflicted limb.

To illustrate, Baumgartner et al., *Circulation* 97:1114 (1998) reported that preclinical studies have indicated that angiogenic growth factors may stimulate the development of collateral arteries. In that study, naked plasmid DNA encoding the 165-amino-acid isoform of human vascular endothelial growth factor (phVEGF(165)) was injected directly into the muscles of limbs of patients with non-healing ischemic ulcers. The investigators reported newly visible collateral blood vessels, qualitative evidence of improved distal flow in limbs, and marked improvement in healing of ischemic ulcers. The VEGF vectors of Baumgartner et al., supra, may be adapted for delivery by monomers or polymers of the present invention.

In still other embodiments, the subject method may be used for ectopic expression of growth hormone or insulin like growth factor I (IGF-1). Growth hormone is normally produced and secreted from the anterior pituitary and promotes linear growth in prepuberty children. Growth hormone acts on the liver and other tissues to stimulate the production of IGF-I. This factor is, in turn, responsible for the growth promoting effects of growth hormone. Further, this factor serves as an indicator of overall growth hormone secretion. Serum IGF-I concentration increases in response to endogenous and exogenous administered growth hormone. These concentrations are low in growth hormone deficiency. Insulin-like growth factors are one of the key factors that potentiate muscle development and muscle growth. Myoblasts naturally secrete IGF-I/IGF-II as well as its cognate binding proteins during the onset of fusion. This process coincides with the appearance of muscle specific gene products. In terminally differentiated muscle, signals propagated from passive stretch induced hypertrophy induce the expression of IGF genes. Many of the actions of IGFs on muscle result from interactions with the IGF-I receptor. The intramuscular delivery of an expression vector containing the sequence for growth hormone or IGF-I may be used to treat growth disorders. Because intramuscular expression using the subject polymers may lead to expression of the GH or IGF-I product for extended periods of time, the subject method may provide a long-term inexpensive way to increase systemic blood concentration of IGF-I in patients with growth hormone deficiency.

Moreover, growth hormone levels decline with increasing age. The levels in healthy men and women above age 55 are approximately one third lower than the levels in men and women 18 to 33. This is associated with a decrease in the concentration of IGF-I. The decline in growth hormone and IGF-I production correlate with a decrease in muscle mass, termed senile muscle atrophy, and an increase in adiposity that occur in healthy human subjects. Administering growth hormone three times a week to healthy 61 to 81 year old men who had serum levels below those of healthy younger men increased the serum IGF-I levels to within the range found in young healthy adults. This increased level led to increased muscle mass and strength and reduced body fat. The secretion of growth hormone is regulated by a stimulatory (growth hormone releasing hormone) and an inhibitory (somatostatin) hypothalamic hormone.

Systems of the present invention may be used to deliver expression vectors encoding growth hormone, the growth hormone releasing hormone (GHRH), or IGF-I. This versatility is important since the GHRH, GH, and IGF-I, while having equivalent desired effects on muscle mass, may have different side effects or kinetics which may affect their efficacy. The expression of the growth factor releasing hormone might be more advantageous than the expression of either IGF-I or the growth hormone vector transcripts. Since GHRH is reduced in the elderly it appears to be responsible for the lack of GH secretion rather than the anterior pituitary capability of synthesizing growth hormone, thus the increased expression of GHRH from muscle would increase GHRH levels in the systemic blood system and may allow for the natural diurnal secretion pattern of GH from the anterior pituitary. In this way, GHRH could act as the natural secretogogue, allowing for elevated secretion or release of GH from the hypothalamus of the elderly.

Thus, the application of monomers and polymers described herein to express insulin-like growth factors through the ectopic expression of IGF-I, HG, or GHRH into adult muscle of the elderly may represent a long-term inexpensive way to increase systemic blood concentration of IGF-I in the elderly.

(vi) Treatment of Atherosclerotic Cardiovascular Diseases

Atherosclerotic cardiovascular disease is a major cause of mortality in the United States and the world. The atherosclerotic plaque, the basic underlying lesion in atherosclerosis, contains cholesterol esters that are derived from circulating lipids. These circulating lipids are essential to the development of atherosclerosis. The plasma concentration of high density lipoprotein (HDL) is inversely related to the propensity for developing atherosclerosis. In the nascent state, HDL is secreted in the form of discoidal particles. These particles consist of a bilayer of phospholipids onto which the apolipoproteins (ApoA-I, ApoII and E) are embedded. HDL captures cholesterol esters by the action of an enzyme, lecithin-cholesterol acyltransferase. HDL is secreted from the liver, the small intestine and possibly other tissues.

The ApoA-I cDNA is 878 bp and encodes 267 amino acids, including the 24 amino acid propeptide. Increasing the circulating levels of HDL may influence or reverse cholesterol transport, and thus reduce the propensity for forming atherosclerotic plaques. The insertion of the human ApoA-I coding sequences into an expression vector of the present invention may enhance ApoA-I expression following transfection of that vector into skeletal muscle, and may be used to increases the plasma concentration of HDL.

(vii) Other Tissue

In embodiments, subject systems may be used as part of a gene therapy protocol for treatment of liver diseases that are, for example, genetically based, as for example Wilson's disease, glycogen storage diseases, urea enzyme defects, and Creigler-Najir disease. For example, the subject systems may be used to correct an inherited deficiency of the low density lipoprotein (LDL) receptor, and/or to correct an inherited deficiency of ornithine transcarbamylase (OTC), which results in congenital hyperammonemia.

In embodiments, subject systems may be used to treat acquired infectious diseases of the liver, such as diseases resulting from viral infection. For example, the vectors may be employed to treat viral hepatitis, particularly hepatitis B or non-A non-B hepatitis. For example, a polymer of the present invention, containing a gene encoding an antisense gene, could be transduced into hepatocytes in vivo to inhibit viral replication. In this case, the infectious viral particle, which includes a vector including a structural hepatitis gene in the reverse or opposite orientation, may be introduced into hepatocytes, resulting in production of an antisense gene capable of inactivating the hepatitis virus or its RNA transcripts. Alternatively, the hepatocytes may be transduced with a vector which includes a gene encoding a protein, such as, for example, α-interferon, which may confer resistance to the hepatitis virus.

Crigler-Najjar syndrome is an autosomal recessive disorder which causes severe jaundice in affected children. Mutation of both alleles of the bilirubin gulcuronosyl transferase (BUGT) gene results in an inability to excrete bilirubin, which then accumulates in the body. The resulting jaundice is unremitting, leading inevitably to brain damage (spasticity, deafness, dementia) and death. The genes for human BUGTs have been cloned by others and an animal model of this syndrome is available. The subject systems may be used to deliver the human BUGT gene to hepatocytes in vivo. The response to this gene transfer therapy may be easily monitored by measuring the patient's serum bilirubin level. Correction of the BUGT defect via gene therapy may provide an alternative to transplantation, the only other therapy currently available.

In embodiments, the subject transfection system may also be used to transfect neuronal cells or endothelial cells.

In embodiments of the present invention, DNA vaccination may use mucosal delivery, which allows for easy administration, reduced side-effects, and the possibility of frequent boosting without requiring trained medical personnel. Mucosal delivery of vaccines appears to be effective for inducing immune responses in the mucosal secretions. In addition, many pathogens enter the body through the mucosal tissues of the gut or the respiratory or genital tracts.

Another application of the subject systems is in the treatment of cystic fibrosis. The gene for cystic fibrosis was recently identified (Goodfellow, *Nature,* 341(6238):102-3 (Sep. 14, 1989); Rommens, J. et al., *Science* 245(4922): 1059-1065 (Sep. 8, 1989); Beardsley, T. et al., *Scientific American,* 261(5):28-30 (1989)). Significant amelioration of the symptoms may be attainable by the expression of the dysfunctional protein within the appropriate lung cells. The bronchial epithelial cells are postulated to be appropriate target lung cells, and they may be accessible to gene transfer following instillation of genes into the lung. Since cystic fibrosis is an autosomal recessive disorder, one may need to achieve only about 5% of normal levels of the cystic fibrosis gene product in order to ameliorate significantly the pulmonary symptoms.

Biochemical genetic defects of intermediary metabolism may also be treated by the subject method. These diseases include phenylketonuria, galactosemia, maple-syrup urine disease, homocystinuria, propionic acidemia, methylmalonic acidemia, and adenosine deaminase deficiency. The pathogenesis of disease in most of these disorders fits the phenylketonuria (PKU) model of a circulating toxic metabolite. That is, because of an enzyme block, a biochemical that is toxic to the body accumulates in body fluids. These disorders are ideal for gene therapy for a number of reasons. First, only 5% of normal levels of enzyme activity may need to be attained in order to clear significantly enough of the circulating toxic metabolite so that the patient experiences significant improvement. Second, the transferred gene may be expressed in a variety of tissues and still be able to clear the toxic biochemical. Similar transfection of pancreatic islet cells utilizing a formulation described herein may prove useful in the treatment of insulin dependent diabetes mellitus.

D. Vascular Tissue Support Structures and Matrices

The present invention also relates to a method to provide functional organ equivalents using bioabsorbable artificial substrates as temporary scaffolding for cellular growth, replication, transfer and implantation. Isolated cells are unable to form new tissues on their own. Most cells have a requirement for attachment to a surface in order to replicate and function. They require specific environments which very often include the presence of supporting material to act as a template for growth. Three-dimensional scaffolds may be used to mimic their natural counterparts, the extracellular matrices of the body. They serve as both a physical support and an adhesive substrate for isolated parenchymal cells during in vitro culture and subsequent implantation.

This method for replacing or supplementing lost organ function has a number of advantages over either pharmacologic manipulation or transplantation of whole organs or parts of organs. Although great strides have been made in these areas, the results of these efforts are often imperfect. Success in transplantation or pharmacologic manipulation may modify the outcome of a disease, but it usually does not result in cure, or it replaces the original disease with the complications of non-specific immunosuppression.

For an organ to be constructed in tissue culture and subsequently successfully implanted, the matrices need sufficient surface area and exposure to nutrients such that cellular growth and differentiation can occur prior to the ingrowth of blood vessels following implantation. After implantation, the configuration would allow for diffusion of nutrients and waste products and for continued blood vessel ingrowth as cell proliferation occurs. It is believed that cells require a matrix for attachment and support if they are to survive following implantation, that a minimum number of cells is essential for function in vivo, and that the matrix must be porous enough to allow nutrients and gases to reach all of the cells on and within the matrix by diffusion, until the matrix-cell structure is vascularized. Moreover, it is believed that synthetic biodegradable polymer may be used as a substrate to form a scaffold that mimics its natural counterparts, the extracellular matrices (ECM) of the body, serving as both a physical support and an adhesive substrate for isolated parenchymal cells during in vitro culture, and subsequent implantation, degrading as the cells begin to secrete their own ECM support. Subsequent studies have demonstrated that even better results may be obtained when the matrix is first implanted, prevascularized, and then seeded with cells. Most matrices used in the earlier work are modifications of materials already available, such as surgical sutures and meshes. In certain embodiments, polymers of the present invention may allow for suitable matrix constructions.

Such matrices may be prepared by methods known to those of skill in the art, for example as described below. Biocompatible porous polymer membranes are prepared by dispersing particles in a biocompatible polymer solution. Examples of possible biodegradable polymers include the subject polymers and polyorthoesters, poly(lactic acid), poly (DL-lactic-co-glycolic acid) (PLGA), and blends thereof. Particles may be formed of salts, polysaccharides, proteins, polymers other than the matrix polymers or other-non toxic materials which are soluble in a solvent that does not dissolve the polymers used to form the matrix. The solvent in which the polymer is dissolved is evaporated to produce a polymer/particle composite membrane. The polymer may be heated and cooled at a predetermined constant rate to provide the desired amount of crystallinity. Salt or other particles may then be dissolved out of the membrane by immersing the membrane in water or another solvent for the particles but not the polymer. The membrane may then be dried to provide a porous, biocompatible membrane to which dissociated cells may be attached and proliferate.

There are a variety of means of preparing matrices of the subject compositions. A three-dimensional structure may be manufactured using the polymer membranes by preparing a contour drawing of the shape of the structure, determining the dimensions of thin cross-sectional layers of the shape, forming porous polymer membranes corresponding to the dimensions of the layers, and laminating the membranes together to form a three-dimensional matrix having the desired shape. The membranes are laminated by wetting one side of each of two membranes, placing one membrane on top of the other with the wetted surfaces touching, and applying sufficient force to affix the membranes. The laminating procedure may be repeated until all of the membranes are laminated together to produce the desired three-dimensional shape. Excess portions of the matrix can be excised with a scalpel or other instrument to create crevices or openings as desired, as described in U.S. Pat. No. 5,514,378.

Certain embodiments of the present invention may allow for some of the advantages realized by the use of such matrices. For example, an advantage of the present method is that it provides a means for selective transplantation of parenchymal cells which possess the necessary biologic function, without transplantation of passenger leucocytes and antigen-presenting cells. The result is generally a greatly reduced risk of rejection of tissue without the use of drugs, especially if one is able to culture cells of the same or similar HLA tissue type. Embodiments of the present invention may also have another advantage over other means for treating organ function loss because the cells may be manipulated while in culture to introduce new genes to make absent protein products or they may be modified to repress antigen expression on the cell surfaces so that immunosuppressive therapy is not needed when cells of the same HLA tissue type are not available.

The prospect of culturing the recipient's own cells for implantation has a further advantage: the elimination of the need for organ donors. For example, if a patient has lost 90% of his intestine because of ischemic damage, cells from the remaining 10% may be harvested and cultured. The cells expand in a logarithmic fashion in culture. The cells are cultured until suitable numbers of cells are achieved, the cells are grown onto an appropriate polymer scaffold, and placed back into the patient, to be allowed to vascularize, grow and function as a neointestine.

The present method for controlled implantation of functional cells into patients using polymers as temporary scaffolding produces an organ which is vascularized in vivo to allow growth of the cells in a three-dimensional configuration similar to that of the organ whose function they are replacing. Both the design and construction of the scaffolding, as well as the conditions of the initial cell culture may be used to encourage cells to achieve their biological potential and replicate the ontogeny of organ formation which occurs in embryonic and fetal life. This new technique is termed chimeric neomorphogenesis.

The design and construction of the scaffolding is often of primary importance. The matrix may be shaped to maximize surface area to allow adequate diffusion of nutrients and growth factors to the cells. The maximum distance over which adequate diffusion through densely packed cells can occur appears to be in the range of approximately 200 to 300 microns under conditions similar to those that occur in the body, wherein nutrients and oxygen diffuse from blood vessels into the surrounding tissue.

In certain embodiments of the present invention, cells may be initially cultured using techniques known to those skilled in the art of tissue culture. Once the cells have begun to grow and cover the matrix, they may be implanted in a patient at a site appropriate for attachment, growth and function. One potential advantage of the biodegradable material is that it does not have to be removed once cell growth and formation of a functional mass has occurred.

Another potential advantage of the biodegradable material is that compounds and other materials may be incorporated into the matrix for slow release during degradation of the matrix. For example, angiogenic compounds, nutrients, growth factors, inducers of differentiation or dedifferentiation, products of secretion, immunomodulators, inhibitors of inflammation, regression factors, biologically active compounds that enhance or allow ingrowth of the lymphatic network or nerve fibers, and drugs can be incorporated into the matrix or provided in conjunction with the matrix, in solution or incorporated into a second biodegradable polymer matrix. As the cell-polymer structure is vascularized and the structure degrades, the cells will differentiate according to their inherent characteristics. For example, cells that would normally form tubules within the body may shape themselves into structures resembling tubules and nerve cells may extend along an appropriately constructed pathway.

In certain embodiments, the matrix is formed of a bioabsorbable, or biodegradable, cyanoacrylic polymer, optionally in conjunction with a polyanhydride, polyorthoester, or polyglycolic acid, and/or coated with extracellular components such as basement membrane components, agar, agarose, gelatin, gum arabic, collagens, fibronectin, laminin, glycosaminoglycans, mixtures thereof, and other materials having properties similar to biological matrix molecules known to those skilled in the art of cell culture to enhance cell attachment. Other polymer materials may be used, depending on the ultimate disposition of the growing cells, including polymethacrylate, silicon polymers, and other non-biodegradable materials.

In certain embodiments, a non-degradable material may be useful when the cells are grown in culture for purposes other than transplantation since the preferred matrix structure allows for a higher immobilized cell density than can normally be achieved where nutrients are supplied solely by diffusion. This matrix structure allows the in vitro study of various types of cells in combination, biochemical signals for growth, differentiation, migration and various extracellular matrix components. These studies are particularly useful in understanding cell to cell interaction: behavior, communication, control, and morphogenesis.

A variety of methods and means known to those of skill in the art may be adapted for use with the present polymeric compositions, whereby cells having a desired function are grown on polymer scaffolding shaped to maximize surface area to allow adequate diffusion of nutrients and growth factors to the cells. Using cell culture techniques, followed by transfer of the cell-polymer scaffold into a patient at a site appropriate for attachment, growth and function, after attachment and equilibration, a functional organ equivalent may be produced. Success depends in part on the ability of the implanted cells to attach to the surrounding environment and to stimulate angiogenesis. Nutrients and growth factors are supplied during cell culture allowing for attachment, survival or growth as needed.

After the structure is implanted and growth and vascularization take place, the resulting organoid is a chimera formed of parenchymal elements of the donated tissue and vascular and matrix elements of the host. In certain embodiments of the present invention, the polymer scaffolding used for the initial cell culture is constructed of a material that degrades over time and is therefore not present in the chimeric organ. Vascular ingrowth following implantation allows for normal feedback mechanisms controlling soluble products of the implanted cells.

The material for forming the matrix or support structure in embodiments of the present invention is a biodegradable cyanoacrylic polymer, optionally employed in conjunction with other suitable polymers or materials, such as polyglycolic acid, polyorthoester, or polyanhydride, which may be degraded by hydrolysis at a controlled rate and reabsorbed. These materials allow the degradability, manageability, size and configuration to be controlled, although other materials, including non-biodegradable materials such as polytetrafluoroethylene may be used. In some embodiments, these materials may be overlaid with a second material such as gelatin or agarose to enhance cell attachment.

As a general matter, the polymer matrix could be configured to provide both adequate sites for attachment and adequate diffusion of nutrients from the cell culture to maintain cell viability and growth until the matrix is implanted and vascularization has occurred. One exemplary structure for organ construction is a fibrous three dimensional structure formed of polymer fibers having a high surface area, which results in a relatively shallow concentration gradient of nutrients, wastes, and gases, so as to produce uniform cell growth and proliferation.

A variety of different cells may be used with matrices of the present invention. In certain embodiments, endocrine cells such as hepatocytes, pancreatic cells or cells of the adrenal gland are proliferated on the matrices. Other cells, such as cells of the nervous system, including hypothalamus and pituitary cells, lymphoid cells, mesodermal cells, such as fibroblasts, endothelial cells, and lymphatic cells, splenic cells, and genitourinary cells, for example, renal endocrine tissues, and sex related endocrine tissues, may also be grown and/or implanted using this method. In still other embodiments, stem cells may be used to seed the matrix.

The matrix structure and the length of time and conditions under which the cells are cultured in vitro are determined on an individual basis for each type of cell by measuring cell attachment (only viable cells remain attached to the polymers), extent of proliferation, and percent successful engraftment. As discussed above, it is not necessary to culture cells in vitro, other than for purposes of attaching the cells to the matrix, prior to implantation if sufficient numbers of cells are available. Cells generally attach within a few hours.

Matrices of the present invention may be used to replace or repair structural components of a patient. For example, damage of cartilage produced by disease, such as arthritis, or trauma is a major cause of physical deformity and debilitation. The primary therapy for loss of cartilage is replacement with a prosthetic material, such as silicone for cosmetic repairs, or metal alloys for joint realignment. Placement of prostheses is commonly associated with significant loss of underlying tissue and bone without recovery of the full function allowed by the original cartilage, as well as the irritating presence of a foreign body. Other long term problems associated with a permanent foreign body may include infection, erosion and instability. Implants capable of forming cartilage or bone tissue may use the polymeric compositions of the present invention.

VI. Coatings of Implantable Devices

Monomers and polymers as described herein may also be used to coat implantable devices, such as stents, catheters, artificial vascular grafts, and pacemakers and other medical devices. The coating may be useful for modulating the friction, wear-resistance, or impact resistance of a surface, for modifying the shape of the device, for reducing inflammatory or immune responses in the patient, or for any other reasons. The device may be coated with the lyophilized powder of injectable particles as described herein, a solution of polymer may be applied to the device, or a monomeric composition may be polymerized on the device. The coating may release therapeutic agents such as antibiotics, anti-inflammatories, or anti-clotting agents at a predetermined rate, to prevent or reduce complications related to the implanted devices.

Exemplifications

The present invention now being generally described, it may be more readily understood by reference to the following examples which are included merely for purposes of illustration of certain aspects and embodiments of the present invention, and are not intended to limit the invention.

The alanine tert-butyl ester hydrochloride compound was purchased from Bachem and all other chemicals were obtained from Aldrich Chemical.

An alanine-derived monomer was prepared by the method of Scheme I, using the procedures outlined below.

Scheme I

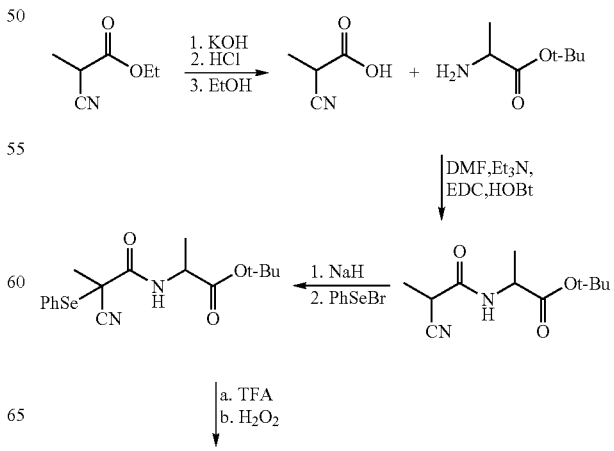

-continued

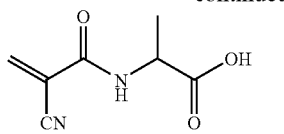

N-(2-cyanopropyl)alanine tert-butyl ester. To a solution of alanine tert-butyl ester hydrochloride (41.5 g, 228 mmol) in anhydrous dimethyl formamide (DMF, 35 mL) under argon was added triethylamine (35 mL) followed by 2-cyanopropionic acid (25 g, 252 mmol) and 1-hydroxybenzotriazole hydrate (HOBt, 40.5 g, 300 mmol). The resulting mixture was cooled to 0° C. and 1-[3-(dimethylamino)propyl]-3-ethylcarbodiimide hydrochloride (EDC, 48.8 g, 255 mmol) was added. The mixture was stirred at 0° C. for 2 h followed by 12 h at 23° C. The solvent was removed in vacuo, and the resulting residue was suspended in 300 mL of ethyl acetate. The organic layer was extracted with saturated aqueous NaHSO$_4$ and the precipitate that formed from the emulsion was filtered out. The organic layer was again extracted with saturated aqueous NaHCO$_3$ and saturated aqueous NaCl, dried over anhydrous MgSO$_4$ and concentrated to a viscous yellow oil. $^1$H NMR (CDCl$_3$): δ 1.4 (dd, 3H, CH$_3$—CH—NH—), 1.5 (s, 9H, (CH$_3$)$_3$), 1.6 (dd, 3H, CH$_3$—CH—CN—), 3.5 (q, 1H, NH—CH—CO$_2$Bu), 4.4 (m, 1H, CH$_3$—CH—CN), 6.8 (s, 1H, NH).

N-(2-cyano-2-phenylselenyl-propyl)alanine tert-butyl ester. In a 1 L two-necked flask was added sodium hydride (2.9 g, 121 mmol) and anhydrous DMF (235 mL) under argon. N-(2-cyanopropyl)alanine tert-butyl ester (25.2 g, 114 mmol) in anhydrous THF (210 mL) solution was added over 15 min and the reaction mixture was stirred at 23° C. for 12 h under argon. The reaction mixture was added to 300 mL each of ether and saturated aqueous NaHCO$_3$. The precipitate formed from the emulsion was filtered out. The aqueous layer was washed once with 100 mL saturated aqueous NaHCO$_3$, once with saturated aqueous NaCl, and twice with H$_2$O. The organic layer was separated, dried over anhydrous MgSO$_4$ and concentrated to a dark brown crude oil. The crude product was purified by flash chromatography. $^1$H NMR (CDCl$_3$): δ 1.35 (dd, 3H, CH$_3$—CH—NH—), 1.45 (s, 9H, (CH$_3$)$_3$), 1.9 (d, 3H, CH$_3$—C—CN—), 4.25 (NH—CH—CO$_2$Bu), 7.45 (m, 3H, Ph), 7.55 (m, 1H, NH), 7.8 (m, 2H, Ph).

Alanine(tert-butyl ester) cyanoacrylamide. To a 250 mL flask was added N-(2-cyano-2-phenylselenyl-propyl)alanine tert-butyl ester (8 g, 21 mmol) and methylene chloride (85 mL) and the mixture was cooled to 0° C. Hydrogen peroxide, 30% (24 g, 210 mmol) was dissolved in water (16 mL) and added slowly to the reaction flask over 20 min. After the addition was complete, the reaction mixture was stirred at 0° C. for 30 min. and at 23° C. for 45 min. The organic layer was separated and washed three times with H$_2$O, dried over anhydrous silicic acid, filtered, and placed in a refrigerator with one drop of concentrated H$_2$SO$_4$. Due to its sensitivity, the monomer was kept in solution in CH$_2$Cl$_2$ until use. $^1$H NMR (CDCl$_3$): δ 1.4 (d, 3H, CH$_3$—CH—NH—), 1.45 (s, 9H, (CH$_3$)$_3$), 4.45 (m, 1H, NH—CH—CO$_2$Bu), 6.5 (d, 1H, CH$_2$=C—CN—), 6.8 (s, 1H, NH), 7.0 (d, 1H, CH$_2$=C—CN—).

A second type of monomer was prepared by the method of Scheme II and the ensuing procedure.

Scheme II

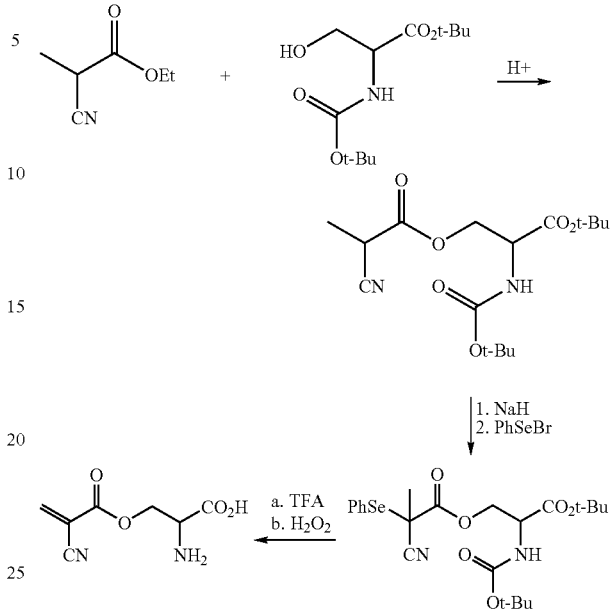

N-(2-cyanopropyl)-N-Boc-L-serine tert-butyl ester. To a 100 mL flask with a Dean-Stark condenser and an argon inlet was added N-Boc-L-serine tert-butyl ester 2 (5.00 g, 19.1 mmol), ethyl-2-cyanopropionate (3.65 g, 28.7 mmol), p-toluenesulfonic acid monohydrate (0.200 g, 1.05 mmol) and anhydrous toluene (60 mL). The reaction mixture was heated to reflux while stirring. Solvent was removed through the Dean-Stark trap and replaced with an equal amount of fresh toluene. After refluxing for 6 h, the reaction mixture was cooled to room temperature. The solution was washed once with saturated aqueous NaHCO$_3$, twice with H$_2$O, and twice with saturated aqueous NaCl. The organic layer was separated, dried over anhydrous MgSO$_4$, and concentrated to a viscous yellow oil. $^1$H NMR (CDCl$_3$): δ 1.43 (m, 21H, CH$_3$—CH—NH—, 2 (CH$_3$)$_3$), 3.25 (s, 1H, CH3-CH—CN), 3.85 (t, 2H, CO$_2$, —CH$_2$—CH—), 3.85 (t, 2H, CO$_2$—CH$_2$—CO$_2$Bu), 4.25 (s, 1H, NH—CH—CH$_2$—), 5.55 (d, 1H, NH). This material can be converted to the cyanoacrylic monomer by following the general procedure set forth above for the alanine-derived monomer.

REFERENCES

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

PATENTS AND PATENT APPLICATIONS

U.S. Pat. No. 3,527,841
U.S. Pat. No. 3,722,599
U.S. Pat. No. 3,995,641
U.S. Pat. No. 3,940,362
U.S. Pat. No. 4,741,337
U.S. Pat. No. 5,091,557
U.S. Pat. No. 5,190,922

U.S. Pat. No. 5,328,687
U.S. Pat. No. 5,759,830
U.S. Pat. No. 5,770,193
U.S. Pat. No. 5,736,372
WO 94/24095

PUBLICATIONS AND OTHER REFERENCES

Brady et al., 1998 J. Med. Chem, 41:401-406
Carre et al., 1998 Journal of Fluorescence, 8(1):53-57
Domb et al., 1989 Macromolecules, 22:3200
Heller et al., 1990 Biodegradable Polymers as Drug Delivery Systems, Chasin, M. and Langer, R., Eds., Dekker, New York, 121-161
Holland et al., 1986 Controlled Release, 4:155-180
Spilizewski et al., 1985 "The effect of hydrocortisone loaded poly(dl-lactide) films on the inflammatory response," J. Control. Rel. 2:197-203)
Vacanti, et al., "Selective cell transplantation using bioabsorbable artificial polymers as matrices" J. Pediat. Surg. 23, 3-9 (1988) and Vacanti, "Beyond Transplantation" Arch. Surg. 123, 545-549 (1988), describe an approach for making new organs for transplantation.

In addition to the foregoing materials, the practice of the present invention may employ in part, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins, eds., 1984); *Transcription And Translation* (B. D. Hames & S. J. Higgins, eds., 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al., eds.), *Immunochemical Methods In Cell And Molecular Biology* (Mayer and Walker, eds., Academic Press, London, 1987); Handbook Of Experimental Immunology, Volumes I-IV (D. M. Weir and C. C. Blackwell, eds., 1986); Manipulating the Mouse Embryo (Cold Spring Harbor Laboratory Press, Cold Spring Harbor, N.Y., 1986).

Equivalents

Those skilled in the art will recognize, or be able to ascertain using no more than routine experimentation, many equivalents to the specific embodiments of the invention described herein.

We claim:

1. A composition comprising a chemical moiety comprising the structure:

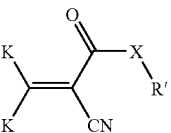

wherein:

K is H;

X is NR;

R is —H, —$(CH_2)_n$alkyl, —$(CH_2)_n$alkenyl, —$(CH_2)_n$alkynyl, —$(CH_2)_n$cycloalkyl, —$(CH_2)_n$heterocyclyl, —$(CH_2)_n$aryl or —$(CH_2)_n$heteroaryl;

n is an integer from 0 to 10;

R' is CH(Z)—CO—;

Z is H or substituted or unsubstituted alkyl, alkenyl, alkynyl, aryl or heterocyclyl moiety; and

[R'—X] comprises an amino acid residue.

2. A composition comprising a chemical moiety comprising the structure:

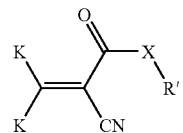

wherein:

K is H;

X is NR;

R is —H, —$(CH_2)_n$alkyl, —$(CH_2)_n$alkenyl, —$(CH_2)_n$alkynyl, —$(CH_2)_n$cycloalkyl, —$(CH_2)_n$heterocyclyl, —$(CH_2)_n$aryl or —$(CH_2)_n$heteroaryl;

n is an integer from 0 to 10;

R' is CH(Z)—CO—;

Z is H or substituted or unsubstituted alkyl, alkenyl, alkynyl, aryl or heterocyclyl moiety; and

[R'—X] comprises a residue of an amino acid selected from the group consisting of glycine, alanine, valine, cysteine, leucine, isoleucine, serine, threonine, methionine, glutamic acid, aspartic acid, glutamine, asparagine, lysine, arginine, proline, histidine, phenylalanine, tyrosine and tryptophan.

3. The composition of claim 1, wherein said residue is of an amino acid selected from the group consisting or glycine, alanine, valine, cysteine, leucine, isoleucine, serine, threonine, methionine, glutamic acid, aspartic acid, glutamine, asparagine, lysine, arginine, proline, histidine, phenylalanine, tyrosine, tryptophan, and an analog, derivative or congener of any of the foregoing.

4. The composition of claim 2, wherein said amino acid is an (L) stereoisomer.

* * * * *